US008841347B2

(12) United States Patent
Marona et al.

(10) Patent No.: US 8,841,347 B2
(45) Date of Patent: Sep. 23, 2014

(54) DERIVATIVES OF AMINOALKANOLS, METHOD OF OBTAINING OF AMINOALKANOLS AND THEIR USE

(71) Applicants: Anna Maria Waszkielewicz, Michalowice (PL); Uniwersytet Jagiellonski, Cracow (PL)

(72) Inventors: Henryk Marona, Cracow (PL); Anna Waszkielewicz, Cracow (PL); Katarzyna Kiec-Kononowicz, Cracow (PL)

(73) Assignees: Uniwersytet Jagiellonski, Cracow (PL); Anna Maria Waszkielewicz, Michalowice (PL)

( * ) Notice: Subject to any disclaimer, the term of this patent is extended or adjusted under 35 U.S.C. 154(b) by 70 days.

(21) Appl. No.: 13/853,542

(22) Filed: Mar. 29, 2013

(65) Prior Publication Data
US 2013/0289118 A1 Oct. 31, 2013

Related U.S. Application Data

(62) Division of application No. 12/863,881, filed as application No. PCT/PL2009/000004 on Jan. 19, 2009.

(30) Foreign Application Priority Data

Jan. 22, 2008 (PL) .......................... 384304

(51) Int. Cl.
| | | |
|---|---|---|
| A61K 31/135 | (2006.01) | |
| C07C 235/20 | (2006.01) | |
| C07C 217/16 | (2006.01) | |
| C07C 235/22 | (2006.01) | |
| C07C 217/20 | (2006.01) | |
| C07C 237/22 | (2006.01) | |
| C07C 217/18 | (2006.01) | |

(52) U.S. Cl.
CPC .......... *C07C 217/18* (2013.01); *C07B 2200/07* (2013.01); *C07C 235/20* (2013.01); *C07C 217/16* (2013.01); *C07C 235/22* (2013.01); *C07C 217/20* (2013.01); *C07C 2101/14* (2013.01); *C07C 237/22* (2013.01)
USPC .......................................................... 514/651

(58) Field of Classification Search
USPC .......................................................... 514/651
See application file for complete search history.

(56) References Cited

U.S. PATENT DOCUMENTS

| | | |
|---|---|---|
| 3,453,308 A | 7/1969 | Westland |
| 4,118,511 A | 10/1978 | Ferland et al. |

FOREIGN PATENT DOCUMENTS

| | | |
|---|---|---|
| EP | 1072591 A | 1/2001 |
| PL | 319557 | 10/1998 |
| WO | WO 2007/062399 | 5/2007 |

OTHER PUBLICATIONS

English translation of PL319557.
International Search Report dated Jul. 23, 2009 for PCT Application No. PCT/PL2009/000004.
Alexander, G.; et al. "Biphasic Action on Convulsive Seizures in Rodents," *Neurobehav. Toxicol. Teratol*, 1986, 8, 231-235.
Chew, C.Y.C.; et al. "A Review of Its Pharmacological Properites and Therapeutic Efficacy in Arrhythmias," *Drugs*, 1979, 17, 161-181.
Czuczwar, S.J.; et al. "Influence of Combined Treatment with NMDA and Non-NMDA Receptor Antagonists on Electroconvulsions in Mice," *Eur. J. Pharmacol.*, 1995, 281, 327-333.
Fischer, W. "Anticonvulsant Profile and Mechanism of Action of Propranolol and Its Two Enantiomers," *Seizure*, 2002, 11, 285-302.
Marona, H. "Synthesis and Anticonvulsant Activity of 1,2-aminoalkanol Derivatives," *Acta Pol. Pharm.—Drug Res.*, 1998, 55, 487-498.
Marona, H.; et al. "Anticonvulsant Activity of Some Xanthone Derivatives," *Bioorg. Med. Chem.*, 2008, 16, 7234-7244.
Marona, H.; et al. "Preliminary Evaluation of Anticonvulsant Activity of Some Aroxyacetamides and Aroxyethylamines," *Acta Pol. Pharm.*, 2005, 62, 345-353.
Marona, H.; et al. "Synthesis of Some N-acyl Derivatives of Optically Active trans-2-Amino-1-cyclohexanols," *Acta Pol. Pharm.—Drug Res.*, 1996, 53, 111-115.
Marona, H.; Szneler, E. "Preliminary Evaluation of Anticonvulsant Activity of Some 4-(Benzyloxy)-Benzamides," *Acta Poloniac Pharmaceutica—Drug Research*, 2003, 477-480.
Orlof, M.J. "Timed Intervenous Infusion of Metrazol and Strychnine for Testing Anticonvulsant Drugs," *Proc. Soc. Exp. Biol. Med.*, 1949, 70, 254-257.
Pekala, E.; et al. "Synthesis of New N-acyl Derivatives of DL-trans-1,2-Aminocyclohexanol," *Acta Pol. Pharm.—Drug Res.*, 1994, 51, 339-342.
Rogawaski, M.A.; et al. "Antiepileptic Drugs: Pharmacological Mechanisms and Clinical Efficacy with Consideration of Promising Developmental Stage Compounds," *Pharmacol. Rev.*, 1990, 42, 223-286.

(Continued)

*Primary Examiner* — Paul Zarek
(74) *Attorney, Agent, or Firm* — Christopher L. Parmelee; Walker & Jocke

(57) ABSTRACT

The subject of the invention is a group of new derivatives of aminoalkanols, more specifically [(phenoxy)alkyl]aminoalkanols and [(phenoxy)acyl] aminoalkanols, their method of obtaining and their use for production of a medicine which is used in the prophylaxis, prevention and/or treatment of diseases or symptoms having neurological background and for production a medicine with anticonvulsant activity, which is used in seizures of various origin, also in the limbic system, in myoclonic or sound-induced seizures, in psychomotor epilepsy, as well as relieving neuropathic or inflammatory pain.

11 Claims, 5 Drawing Sheets

(56) References Cited

OTHER PUBLICATIONS

Figure 1:
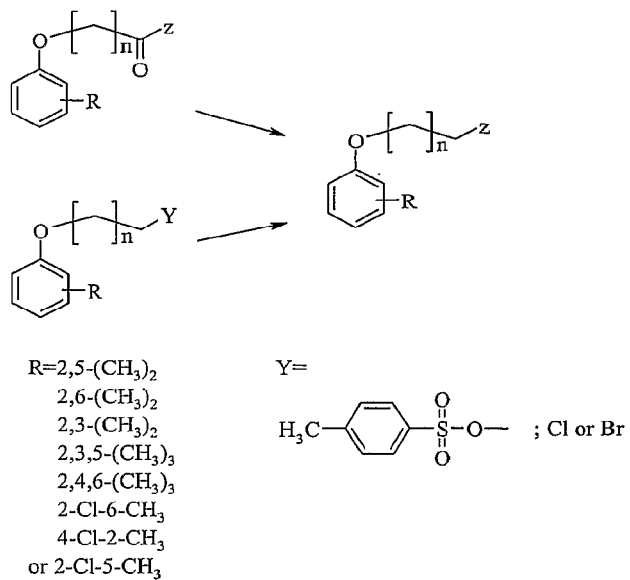
Figure 1:
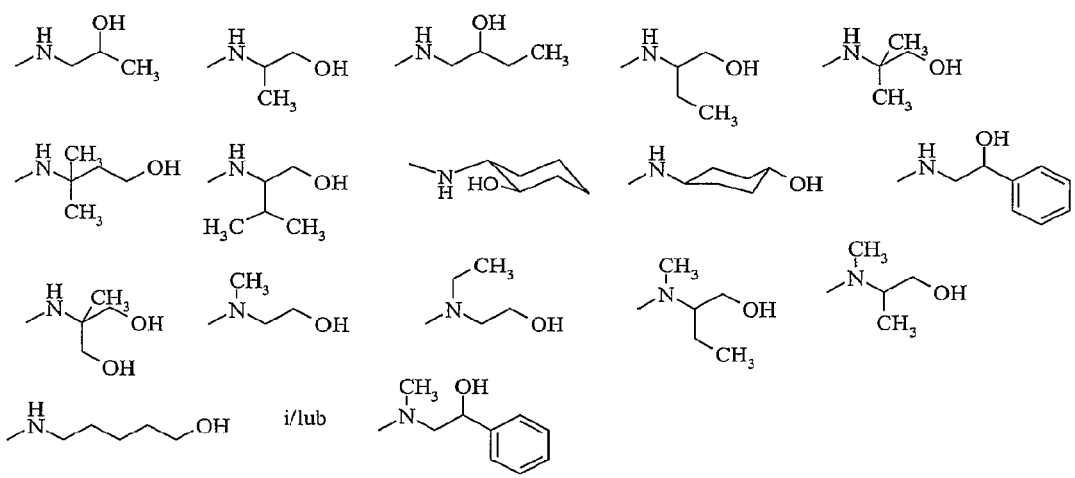

Stables J.P.; et al. "The NEH Anticonvulsant Drug Development (ADD) Program: Preclinical Anticonvulsant Screening Project," Chapter 16, http://www.ninds.nih.gov/funding/research/asp/ad-dadd_review._pdf_12, Kupferberg H. "Animal Models Used in the Screening of Antiepileptic Drugs," *Epilepsia*, 2001, 42, 7-12.

Swinyard, E.A.; et al. "General Principles: Experimental Selection, Quantification, and Evaluation of Anticonvulsants," *Antiepileptic Drugs, Str.* 1989, Wyd. 3. Raven Press, Nowy Jork, 85-102.

Waszkielewicz, A.M.; Cegla, M.; Marona, H. "Preliminary Evaluation of Anticonvulsant Activity of Some Aminoalkanol Derivatives," *15th International Symposium Molecular and Physiological Aspects of Regulatory Processes of the Organism*, Cracow, Poland, 2006, 3 pages.

Waszkielewicz, A.M.; et al. "Preliminary Evaluation of Anticonvulsant Activity of Some [4-(benzyloxy)-benzoyl]- and [4-(benzyloxy)-benzyl]-aminoalkanol Derivatives," *Acta Pol. Pharm.—Drug Res.*, 2007, 64, 147-157.

Wilkinson GR, Chapter 1 Pharmacokinetics—The Dynamics of Drug Absorption, Distribution, and Elimination, "Goodman & Gilman's The Pharmacological Basis of Therapeutics, 10th ed." Hardman JG, Limbird LE, and Gilman AG, Eds., McGraw-Hill, 2001, 3 & 5-8.

DERIVATIVES OF AMINOALKANOLS, METHOD OF OBTAINING OF AMINOALKANOLS AND THEIR USE

RELATED APPLICATIONS

This application is a Divisional of U.S. patent application Ser. No. 12/863,881, filed Jul. 21, 2010, which is a §371 filing based on PCT Application Serial No. PCT/PL2009/000004, filed Jan. 19, 2009, designating the United States and published in English, which claims the benefit of the filing date of Polish Patent Application No. P-384304, filed Jan. 22, 2008. All of the foregoing applications are hereby incorporated by reference.

DESCRIPTION

The subject of the invention is a group of new derivatives of aminoalkanols, more specifically [(phenoxy)alkyl]aminoalkanols and [(phenoxy)acyl]aminoalkanols, their method of obtaining and their use for production of a medicine which is used in the prophylaxis, prevention and/or treatment of diseases or symptoms having neurological background and for production a medicine with anticonvulsant activity, which is used in seizures of various origin, also in the limbic system, in myoclonic or sound-induced seizures, in psychomotor epilepsy, as well as relieving neuropathic or inflammatory pain.

Overview of literature concerning biological activity in a group of aminoalkanols indicates possibility to select compounds revealing anticonvulsant properties, e.g. among drugs stabilizing electric potential of cells exhibiting their own electric activity. Propranolol serves as an example, as it exhibits beneficial properties in treatment of hypertension and arrhythmia, as well as it reveals properties of preventing some kinds of seizures [1]. Similar profile can be seen with mexiletine exhibiting protection in MES, ScMet and sound-induced seizures [2]. It is important, that the mechanism responsible for inhibiting seizures in both propranolol and mexiletine is mainly inhibition of voltage-gated sodium channels, while in arrhythmia treatment both drugs act differently: via antagonism of β-adrenergic receptors or via opening potassium channels, respectively [3]. However, capability of mexiletine usage in epilepsy treatment is very low due to the fact that it lowers seizure threshold in a dose not much above $ED_{50}$ (maximum electroshock MES, mice, intraperitoneal) in spite of inhibiting focal seizures. This activity causes necessity to perform threshold tonic extension (TTE) test in preliminary pharmacological assays for all substances of similar structure, revealing anticonvulsant activity, in order to exclude this harmful pro-convulsant activity [4]. Moreover, in epilepsy treatment, using drugs like propranolol or mexiletine also exhibiting activity on the heart is not proper. Therefore, new structures should be modeled in such way, that they are active in Central Nervous System (CNS) only without interfering the Cardiovascular System (CVS).

Therefore, the basic purpose of the invention was to create new chemical compounds which are useful in therapy, especially in treatment or prevention of diseases or symptoms of neurological background. The invention concerns a group of substituted aminoalkanol derivatives, preferably (phenoxy)alkyl-and [(phenoxy)acetyl]aminoalkanols, their pharmaceutically acceptable salts and prodrugs, capable for use in treatment or prevention of diseases of neurological background. New compounds described in the patent application, exhibit anticonvulsant activity in various models of seizures, including Maximum Electroshock Seizures (MES, mice, rats), hippocampal kindling seizures (rats), and contain some elements of the structures (aminoalkanol moieties, aroxyalkyl group) of some known drugs used in treatment of arrhythmia (propranolol, mexiletine), which exhibit proved anticonvulsant activity [1, 2]. The common typical feature of activity of the new substances as well as mentioned antiarrhythmic drugs is influence on cells exhibiting their own electrical activity (nerve cells). However, the antiarrhythmic drugs act centrally and peripherally, and the compounds presented in the invention—due to their lipophilicity—mainly within CNS.

The embodiment of such a stated goal and the solution of problems related to the prophylaxis, prevention or/and treatment of diseases or symptoms of neurological background have been achieved in the present invention. It was unexpected that such defined purpose has been achieved with the presented invention.

The subject matter of invention is an aminoalkanol derivative of the formula:

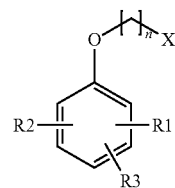

wherein
$R_1$ is $CH_3$, H or Cl,
$R_2$ is $CH_3$, H or Cl,
$R_3$ is $CH_3$, H or Cl,
n is an integral number from 1 to 5, preferably from 1 to 3,
X is

wherein Z is aminoalkanol or

wherein Z is aminoalkanol or amino acid,
with the exception of the compound selected from the group comprising:
2-[(4-methylphenoxy)ethyl]amino-1-butanol,
2-[(4-methylphenoxy)ethyl]amino-1-propanol,
1-[(4-methylphenoxy)ethyl]amino-2-butanol,
1-[(4-methylphenoxy)ethyl]amino-2-propanol,
2-[(4-methylphenoxy)ethyl]amino-2-methyl-1-propanol,
2-[(2,6-dimethylphenoxy)ethyl]amino-1-butanol,
R,S-2-[(2,6-dimethylphenoxy)ethyl]amino-1-propanol,
1-[(2,6-dimethylphenoxy)ethyl]amino-2-butanol,
1-[(2,6-dimethylphenoxy)ethyl]amino-2-propanol,
2-[(2,6-dimethylphenoxy)ethyl]amino-2-methyl-1-propanol.
R,S-2-[(2,6-dimethylphenoxy)ethyl]amino-1-butanol hydrochloride,
R-(−)-2-[(2,6-dimethylphenoxy)ethyl]amino-1-butanol hydrochloride,
S-(+)-2-[(2,6-dimethylphenoxy)ethyl]amino-1-butanol hydrochloride, S-(+)-2N-[(2,6-dimethylphenoxy)ethyl]-2N-methylamino-1-butanol,
R,S-1-[(2,6-dimethylphenoxy)ethyl]amino-2-propanol,
R-(−)-1-[(2,6-dimethylphenoxy)ethyl]amino-2-propanol,
S-(+)-1-[(2,6-dimethylphenoxy)ethyl]amino-2-propanol,
R,S-2-[(4-methylphenoxy)ethyl]amino-1-butanol hydrochloride,
R-(−)-2-[(4-methylphenoxy)ethyl]amino-1-butanol hydrochloride,
S-(+)-2-[(4-methylphenoxy)ethyl]amino-1-butanol hydrochloride,
R,S-2-[(4-methylphenoxy)ethyl]amino-1-propanol hydrochloride,
R,S-2-[(4-methylphenoxy)ethyl]amino-2-methyl-1-propanol hydrochloride,
D,L-trans-2-[(4-methylphenoxy)ethyl]amino-1-cyclohexanol hydrochloride,
R,S-1-[(4-chlor-3-methylphenoxy)acetyl]amino-2-propanol,
R,S-1-[(4-chlor-3-methylphenoxy)acetyl]amino-2-butanol,
R-(+)-2-[(4-chlor-3-methylphenoxy)acetyl]amino-1-butanol,
S-(−)-2-[(4-chlor-3-methylphenoxy)acetyl]amino-1-butanol,
R,S-2-[(4-chlor-3-methylphenoxy)acetyl]amino-1-phenylethanol,
R,S-2-[(2-chlor-5-methylphenoxy)acetyl]amino-1-propanol,
R,S-2-[(2-chlor-5-methylphenoxy)acetyl]amino-1-butanol,
R,S-2-[(2-chlor-5-methylphenoxy)acetyl]amino-2-methyl-1-propanol,
R,S-2-[(4-chlor-3-methylphenoxy)ethyl]amino-1-butanol hydrochloride,
R-(−)-2-[(4-chlor-3-methylphenoxy)ethyl]amino-1-butanol hydrochloride,
S-(+)-2-[(4-chlor-3-methylphenoxy)ethyl]amino-1-butanol hydrochloride,
R,S-1-[(4-chlor-3-methylphenoxy)ethyl]amino-2-butanol hydrochloride,
R,S-2-[(2-chlor-5-methylphenoxy)ethyl]amino-1-propanol,
R,S-2-[(2-chlor-5-methylphenoxy)ethyl]amino-1-butanol,
2-[(2-chlor-5-methylphenoxy)ethyl]amino-2-methyl-1-propanol,
R,S-1-[(4-chlor-2-methylphenoxy)acetyl]amino-2-propanol,
R,S-1-[(4-chlor-2-methylphenoxy)acetyl]amino-2-butanol,
R,S-2-[(4-chlor-2-methylphenoxy)acetyl]amino-1-butanol,
R,S-2-[(4-chlor-2-methylphenoxy)acetyl]amino-1-phenylethanol,
D,L-2N-[(4-chlor-2-methylphenoxy)acetyl]alanine methyl ester,
R,S-1-[(4-chlor-2-methylphenoxy)ethyl]amino-2-propanol,
R,S-2-[(4-chlor-2-methylphenoxy)ethyl]amino-1-propanol,
2-[(4-chlor-2-methylphenoxy)ethyl]amino-2-methyl-1-propanol,
R,S-1-[(4-chlor-2-methylphenoxy)ethyl]amino-2-butanol,
R,S-2-[(4-chlor-2-methylphenoxy)ethyl]amino-1-butanol,
R,S-2-[(4-chlor-2-methylphenoxy)ethyl]amino-1-phenylethanol,
D,L-trans-2-[(4-methylphenoxy)ethyl]amino-1-cyclohexanol,
R,S-2-[(4-methylphenoxy)ethyl]amino-1-propanol hydrochloride,
S-(+)-2-[(2,6-dimethylphenoxy)ethyl]amino-1-propanol hydrochloride,
2-[(2,6-dimethylphenoxy)ethyl]amino-2-methyl-1-propanol hydrochloride,
2-[(4-methylphenoxy)ethyl]amino-2-methyl-1-propanol hydrochloride,
R,S-1-[(4-chlor-3-methylphenoxy)ethyl]amino-2-butanol hydrochloride,
R-(−)-2-[(4-methylphenoxy)ethyl]amino-1-butanol hydrochloride,
S-(+)-2-[(4-methylphenoxy)ethyl]amino-1-butanol hydrochloride,
S-(+)-2N-[(2,6-dimethylphenoxy)ethyl]-2N-methylamino-1-butanol hydrochloride,
S—(+)-1-[(2,6-dimethylphenoxy)ethyl]amino-2-propanol.
Preferably, when X is

Z is aminoalkanol selected from the group comprising:
2-amino-1-ethanol, 3-amino-1-propanol, 4-amino-1-butanol, 5-amino-1-pentanol, 1-amino-2-propanol, 2-amino-1-propanol, 1-amino-2-butanol, 2-amino-1-butanol, 2-amino-1-phenylethanol, 2-amino-2-methyl-1-propanol, 2-amino-2-methyl-1,3-propandiol, 3-methyl-2-amino-1-butanol, 3-methyl-3-amino-1-butanol, D,L-trans-1,2-cyclohexanolamine, trans-1,4-cyclohexanolamine, N-methylaminoethanol, N-ethylaminoethanol, N-methyl-2-amino-1-butanol, N-methyl-2-amino-1-propanol, N-methyl-2-amino-1-phenylethanol, L-treo-2-amino-1-phenyl-1,3-propandiol.
Preferably, when X is

Z is aminoalkanol or amino acid selected from the group comprising:
2-amino-1-ethanol, 3-amino-1-propanol, 4-amino-1-butanol, 5-amino-1-pentanol, 1-amino-2-propanol, 2-amino-1-propanol, 1-amino-2-butanol, 2-amino-1-butanol, 2-amino-1-phenylethanol, 2-amino-2-methyl-1-propanol, 2-amino-2-methyl-1,3-propandiol, 3-methyl-2-amino-1-butanol, 3-methyl-3-amino-1-butanol, D,L-trans-1,2-cyclohexanolamine, trans-1,4-cyclohexanolamine, N-methylaminoethanol, N-ethylaminoethanol, N-methyl-2-amino-1-butanol, N-methyl-2-amino-1-propanol, N-methyl-2-amino-1-phenylethanol, L-treo-2-amino-1-phenyl-1,3-propandiol, glycine or glycinamide or glycine ester, alanine or alaninamide or alanine ester, 2-amino- and 4-aminobutyric acid or appropriate amide or ester.
Preferably, the compound is selected from the group comprising:
R,S-2N-[(2,3-dimethylphenoxy)ethyl]amino-1-propanol (1),
R,S-2N-[(2,3-dimethylphenoxy)ethyl]amino-1-butanol (2),
2N-[(2,3-dimethylphenoxy)ethyl]amino-2-methyl-1-propanol (3),
R,S-2N-[(2,3-dimethylphenoxy)ethyl]amino-1-phenyl ethanol (4),
R,S-1N-[(2,5-dimethylphenoxy)ethyl]amino-2-propanol (5),
R,S-2N-[(2,5-dimethylphenoxy)ethyl]amino-1-propanol (6),
R,S-1N-[(2,5-dimethylphenoxy)ethyl]amino-2-butanol (7),
R,S-2N-[(2,5-dimethylphenoxy)ethyl]amino-1-butanol (8), R,S-2N-[(2,5-dimethylphenoxy)ethyl]amino-1-phenylethanol (9),
R-(−)-1N-[(2,6-dimethylphenoxy)ethyl]amino-2-propanol (10),
R,S-2N-[(2,6-dimethylphenoxy)ethyl]amino-1-propanol (11),
R,S-2N-[(2,6-dimethylphenoxy)ethyl]amino-1-propanol hydrochloride (11a),
R-(−)-2N-[(2,6-dimethylphenoxy)ethyl]amino-1-propanol (12),
R-(−)-2N-[(2,6-dimethylphenoxy)ethyl]amino-1-propanol hydrochloride (12a),
S-(+)-2N-[(2,6-dimethylphenoxy)ethyl]amino-1-propanol (13),
S-(+)-2N-[(2,6-dimethylphenoxy)ethyl]amino-1-propanol hydrochloride (13a),
R,S-2N-[(2,6-dimethylphenoxy)ethyl]-2N-methylamino-1-propanol hydrochloride (14),
3N-[(2,6-dimethylphenoxy)ethyl]amino-3-methyl-1-butanol hydrochloride (15),
L-2N-[(2,6-dimethylphenoxy)ethyl]amino-3-methyl-1-butanol hydrochloride (16),
5N-[(2,6-dimethylphenoxy)ethyl]amino-1-pentanol hydrochloride (17),
D,L-trans-2N-[(2,6-dimethylphenoxy)ethyl]amino-1-cyclohexanol (18),
D,L-trans-2N-[(2,6-dimethylphenoxy)ethyl]amino-1-cyclohexanol hydrochloride (18a),
R,S-2N-[(2,6-dimethylphenoxy)ethyl]amino-1-phenylethanol (19),
R-(−)-2N-[(2,6-dimethylphenoxy)ethyl]amino-1-phenylethanol (20),
S-(+)-2N-[(2,6-dimethylphenoxy)ethyl]amino-1-phenylethanol (21),
R,S-2N-[(2,6-dimethylphenoxy)ethyl]-2N-methylamino-1-phenylethanol hydrochloride (22),
R,S-1N-[(2-chlor-6-methylphenoxy)ethyl]amino-2-propanol (23),
R,S-2N-[(2-chlor-6-methylphenoxy)ethyl]amino-1-propanol (24),
R,S-1N-[(2-chlor-6-methylphenoxy)ethyl]amino-2-butanol (25),
R,S-2N-[(2-chlor-6-methylphenoxy)ethyl]amino-1-butanol (26),
R,S-2N-[(2-chlor-6-methylphenoxy)ethyl]amino-1-butanol hydrochloride (26a),
R-(−)-2N-[(2-chlor-6-methylphenoxy)ethyl]amino-1-butanol (27),
R-(−)-2N-[(2-chlor-6-methylphenoxy)ethyl]amino-1-butanol hydrochloride (27a),
S-(+)-2N-[(2-chlor-6-methylphenoxy)ethyl]amino-1-butanol (28),
S-(+)-2N-[(2-chlor-6-methylphenoxy)ethyl]amino-1-butanol hydrochloride (28a)
2N-[(2-chlor-6-methylphenoxy)ethyl]amino-2-methyl-1,3-propandiol (29),
D,L-trans-2N-[(2-chlor-6-methylphenoxy)ethyl]amino-1-cyclohexanol (30),
R,S-2N-[(2-chlor-6-methylphenoxy)ethyl]amino-1-phenylethanol (31),
R,S-1N-[(4-chlor-2-methylphenoxy)ethyl]amino-2-propanol (32),
R,S-2N-[(4-chlor-2-methylphenoxy)ethyl]amino-1-propanol (33),
R,S-1N-[(4-chlor-2-methylphenoxy)ethyl]amino-2-butanol (34),
R,S-2N-[(4-chlor-2-methylphenoxy)ethyl]amino-1-butanol (35),
2N-[(4-chlor-2-methylphenoxy)ethyl]amino-2-methyl-1-propanol-(36),
R,S-2N-[(4-chlor-2-methylphenoxy)ethyl]amino-1-phenylethanol (37),
R,S-2N-[(2,3,5-trimethylphenoxy)ethyl]amino-1-propanol (38),
R,S-2N-[(2,3,5-trimethylphenoxy)ethyl]amino-1-butanol (39),
R-(+2N-[(2,3,5-trimethylphenoxy)ethyl]amino-1-butanol (40),
S-(+)-2N-[(2,3,5-trimethylphenoxy)ethyl]amino-1-butanol (41),
R,S-2N-[(2,3,5-trimethylphenoxy)ethyl]amino-1-phenylethanol hydrochloride (42),
R-(+2N-[(2,4,6-trimethylphenoxy)ethyl]amino-1-propanol (43),
D,L-trans-2N-[(2,4,6-trimethylphenoxy)ethyl]amino-1-cyclohexanol (44),
R,S-2N-[(2,4,6-trimethylphenoxy)ethyl]amino-1-phenylethanol (45),
R,S-2N-[(2,3-dimethylphenoxy)propyl]amino-1-propanol (46),
2N-[(2,3-dimethylphenoxy)propyl]amino-2-methyl-1-propanol (47),
R,S-2N-[(2,3-dimethylphenoxy)propyl]amino-1-butanol (48),
R,S-2N-[(2,3-dimethylphenoxy)propyl]amino-1-phenylethanol (49),
R,S-1N-[(2,6-dimethylphenoxy)propyl]amino-2-propanol (50),
R,S-2N-[(2,6-dimethylphenoxy)propyl]amino-1-propanol (51),
R-(−)-2N-[(2,6-dimethylphenoxy)propyl]amino-1-propanol hydrochloride (52),
2N-[(2,6-dimethylphenoxy)propyl]amino-2-methyl-1-propanol (53),
R,S-1N-[(2,6-dimethylphenoxy)propyl]amino-2-butanol (54),
R,S-2N-[(2,6-dimethylphenoxy)propyl]amino-1-butanol hydrochloride (55),
R,S-2N-[(2,6-dimethylphenoxy)propyl]amino-1-phenylethanol (56),
R,S-2N-[(2-chlor-6-methylphenoxy)propyl]amino-1-propanol (57),
R,S-2N-[(2-chlor-6-methylphenoxy)propyl]amino-1-butanol hydrochloride (58),
R,S-2N-[(2,6-dimethylphenoxy)acetyl]-2N-methylamino-1-ethanol (59),
R,S-2N-[(2,6-dimethylphenoxy)acetyl]amino-1-propanol (60),
R-(+)-2N-[(2,6-dimethylphenoxy)acetyl]amino-1-propanol (61),
S-(−)-2N-[(2,6-dimethylphenoxy)acetyl]amino-1-propanol (62),
R,S-1N-[(2,6-dimethylphenoxy)acetyl]amino-2-butanol (63),
trans-4N-[(2,6-dimethylphenoxy)acetyl]amino-1-cyclohexanol (64),
D-2N-[(2,6-dimethylphenoxy)acetyl]aminopropionamide (65),
D,L-2N-[(2,6-dimethylphenoxy)acetyl]aminobutyramide (66),
D,L-2N-[(2,6-dimethylphenoxy)acetyl]aminopropionic acid N-methylamide (67), R,S-1N-[(2-chlor-6-methylphenoxy)acetyl]amino-2-propanol (68),
R,S-2N-[(2-chlor-6-methylphenoxy)acetyl]amino-1-propanol (69),
R-(−)-2N-[(2-chlor-6-methylphenoxy)acetyl]amino-1-propanol (70),
S-(+)-2N-[(2-chlor-6-methylphenoxy)acetyl]amino-1-propanol (71),
R,S-1N-[(2-chlor-6-methylphenoxy)acetyl]amino-2-butanol (72),
R,S-2N-[(2-chlor-6-methylphenoxy)acetyl]amino-1-butanol (73),
D,L-N-[(2-chlor-6-methylphenoxy)acetyl]alanine (74),
D-(+)-N-[(2-chlor-6-methylphenoxy)acetyl]alanine (75),
L-(−)-N-[(2-chlor-6-methylphenoxy)acetyl]alanine (76),
D,L-2N-[(2-chlor-6-methylphenoxy)acetyl]aminobutyric acid (77),
D,L-2N-[(2-chlor-6-methylphenoxy)acetyl]aminobutyramide (78),
4N-[(2-chlor-6-methylphenoxy)acetyl]aminobutyric acid (79),
R,S-1N-[(4-chlor-2-methylphenoxy)acetyl]amino-2-propanol (80),
R,S-1N-[(4-chlor-2-methylphenoxy)acetyl]amino-2-butanol (81),
R,S-2N-[(4-chlor-2-methylphenoxy)acetyl]amino-1-phenylethanol (82),
R,S-2N-[(2,4,6-trimethylphenoxy)acetyl]amino-1-phenylethanol (83).

The next subject of invention is a use of the aminoalkanol derivative of the formula:

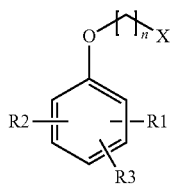

wherein
R1 is CH$_3$, H or Cl,
R2 is CH$_3$, H or Cl,
R2 is CH$_3$, H or Cl,
n is an integral number from 1 to 5, preferably from 1 to 3,
X is

wherein Z is aminoalkanol
or

wherein Z is aminoalkanol or amino acid, with the exception of the compound selected from the group comprising:
2-[(4-methylphenoxy)ethyl]amino-1-butanol,
2-[(4-methylphenoxy)ethyl]amino-1-propanol,
1-[(4-methylphenoxy)ethyl]amino-2-butanol,
1-[(4-methylphenoxy)ethyl]amino-2-propanol,
2-[(4-methylphenoxy)ethyl]amino-2-methyl-1-propanol,
2-[(2,6-dimethylphenoxy)ethyl]amino-1-butanol,
R,S-2-[(2,6-dimethylphenoxy)ethyl]amino-1-propanol,
1-[(2,6-dimethylphenoxy)ethyl]amino-2-butanol,
1-[(2,6-dimethylphenoxy)ethyl]amino-2-propanol,
2-[(2,6-dimethylphenoxy)ethyl]amino-2-methyl-1-propanol
for production of a medicine or prodrug which is used in the prophylaxis, prevention and/or treatment of diseases or symptoms of neurological background.

Preferably the used derivative is a compound according to the compounds described above.

Preferably, the used derivative is a compound selected from:
R-(−)-2-[(2,6-dimethylphenoxy)ethyl]amino-1-propanol,
S-(+)-2-[(2,6-dimethylphenoxy)ethyl]amino-1-propanol,
preferably: R-(−)-2-[(2,6-dimethylphenoxy)ethyl]amino-1-propanol,
R,S-2-[(2-chlor-6-methylphenoxy)ethyl]amino-1-butanol,
R-(−)-2-[(2-chlor-6-methylphenoxy)ethyl]amino-1-butanol,
S-(+)-2-[(2-chlor-6-methylphenoxy)ethyl]amino-1-butanol,
preferably R-(−)-2-[(2-chlor-6-methylphenoxy)ethyl]amino-1-butanol,
R,S-2-[(2,6-dimethylphenoxy)acetyl]amino-1-propanol,
R-(+)-2-[(2,6-dimethylphenoxy)acetyl]amino-1-propanol,
S-(−)-2-[(2,6-dimethylphenoxy)acetyl]amino-1-propanol,
more preferably R-(+)-2-[(2,6-dimethylphenoxy)acetyl]amino-1-propanol.

Preferably, a disease or symptom of neurological background is an epilepsy, especially grand-mal epilepsy, psychomotor epilepsy, focal seizures, status epilepticus, myoclonic seizures or seizures of various origin (sound, light, chemical stimulus, genetic origin, neuronal damage), as well as neuropathic or inflammatory pain.

Preferably, when the produced medicine is an analgesic, anti-inflammatory, anticonvulsant or antiepileptic.

Preferably, when a compound selected from the group comprising:
2-[(4-methylphenoxy)ethyl]amino-1-butanol,
2-[(4-methylphenoxy)ethyl]amino-1-propanol,
1-[(4-methylphenoxy)ethyl]amino-2-butanol,
1-[(4-methylphenoxy)ethyl]amino-2-propanol,
2-[(4-methylphenoxy)ethyl]amino-2-methyl-1-propanol,
2-[(2,6-dimethylphenoxy)ethyl]amino-1-butanol,
R,S-2-[(2,6-dimethylphenoxy)ethyl]amino-1-propanol,
1-[(2,6-dimethylphenoxy)ethyl]amino-2-butanol,
1-[(2,6-dimethylphenoxy)ethyl]amino-2-propanol,
2-[(2,6-dimethylphenoxy)ethyl]amino-2-methyl-1-propanol
is used for production of a medicine or prodrug with anticonvulsant activity, which is used as an anticonvulsant medicine, for treatment of epilepsy-related or not related seizures, for partial and generalized tonic-clonic seizures (grand mal epilepsy), tonic seizures, clonic seizures, myoclonic seizures, for seizures of the origin in the limbic system, psychomotor epilepsy, pharmacoresistant epilepsy or of other origin, as well as relieving neuropathic or inflammatory pain.

Preferably, when a disease or symptom is a neuropathic pain, including pain of various ethiology: diabetic neuropathy, cancer pain, AIDS neuropathy, spinal cord injury, phantom limb pain, or fibromyalgia.

The next subject of invention is a method of obtaining derivatives of aminoalkanols, preferably ((phenoxy)alkyl] aminoalkanols according to claims 1 to 4, characterised in that N-alkylation of said aminoalkanols with appropriate (phenoxy)alkyl bromides is made, by adding 0.010-0.015 mole of appropriate (phenoxy)ethyl or 3-(phenoxy)propyl bromide into a 100 ml flask, then 0.010-0.015 mole of appropriate aminoalkanol and an excess of anh. K$_2$CO$_3$, then the mixture is heated in toluene under reflux for ca. 3-15 h, and left to cool down, afterwards silica gel is added and the mixture is heated again, the gel and precipitated KBr is filtered off and the remaining mixture is distilled into oily residue, then 10-20% HCl and active carbon is added and the mixture is heated, afterwards, the suspension is filtered off and the filtrate is alkalized with 5-20% NaOH in order to precipitate the free basis, which is extracted with benzene or toluene, the organic phase is dried (anh. MgSO₄), and the organic solvent is distilled off until oily residue, which is crystallized.

The next subject of invention is a method of obtaining aminoalkanols, preferably [(phenoxy)acyl]aminoalkanols according to claims 1 to 4, characterised in that N-Acetylation of said aminoalkanols or hydrochloride of amino acids esters with use of chloride of appropriate (phenoxy)alkanoic acid in biphasic environment (toluene/water) with presence of $K_2CO_3$ is made, wherein 0.015-0.025 mole of appropriate aminoalkanol in 30 ml toluene is put in a flask, an excess of $K_2CO_3$ is added dissolved in 50 ml of water, the mixture is cooled down and put on an stirrer, then the mixture is added by small amounts a solution of appropriate (phenoxy)acetic chloride in toluene, and the emulsion is left on the stirrer for ca. 0.5 h and afterwards it is heated, after cooling the organic phase is separated and dried with anh. MgSO₄, then the solvent is distilled off, and the residue is crystallized into a white precipitate of appropriate derivative.

The attached Figures facilitate a better understanding and present the nature of the presented invention.

FIG. 1 presents the scheme of synthesis of [(phenoxy)alkyl]aminoalkanols.

Figure 2:
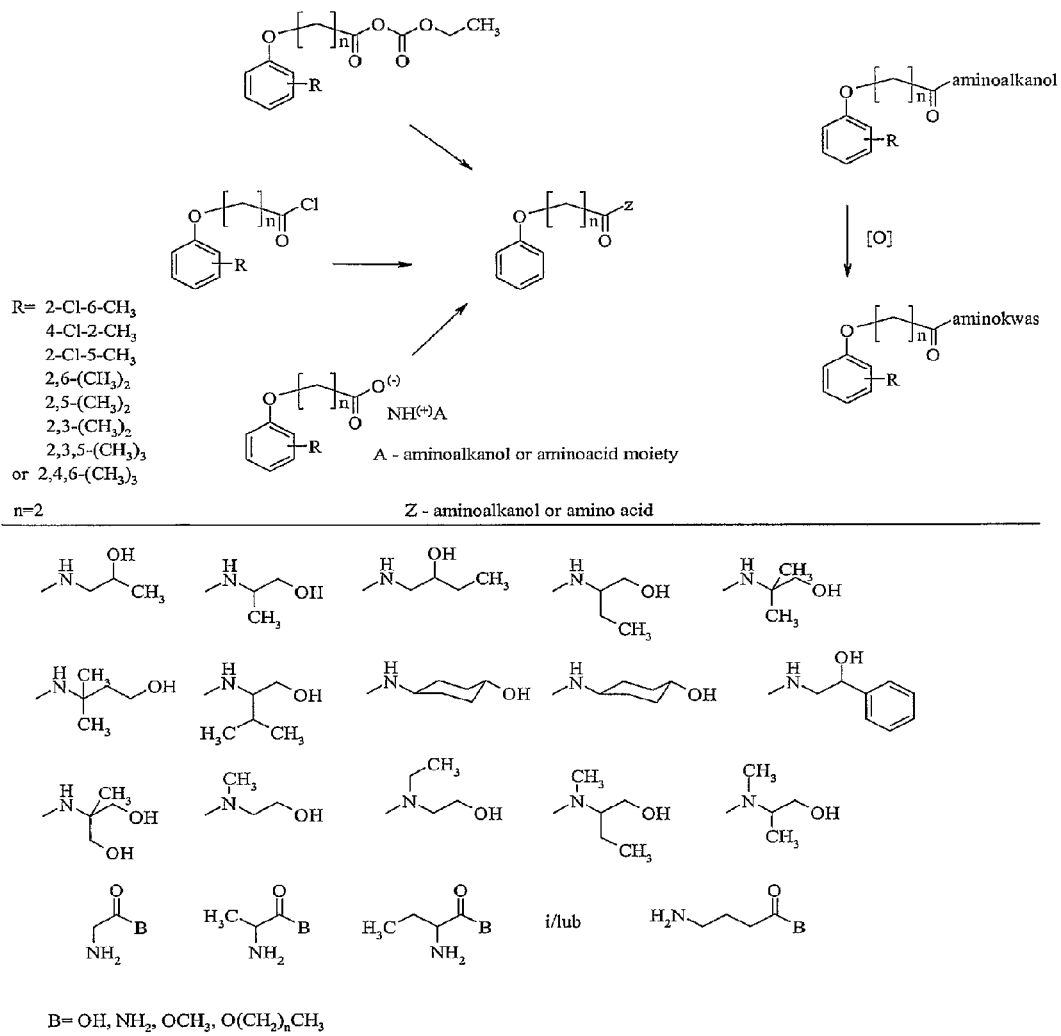

FIG. 2 presents the scheme of synthesis of [(phenoxy)acetyl]aminoalkanols.

Figure 3:
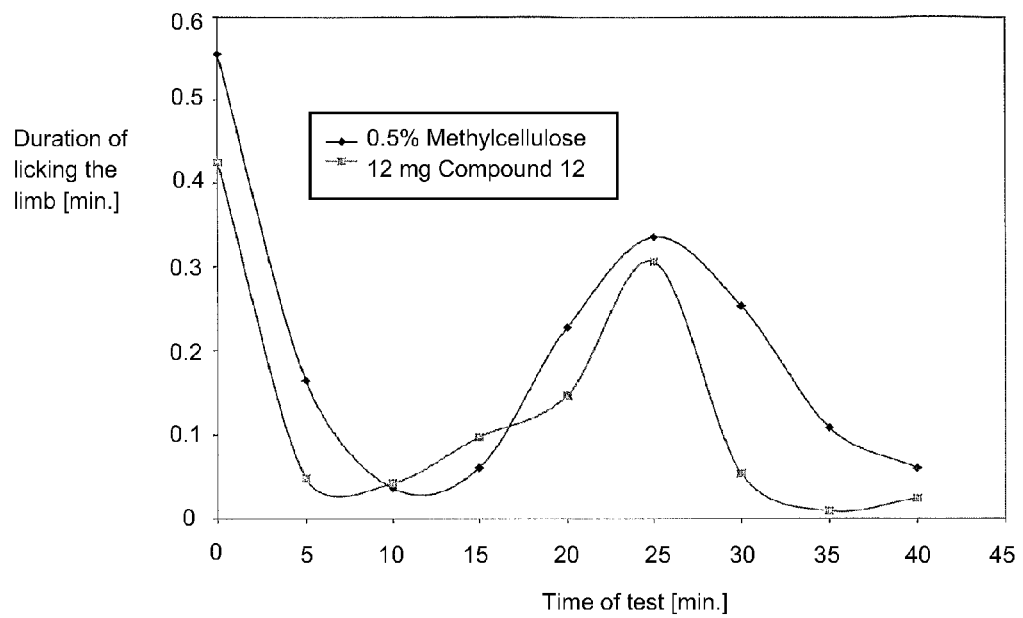

FIG. 3 presents results of formalin test for R-(−)-2-[(2,6-dimethylphenoxy)ethyl]amino-1-propanol.

Figure 4:
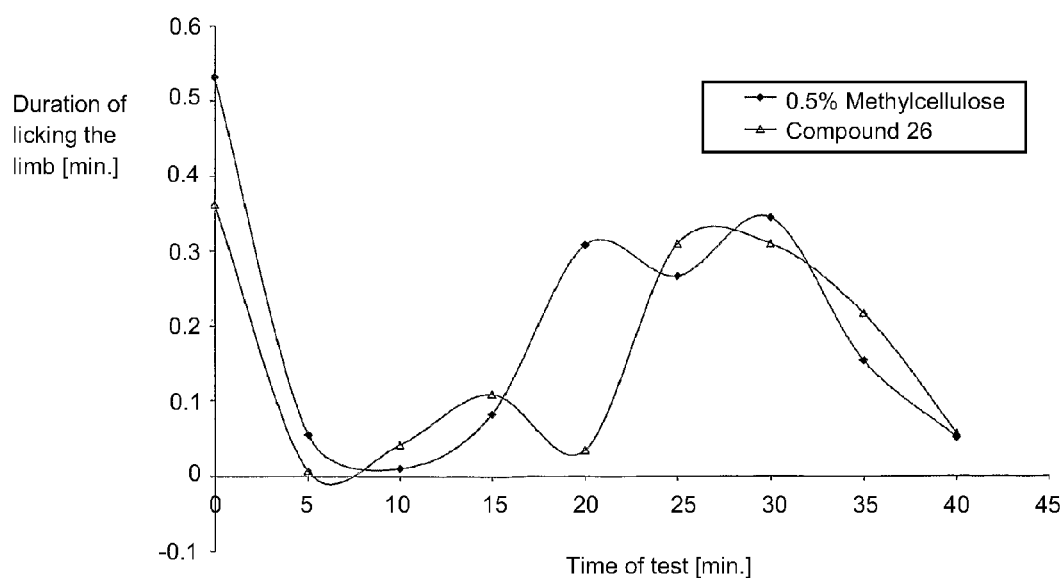

FIG. 4 presents results of formalin test for R,S-2[(2-chlor-6-methylphenoxy)ethyl]amino-1-butanol.

Figure 5:
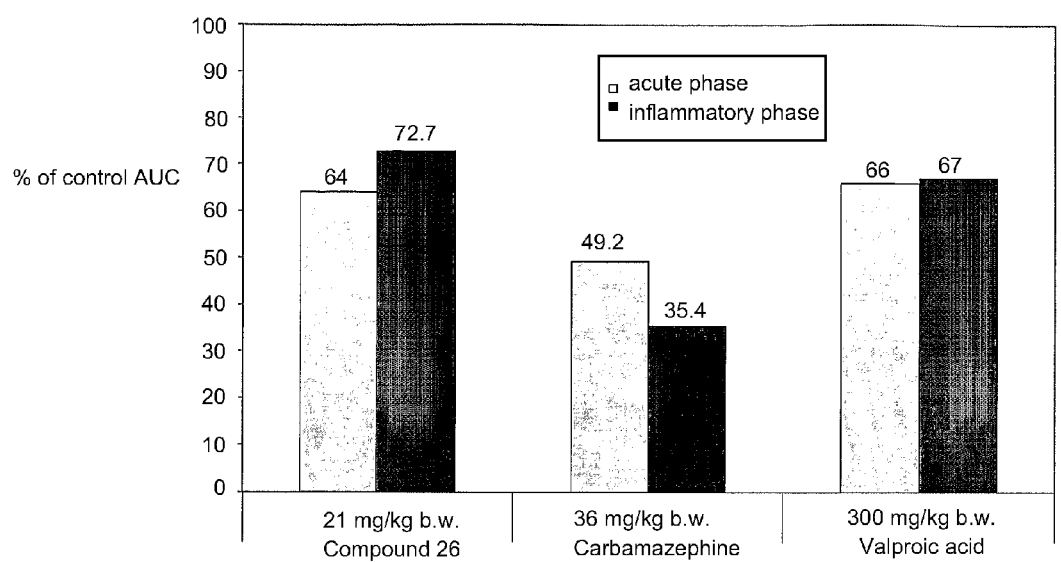

FIG. 5 presents results of comparison of feeling pain by mice after administration of compound 26 and known drugs.

Figure 6:
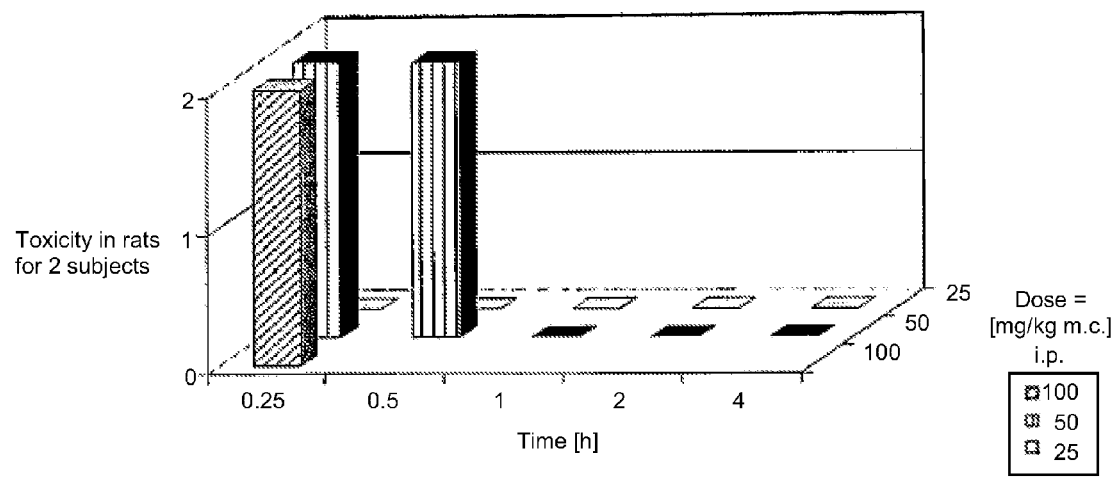

FIG. 6 presents the measurement of the compound 27 dose causing motor impairment.

Below there are example embodiments of the present invention described above.

Example 1

Classification of compounds according to the invention and basic schemes of their synthesis.

New compounds according to the invention are defined with the formula 1 and their pharmaceutically acceptable salts and prodrugs. Generally, the invention is indicated to two subgroups of the aminoalkanol derivatives: substituted [(phenoxy)alkyl]aminalkanols (formula 1) and substituted [(phenoxy)acetyl]aminalkanols (formula 2).

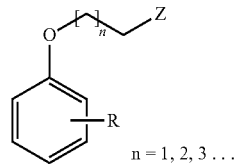

Formula 1 n = 1, 2, 3 ...

| R | Z-aminoalkanol |
|---|---|
| 2,5-(CH₃)₂ | 5-amino-1-pentanol |
| 2,6-(CH₃)₂ | 1-amino-2-propanol |
| 2,3-(CH₃)₂ | 2-amino-1-propanol |

-continued

Formula 1 n = 1, 2, 3 ...

| R | Z-aminoalkanol |
|---|---|
| 2,3,5-(CH₃)₃ | 1-amino-2-butanol |
| 2,4,6-(CH₃)₃ | 2-amino-1-butanol |
| 2-Cl, 6-CH₃ | 2-amino-1-phenylethanol |
| 4-Cl, 2-CH₃ | 2-amino-2-methyl-1-propanol |
| 2-Cl, 5-CH₃ | 2-amino-2-methyl-1,3-propandiol |
|  | 3-methyl-2-amino-1-butanol |
|  | 3-methyl-3-amino-1-butanol |
|  | D,L-trans-1,2-cyclohexanolamine |
|  | N-methyl-2-amino-l-butanol |
|  | N-methyl-2-amino-1-propanol |
|  | N-methyl-2-amino-1-phenylethanol |

Synthesis of [(phenoxy)alkyl]aminoalkanols (FIG. 1)

Synthesis reactions in order to achieve appropriate [(phenoxy)alkyl]aminoalkanols were performed by a few methods, i.e.:

1) aminolysis of toluenesulphonate of appropriate (phenoxy)alkanols [5];

2) N-alkylation of appropriate aminoalkanols using appropriate (phenoxy)alkyl bromides published to pre-final stage which was modified [5];

3) reduction of appropriate [(phenoxy)acetamido]alkanols into appropriate amines using LiAlH₄ in diethyl ether/N₂ [6].

Some compounds were achieved in the form of hydrochlorides, using a saturated solution of HCl in ethanol or using gas HCl, and afterwards performing crystallization from mixture of ethyl acetate/EtOH (3:1).

In order to achieve compounds being racemates or enantiomers, commercially available aminoalkanols were used, except for R,S-1-amino-2-butanol, R-(−) and S-(+)-2-amino-1-butanol, as well as D,L-trans-cyclohexanolamine [7]. Some of the necessary reagents can be achieved according to formerly published procedures [5, 7, 8].

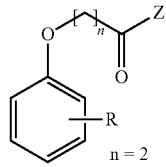

Formula 2 n = 2

| R | Z-aminoalkanol or amino acid: |
|---|---|
| 2,5-(CH₃)₂ | 1-amino-2-propanol |
| 2,6-(CH₃)₂ | 2-amino-1-propanol |
| 2,3-(CH₃)₂ | 1-amino-2-butanol |
| 2,3,5-(CH₃)₃ | 2-amino-1-butanol |
| 2,4,6-(CH₃)₃ | 2-amino-1-phenylethanol |
| 2-Cl, 6-CH₃ | 2-amino-2-methyl-1-propanol |
| 4-Cl, 2-CH₃ | 2-amino-2-methyl-1,3-propandiol |
| 2-Cl, 5-CH₃ | 3-methyl-2-amino-1-butanol |
|  | 3-methyl-3-amino-1-butanol |
|  | trans-1,4-cyclohexanoloamine |
|  | N-methylaminoethanol |
|  | N-methyl-2-amino-1-butanol |

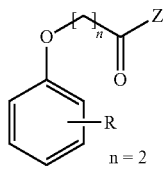

Formula 2

| R | Z-aminoalkanol or amino acid: |
|---|---|
|  | N-methyl-2-amino-1-propanol |
|  | N-methyl-2-amino-1-phenylethanol |
|  | glycine or glycinamide or ester |
|  | alanine or alaninamide or ester |
|  | 2-amino- or 4-aminobutyric acid or |
|  | appropriate amide or ester |

Synthesis of [(phenoxy)acetyl]aminoalkanols or [(phenoxy)acetyl]amino acids and Some of Their Derivatives (FIG. 2)

1) N-Acetylation of appropriate aminoalkanols or hydrochloride of amino acids esters is performed with use of chloride of appropriate (phenoxy)alkanoic acid in biphasic environment (toluene/water) with presence of $K_2CO_3$ [6]. Product of the reaction is achieved by separation of the organic phase, washing with 10% of $NaHCO_3$, drying and evaporation into remaining which is furtherly crystallized from a mixture of n-heptane/toluene (1:2). In case of appropriate esters of amidoacids they were furtherly hydrolysed using 10% $NaHCO_3$, acidified and crystallized (FIG. 2).

Necessary phenoxyalkanoic acids are achieved by O-alkylation of appropriate phenol (as sodium phenolate) with use of appropriate halogenoalkanoic acid in the form of sodium salt. Commercially available acids (in the form of esters) were used.

2) Alternative and convenient method is reaction of mixed anhydrides with use of methyl chloroformate with triethylamine.

3) Another used method of synthesis is azeotropic dehydration of ammonium salt of appropriate (phenoxy)alkanoic acid with appropriate aminoalkanol.

4) Another method, used for achievement of some alkanolamides is synthesis with use of appropriate (phenoxy)alkanoic acid and aminoalkanol with presence of triethylamine and BOP (benzotriazol-1-yloxytris)dimethylaminophosphonium hexafluorophosphate).

5) In order to achieve some (phenoxy)acetyl derivatives of amino acids, a method of oxidation of alcohol group (from earlier achieved [(phenoxy)acetyl]aminoalkanols) was used (FIG. 2).

Example 2

Description of Synthesis of Particular Products 2.1 Synthesis of 2,3-, 2,5-, 2,6-dimethyl-, 2-chlor-6-methyl-, and 4-chlor-2-methyl-, 2,3,5- and (2,4,6-trimethylphenoxy)ethanol or appropriate 3-(phenoxy)-1-propanol Solution of sodium ethanolate was prepared in a 750 ml round-bottomed flask (0.5 mole of sodium was dissolved in ethanol), to which 0.5 mole of appropriate phenol was added. The mixture was heated under reflux and in the boiling point a solution of 2-bromo- or 2-chloroethanol (or 3-chloro-1-propanol) was added drop by drop for ca. 3 h. Afterwards, the mixture was heated for another 2 h and left to cool down. Precipitated white sediment (NaBr or NaCl) was filtered off, and the filtrate was distilled into oily residue. The residue was added 200 ml of water and 10% solution of NaOH (in order to get rid of the remaining phenol). Then extraction with benzene was performed, and organic phase was additionally washed with 10% NaOH, water, and dried with anhydrous $MgSO_4$. After distillation of the solvent, oily residue was achieved. The crude product was used for further bromination.

2.2. Synthesis of 2,3-, 2,5-, 2,6-dimethyl-, 2-chlor-6-methyl-, and 4-chlor-2-methyl-, 2,3,5- and (2,4,6-trimethylphenoxy)alkyl bromides 0.15 mole of appropriate derivative of (phenoxy)ethanol or (phenoxy)propanol was put into a 100 ml round-bottomed flask and 0.05 mole of $PBr_3$ was slowly added. The mixture was heated for 1.5 h under reflux in water bath. Then the mixture was put into a flask with ice and neutralized with 15% $NaHCO_3$, and afterwards extraction with benzene was performed. After drying organic phase (anh. $MgSO_4$), the solvent was distilled off, and oily residue was achieved. The crude product was used for further aminolysis.

2.3 Synthesis of 2,3-, 2,5-, 2,6-dimethyl-, 2-chlor-6-methyl-, and 4-chlor-2-methyl-, 2,3,5- and [(2,4,6-trimethylphenoxy)alkyl]aminoalkanols 0.012 mole of appropriate (phenoxy)ethyl or 3-(phenoxy)propyl bromide was put into a 100 ml round-bottomed flask. Then 0.012 mole of appropriate aminoalkanol and an excess of anh. $K_2CO_3$ were added. The mixture was heated in toluene under reflux for ca. 5 h, and left to cool down. Afterwards silica gel was added and the mixture was heated again. The gel and precipitated KBr was filtered off and the remaining mixture was distilled into oily residue. Then 10% HCl and active carbon was added and the mixture was heated. Afterwards, the suspension was filtered off and the filtrate was alkalized with 10% NaOH in order to precipitate the free basis, which was extracted with benzene. The organic phase was dried (anh. $MgSO_4$), and the organic solvent was distilled off until oily residue, which was crystallized.

2.4 Synthesis of 2,6-dimethyl-, 2,4,6-trimethyl-, 2-chlor-6-methyl-, and (4-chlor-2-methylphenoxy) acetic acid Solution of 0.3 mole NaOH in 250 ml water was prepared in a 750 ml round-bottomed flask. Then 0.3 mole of appropriate phenol was added. Separately, 0.3 mole of chloracetic acid in 300 ml 10% $NaHCO_3$ was prepared in a flask, and the mixture was added to the formerly prepared solution of appropriate sodium phenolate and heated refluxed for 1 h. Then active carbon was added, the mixture was filtered off from the suspension, and after cooling down the filtrate was acidified with 10% HCl. The precipitated acid, after filtering and drying, was crystallized from the mixture of heptane/toluene (1:1), and afterwards white crystal precipitate was achieved.

2.5 Synthesis of 2,6-dimethyl-, 2,4,6-trimethyl-, 2-chlor-6-methyl-, and (4-chlor-2-methylphenoxy) acetic acid chlorides 0.15 mole of appropriate (phenoxy)acetic acid was put into a 500 ml round-bottomed flask and 0.75 mole of $SOCl_2$ (d=1.63 g/cm³) was added, and the mixture was heated under reflux for ca. 30 min. Afterwards, excess of thionyl chloride was distilled off under reduced pressure, and the remaining liquid acid chloride was added toluene until 100 ml and the solution of the crude chloride was used for the reactions with an appropriate aminoalkanol.

2.6 Synthesis of 2,6-dimethyl-, 2,4,6-trimethyl-, 2-chlor-6-methyl-, and (4-chlor-2-methylphenoxy) acetyl]aminoalkanols 0.02 mole of appropriate aminoalkanol in 30 ml toluene was put in an Erlenmeyer flask, an excess of $K_2CO_3$ was added dissolved in 50 ml of water. The mixture was cooled down and put on an electromagnetic stirrer. The mixture was added by small amounts a solution of appropriate (phenoxy) acetic chloride in toluene, and the emulsion was left on the stirrer for ca. 0.5 and afterwards it was heated. After cooling the organic phase was separated and dried with anh. $MgSO_4$. Then the solvent was distilled off, and the residue was crystallized into a white precipitate of appropriate derivative.

Example 3

Physicochemical Data of Some Derivatives According to the Invention

Physicochemical parameters (melting point M.p., $R_f$ for typical eluents, IR and ¹H NMR spectra and/or optical rotation [α]) were measured for some achieved compounds, using standard analytical methods.

R,S-2N-[(2,3-dimethylphenoxy)ethyl]amino-1-propanol (1)

M.p.=76-78° C. (toluene/heptane (1/1)); $R_f$=0.47 ($CH_3OH$); IR (KBr, cm⁻¹) v: 3735, 3649, 3295, 3127, 2964, 2931, 2886, 2833, 2601, 2361, 2116, 1909, 1587, 1461, 1266, 771; ¹H-NMR: (δ ppm) 7.01 (dd, J=7.9, J=7.5, 1H, H-5); 6.77 (d, J=7.9, 1H, H-4); 6.74 (d, J=7.5, 1H, H-6); 4.54 (t, J=5.2, 1H, OH); 4.03-3.97 (m, 1H, CHH—OAr); 3.97-3.91 (m, 1H, CHH—OAr); 3.27-3.24 (m, 1H, CHH—OH); 3.24-3.17 (m, 1H, CHH—OH); 2.97-2.90 (m, 1H, CHH—N); 2.90-2.83 (m, 1H, CHH—N); 2.71-2.62 (m, 1H, CH); 2.20 (s, 3H, $CH_3$—Ar (2)); 2.07 (s, 3H, $CH_3$—Ar (3)); 1.89 (bs, 1H, NH); 0.92 (d, J=6.4, 3H, $CH_3$).

R,S-2N-[(2,3-dimethylphenoxy)ethyl]amino-1-butanol (2)

M.p.=55-56° C. (toluene/heptane (1/1)); $R_f$=0.51 ($CH_3OH$); IR (KBr, cm⁻¹) v: 3295, 3158, 2964, 2931, 2875, 2837, 1900, 1585, 1470, 1263, 1109, 1062, 762; [%]: $N^{calc.}/_{analyzed}$: $5.90/_{5.82}$; $C^{calc.}/_{analyzed}$: $70.86/_{70.76}$; $H^{calc.}/_{analyzed}$: $9.77/_{9.76}$.

2N-[(2,3-dimethylphenoxy)ethyl]amino-2-methyl-1-propanol (3)

M.p.=75-77° C. (toluene/heptane (1/1)); $R_f$=0.44 ($CH_3OH$); IR (KBr, cm⁻¹) v: 3295, 3154, 2986, 2971, 2926, 2877, 2827, 2756, 2557, 2359, 1584, 1464, 1263, 1068, 768; [%]: $N^{calc.}/_{analyzed}$: $5.90/_{5.72}$; $C^{calc.}/_{analyzed}$: $70.85/_{70.70}$; $H^{calc.}/_{analyzed}$: $9.77/_{9.90}$.

R,S-2N-[(2,3-dimethylphenoxy)ethyl]amino-1-phenylethanol (4)

M.p.=118-120° C. (toluene/heptane (1/1)); $R_f$=0.62 ($CH_3OH$); IR (KBr, cm⁻¹) v: 3310, 3064, 3033, 2975, 2921, 2899, 2871, 2836, 2735, 2519, 2364, 1892, 1588, 1453, 1266, 1108, 762; [%]: $N^{calc.}/_{analyzed}$: $4.91/_{4.82}$; $C^{calc.}/_{analyzed}$: $75.75/_{75.83}$; $H^{calc.}/_{analyzed}$: $8.12/_{8.28}$.

R,S-1N-[(2,5-dimethylphenoxy)ethyl]amino-2-propanol (5)

M.p.=64-66° C. (toluene/heptane (1/1)); $R_f$=0.39 ($CH_3OH$/ethyl acetate (1/1)); $R_f$=0.58 ($CH_3OH$); IR (KBr, cm⁻¹) v: 3309, 3140, 2968, 2956, 2921, 2833, 2753, 1511, 1441, 1271, 1152, 1045, 803, 443, 408; ¹H-NMR: (δ ppm) 6.98 (d, J=7.4, 1H, H-3); 6.73 (s, 1H, H-6); 6.63 (d, J=7.4, 1H, H-4); 4.44 (d, J=4.3, 1H, OH); 4.03-3.94 (m, 2H, $CH_2$—O); 3.71-3.64 (m, 1H, HO—CH); 2.88 (t, J=5.5, 2H, O—$CH_2$—$CH_2$—N); 2.54-2.45 (m, 2H, N—$CH_2$); 2.25 (s, 3H, 5-$CH_3$); 2.09 (s, 3H, 2-$CH_3$); 1.85 (bs, 1H, NH); 1.04 (d, J=6.3, 2H, $CH_3$—R); $C_{13}H_{21}NO_2$ (223.31); [%]: $N^{calc.}/_{analyzed}$: $6.27/_{6.21}$; $C^{calc.}/_{analyzed}$: $69.92/_{69.90}$; $H^{calc.}/_{analyzed}$: $9.48/_{9.38}$.

R,S-2N-[(2,5-dimethylphenoxy)ethyl]amino-1-propanol (6)

M.p.=74-76° C. (toluene/heptane (1/1)); $R_f$=0.36 ($CH_3OH$/ethyl acetate (1/1)); IR (KBr, cm⁻¹) v: 3300, 3151, 2970, 2922, 2846, 2601, 1876, 1614, 1444, 1263, 1045, 804; ¹H-NMR: (δ ppm) 6.98 (d, J=7.4, 1H, H-3); 6.73 (s, 1H, H-6); 6.63 (d, J=7.4, 1H, H-4); 4.53 (t, J=5.0, 1H, OH); 4.04-3.98 (m, 1H, O—CHH); 3.98-3.93 (m, 1H, O—CHH); 3.33-3.28 (m, 1H, N—CHH); 3.24-3.18 (m, 1H, N—CHH); 2.96-2.90 (m, 1H, CHHOH); 2.89-2.84 (m, 1H, CHHOH); 2.71-2.64 (m, 1H, CH); 2.25 (s, 3H, 5-$CH_3$); 2.10 (s, 3H, 2-$CH_3$); 1.88 (bs, 1H, NH); 0.92 (d, J=6.3, 3H, R—$CR_3$); $C_{13}H_{21}NO_2$ (223.31); [%]: $N^{calc.}/_{analyzed}$: $6.27/_{6.19}$; $C^{calc.}/_{analyzed}$: $69.92/_{69.90}$; $H^{calc.}/_{analyzed}$: $9.48/_{9.32}$.

R,S-1N-[(2,5-dimethylphenoxy)ethyl]amino-2-butanol (7)

M.p.=63-65° C. (toluene/heptane (1/1)); $R_f$=0.39 ($CH_3OH$/ethyl acetate (1/1)); IR (KBr, cm⁻¹) v: 3267, 3142, 2974, 2964, 2920, 2876, 2847, 2802, 1620, 1587, 1512, 1267, 1131, 800; ¹H-NMR: (δ ppm) 6.97 (d, J=7.4, 1H, H-3); 6.73 (s, 1H, H-6); 6.63 (d, J=7.4, 1H, H-4); 4.41 (bs, 1H, OH); 4.03-3.95 (m, 2H, O—$CH_2$); 3.42 (bs, 1H, CH); 2.88 (t, J=5.5, 2H, O—$CH_2$—$CH_2$—N); 2.57 (dd, J=11.6, J=4.0, 1H, N—CHH); 2.48 (dd, J=11.6, J=4.0, 1H, N—CHH); 1.84 (bs, 1H, NH); 1.45-1.26 (m, 2H, $CH_2$); 0.86 (t, J=7.5, 3H, $CH_3$); $C_{14}H_{23}NO_2$ (237.34). [%]: $N^{calc.}/_{analyzed}$: $5.90/_{5.78}$; $C^{calc.}/_{analyzed}$: $70.85/_{70.80}$; $H^{calc.}/_{analyzed}$: $9.77/_{9.77}$.

R,S-2N-[(2,5-dimethylphenoxy)ethyl]amino-1-butanol (8)

M.p.=66-68° C. (toluene/heptane (1/1)); $R_f$=0.44 ($CH_3OH$/ethyl acetate (1/1)); IR (KBr, cm⁻¹ v: 3296, 3151, 2964, 2927, 2876, 2862, 2826, 2733, 2361, 2342, 1458, 1268, 1065, 801, 470; ¹H-NMR: (δ ppm) 6.98 (d, J=7.4, 1H, H-3); 6.73 (s, 1H, H-6); 6.63 (d, J=7.4, 1H, H-4); 4.40 (t, J=5.4, 1H, OH); 4.03-3.93 (m, 2H, $CH_2$—OH); 3.42-3.22 (m, 2H, C$H_2$—OH); 2.90 (t, J=5.5, 2H, N—$CH_2$); 2.49-2.42 (m, 1H, CH); 2.25 (s, 3H, N—$CH_3$); 2.09 (s, 3H, 2-$CR_3$); 1.76 (bs, 1H, NH); 1.41-1.30 (m, 2H, R—$CH_2$—R); 0.85 (t, J=7.5, 3H, $CH_3$—R); $C_{14}R_{23}NO_2$ (237.34); [%]: $N^{calc.}/_{analyzed}$: $5.90/_{5.74}$; $C^{calc.}/_{analyzed}$: $70.85/_{70.76}$; $H^{calc.}/_{analyzed}$: $9.77/_{9.96}$.

R,S-2N-[(2,5-dimethylphenoxy)ethyl]amino-1-phenylethanol (9)

M.p.=124-126° C. (toluene/heptane (1/1)); $R_f$=0.62 ($CH_3OH$); IR (KBr, cm⁻¹) v: 3308, 3061, 2973, 2921, 2839, 2740, 2360, 2341, 1584, 1439, 1210, 1132, 803, 701; $^1$H-NMR: (δ ppm) 7.39-7.26 (m, 4H, H$_{(Ar)}$); 7.25-7.20 (m, 1H, H(Ar)); 6:98 (d, J=7.4, 1H, H-3); 6.73 (s, 1H, H-6); 6.63 (d, J=7.4, 1H, H-4); 5.26 (d, J=3.5, 1H, OH); 4.68-4.61 (m, 1H, CH); 3.98 (t, J=5.5, 2H, O—CH$_2$); 2.92 (t, J=5.5, 2H, O—CH$_2$—CH$_2$—N); 2.72 (d, J=6.2, 2H, N—CH$_2$—CH); 2.25 (s, 3R, 5-CH$_3$); 2.05 (s, 3H, 2-CH$_3$); 1.89 (bs 1H, N—R); [%]N$^{calc.}$/$_{analyzed}$: $^{4.91}$/$_{4.90}$; C$^{calc.}$/$_{analyzed}$: $^{75.76}$/$_{75.49}$; H$^{calc.}$/$_{analyzed}$: $^{8.12}$/$_{8.05}$.

R-(−)-1N-[(2,6-dimethylphenoxy)ethyl]amino-2-propanol (10)

M.p.=76-77° C. (toluene/heptane (1/1)); C$_{13}$H$_{21}$NO$_2$ (223.32) [%]N$^{calc.}$/$_{analyzed}$: $^{6.27}$/$_{6.01}$; C$^{calc.}$/$_{analyzed}$: $^{69.92}$/$_{69.90}$; H$^{calc.}$/$_{analyzed}$: $^{9.48}$/$_{9.58}$.

R,S-2N-[(2,6-dimethylphenoxy)ethyl]amino-1-propanol (11)

M.p.=66-68° C. (toluene/heptane (1/1)); R$_f$=0.56 (CH$_3$OH/ethyl acetate (1/1)); IR (KBr, cm$^{-1}$ ν: 3291, 3147, 3068, 2982, 2964, 2930, 2843, 2593, 1473, 1201, 1041, 757, 434.

R-(−)-2N-[(2,6-dimethylphenoxy)ethyl]amino-1-propanol (12)

M.p.=84-86° C. (toluene/heptane (1/1)); R$_f$=0.56 (CH$_3$OH/ethyl acetate (1/1)); IR (KBr, cm$^{-1}$ ν: 3291, 3147, 2964, 2930, 2844, 1642, 1473, 1201, 1041, 757; $^1$H NMR (500.13 MHz, DMSO-d$_6$): 7.07-6.96 (m, 2H, H-3(Ar), H-5 (Ar)); 6.96-6.84 (m, 1H, H-4(Ar)); 4.57 (t, J=5.2, 1H, OH); 3.85-3.71 (m, 2H, Ar—O—CH$_2$); 3.33-3.19 (m, 2H, CH$_2$—OH); 2.97-2.80 (m, 2H, CH$_2$N); 2.74-2.61 (m, 1H, CH); 2.22 (s, 6H, Ar(CR$_3$)$_2$); 1.97 (bs, 1H, NH); 0.93 (d, J=6.2, 3H, CH$_3$); C$_{13}$H$_{21}$NO$_2$ (223.31); [%]: N$^{calc.}$/$_{analyzed}$: $^{6.27}$/$_{6.17}$; C$^{calc.}$/$_{analyzed}$: $^{69.9}$/$_{69.9}$; H$^{calc.}$/$_{analyzed}$: $^{9.48}$/$_{9.58}$; (c=1%, CHCl$_3$): [α]$_{589}$$^{24.1}$=−36.6°; [α]$_{546}$$^{22.7}$=−38.0°; ee=100%.

R-(−)-2N-[(2,6-dimethylphenoxy)ethyl]amino-1-propanol hydrochloride (12a)

M.p.=107-109° C., $^1$11 NMR (500.13 MHz, DMSO-d$_6$): 9.10 (bs, 2H, NH$_2^+$); 7.07-7.00 (m, 2H, H-3(Ar), H-5(Ar)); 6.99-6.91 (m, 1H, H-4(Ar)); 5.42 (bs, 1H, OH); 4.07 (t, J=5.8, 2H, Ar—O—CR$_2$); 3.74-3.54 (m, 2H, CH$_2$—OH); 3.36 (t, J=5.8, 2H, CH$_2$—N); 3.37-3.26 (m, 1H, CH); 2.26 (s, 6H, Ar—(CH$_3$)$_2$); 1.28 (d, J=6.7, 3H, CH$_3$); [α]$_{589}$$^{25.0}$=−7.96°; [α]$_{546}$$^{24.0}$=−6.0 (c=2%, CH$_3$OH); C$_{13}$H$_{22}$NO$_2$Cl (259.77): [%]: N$^{calc.}$/$_{analyzed}$: $^{5.39}$/$_{5.36}$; C$^{calc.}$/$_{analyzed}$: $^{60.10}$/$_{60.36}$; H$^{calc.}$/$_{analyzed}$: $^{8.54}$/$_{8.19}$.

S-(+)-2N-[(2,6-dimethylphenoxy)ethyl]amino-1-propanol (13)

M.p.=83-85° C. (toluene/heptane (1/1)); R$_f$=0.56 (CH$_3$OH/ethyl acetate (1/1)); $^1$H NMR (300 MRz, DMSO-d$_6$): 7.04-6.88 (m, 3H, H—Ar); 5.0-4.2 (bb, 1H, OH); 3.78 (t, J=5.5, 2H, Ar—O—CH$_2$); 3.32 (dd, J=5.2, J=10.4, 1H, HCR—OH); 3.23 (dd, J=6.8, J=10.4, 1H, HCH—OH); 2.99-2.72 (m, 2H, CH$_2$N); 2.75-2.58 (m, 1H, CH); 2.28 (s, 6H, Ar(CH$_3$)$_2$); 0.93 (d, J=7.4, 3H, CH$_3$); (c=1%, CHCl$_3$): [α]$_1$)$_D$$^{22.7}$=+37.7°; [α]$_{546}$$^{24.1}$=+35.0°.

S-(+)-2N-[(2,6-dimethylphenoxy)ethyl]amino-1-propanol hydrochloride (13a)

M.p.=107-109° C.; [α]$_{589}$$^{25.1}$=+8.04°, [α]$_{589}$$^{24.0}$=+6.0° (c=2%, CR$_3$OH); C$_{13}$H$_{22}$NO$_2$Cl (259.77).

R,S-2N-[(2,6-dimethylphenoxy)ethyl]-2N-methylamino-1-propanol hydrochloride (14)

M.p.=130-132° C.; R$_f$=0.63 (CH$_3$OH/ethyl acetate (1/1)); IR (KBr, cm$^{-1}$) ν: 3356, 3021, 2967, 2930, 2674, 2647, 2360, 2342, 1475, 1199, 771; $^1$H NMR (300 MHz, DMSO-d$_6$): 11.45 (bs, 1H, NH$^+$); 11.12 (bs, 1H, NH$^+$) 7.04 (d, J=7.5, 2H, H-3, H-5); 6.95 (dd, J=7.5, J=7.5, 1H, H-4); 5.54 (bs, 1H, OH); 5.48 (bs, 1H, OH) 4.26-4.12 (m, 2H, CH$_2$—OH); 4.16-4.08 (m, 1H, CH); 3.72-3.59 (m, 1H, CHH—O); 3.59-3.47 (m, 1H, CHH—O); 3.30-3.00 (m, 2H, CH$_2$—N); 2.96, 2.93 (bs, 3H, CH$_3$—N); 2.26 (s, 6H, (CH$_3$—Ar)$_2$); 1.14 (d, J= 6.3, 3H, CH$_3$—R); C$_{14}$H$_{24}$NO$_2$Cl (273.80); [%]: N$^{calc.}$/$_{analyzed}$: $^{5.11}$/$_{5.01}$; C$^{calc.}$/$_{analyzed}$: $^{61.41}$/$_{61.27}$; H$^{calc.}$/$_{analyzed}$: $^{8.83}$/$_{8.82}$.

3N-[(2,6-dimethylphenoxy)ethyl]amino-3-methyl-1-butanol hydrochloride (15)

M.p.=1.70-172° C.; R$_f$=0.69 (CR$_3$OH/ethyl acetate (1/1)); IR (KBr, cm$^{-1}$ ν: 3379, 2963, 2874, 2822, 2740, 2463, 2360, 2343, 1597, 1584, 1466, 1200, 1044, 770; C$_{15}$H$_{26}$NO$_2$Cl (287.83), [%]: N$^{calc.}$/$_{analyzed}$: $^{4.87}$/$_{4.89}$; C$^{calc.}$/$_{analyzed}$: $^{62.59}$/$_{62.24}$; H$^{calc.}$/$_{analyzed}$: $^{9.20}$/$_{9.01}$.

L-2N-[(2,6-dimethylphenoxy)ethyl]amino-3-methyl-1-butanol hydrochloride (16)

M.p.=162-164° C.; R$_f$=0.75 (CH$_3$OH/ethyl acetate (1/11)).

5N-[(2,6-dimethylphenoxy)ethyl]amino-1-pentanol hydrochloride (17)

M.p.=138-140° C.; C$_{15}$H$_{26}$NO$_2$Cl (287.83).

D,L-trans-2N-[(2,6-dimethylphenoxy)ethyl]amino-1-cyklohexanol (18)

M.p.=88-90° C.; R$_f$=0.52 (CH$_3$OH/benzene (1/5)); $^1$H NMR (500.13 MHz, DMSO-d$_6$): 7.00 (d, 2H, J=7.5, H—Ar); 6.89 (t, J=7.5, 1H, H—Ar); 4.65 (d, J=5.1, 1H, OH); 3.84-3.75 (m, 2H, CH$_2$—O—Ar); 3.17-3.08 (m, 1H, CH—OH); 2.95-2.88 (m, 1H, CHH—N); 2.86-2.78 (m, 1H, CHH—N); 2.36 (bs, 1H, NH); 2.27-2.22 (m, 1H, CR—N); 2.22 (s, 6H, o-Ar:-(CH$_3$)$_2$); 1.96-1.87 (m, 1H, C$_6$H$_{10}$); 1.86-1.75 (m, 1H, C$_6$H$_{10}$); 1.68-1.53 (m, 1H, C$_6$H$_{10}$); 1.27-1.09 (m, 2R, C$_6$H$_{10}$); 1.00-0.87 (m, 3H, C$_6$H$_{10}$); 0.98-0.88 (m, 1H, C$_6$R$_{10}$), C$_{16}$H$_{25}$NO$_2$ (263.38); [%]N$^{calc.}$/$_{analyzed}$: $^{5.32}$/$_{5.34}$; C$^{calc.}$/$_{analyzed}$: $^{72.97}$/$_{72.83}$; H$^{calc.}$/$_{analyzed}$: $^{9.57}$/$_{8.89}$.

D,L-trans-2N-[(2,6-dimethylphenoxy)ethyl]amino-1-cyklohexanol hydrochloride (18a)

M.p.=174-176° C.; R$_f$=0.61 (CH$_3$OH/benzene (1/5)); $^1$HNMR. (500.13 MHz, DMSO-d$_6$): 9.54 (s, 1H, NHH$^+$); 8.75 (s, 1H, NHH$^+$); 7.04 (d, 2H, J=7.5, H—Ar); 6.94 (t, J=7.5, 1H, H—Ar); 5.68 (d, J=5.1, 1H, OH); 4.10 (t, J=5.7, 2H, CH$_2$—O—Ar); 3.68-3.60 (m, 1H, CH—OH); 3.42 (t, J=5.7 2H, CH$_2$—N); 3.00-2.92 (m, 1H, N—C—H); 2.26 (s, 6H, o-Ar—(CH$_3$)$_2$); 2.21-2.15 (m, 1H, C$_6$H$_{10}$); 1.98-1.91 (m, 1H, C$_6$H$_{10}$); 1.76-1.66 (m, 1H, C$_6$H$_{10}$); 1.66-1.59 (m, 1H, $C_6R_{10}$); 1.53-1.41 (m, 3H, $C_6R_{10}$); 1.31-1.13 (m, 3R, $C_6H_{10}$; $C_{16}R_{26}NO_2Cl$ (299.84); [%]: $N^{calc.}/_{analyzed}$: $4.69/_{4.86}$; $C^{calc.}/_{analyzed}$: $64.09/_{63.87}$; $H^{calc.}/_{analyzed}$: $8.74/_{8.47}$.

R,S-2N-[(2,6-dimethylphenoxy)ethyl]amino-1-phenylethanol (19)

M.p.=110-111° C. (toluene/heptane (1/1)); $R_f$=0.62 (CH$_3$OH); $C_{18}H_{23}NO_2$ (285.38);

R-(−)-2N-[(2,6-dimethylphenoxy)ethyl]amino-1-phenylethanol (20)

M.p.=78-80° C. (toluene/heptane (1/1)); $R_f$=0.62 (CH$_3$OH); $C_{18}H_{23}NO_2$ (285.38); (c=1%, CH$_3$OH): $[\alpha]_D^{22.7}$=−23.80°; $[\alpha]_{546}^{24.1}$=+23.0°.

S-(+)-2N-[(2,6-dimethylphenoxy)ethyl]amino-1-phenylethanol (21)

M.p.=78-80° C. (toluene/heptane (1/1)); $R_f$=0.62 (CH$_3$OH); $C_{18}H_{23}NO_2$ (285.38); (c=1%, CH$_3$OH): $[\alpha]_D^{22.7}$=+23.31°; $[\alpha]_{546}^{24.1}$=+22.5°.

R,S-2N-[(2,6-dimethylphenoxy)ethyl]-2N-methylamino-1-phenylethanol hydrochloride (22)

M.p.=130-132° C.; $R_f$=0.69 (CH$_3$OH); IR (K.Br, cm$^{-1}$) ν: 3220, 3019, 2950, 2806, 2718, 1477, 1465, 1363, 1200, 1092, 909, 701; $^1$H NMR (300 MHz, DMSO-d$_6$): 10.45-10.06 (bs, 1H, NH$^+$); 7.49-7.36 (m, 4H, H—Ar); 7.34-7.30 (m, 1H, H—Ar); 7.04 (d, J=7.4; 2H, H-3, H-5); 6.95 (t, J=7.4, 1H, H-4); 6.33-6.28 (bs, 1H, OH); 5.28-5.11 (m, 1H, CH); 4.21-4.10 (m, 2H, O—CH$_2$); 3.80-3.55 (m, 2H, O—CH$_2$—CH$_2$—N); 3.50-3.25 (m, 2H, N—CH$_2$—CH); 3.04 (s, 3H, N—CH$_3$); 2.26 (s, 6H, Ar—(CH$_3$)$_2$); $C_{19}H_{26}NO_2Cl$ (335.87); [%]: $N^{calc.}/_{analyzed}$: $4.17/_{3.99}$; $C^{calc.}/_{analyzed}$: $67.95/_{67.84}$; $H^{calc.}/_{analyzed}$: $7.80/_{7.77}$.

R,S-1N-[(2-chlor-6-methylphenoxy)ethyl]amino-2-propanol (23)

M.p.=72-73° C. (toluene/heptane (1/1)); $R_f$=0.54 (toluene/acetone (1/1)); IR (KBr, cm$^{-1}$) ν: 3300, 3121, 3065, 2960, 2917, 2838, 1464, 1438, 1262, 1227; $^1$H-NMR: (500.13 MRz, 6 ppm, DMSO-d$_6$) 7.28 (ddq, J=8.0, J=1.6, J=0.8 1H, H-3); 7.18 (ddq, J=7.6, J=1.6, J=0.8, 1H, H-5); 7.03 (dd, J=8.0, J=7.6 1H, H-4); 4.44 (d, J=4.5, 1H, OH); 3.92 (t, J=5.6, 2H, O—CH$_2$); 3.68 (dq, J=4.5, J=6.2 1H, C—H); 2.89 (dt, J=1.1, J=5.6, 2H, CH$_2$—N); 2.28 (J=0.8, 3H, CH$_3$—Ar); 1.88 (bs, 1H, NH); $C_{12}H_{18}NO_2Cl$ (243.74); [%]: $N^{calc.}/_{analyzed}$: $5.75/_{5.74}$; $C^{calc.}/_{analyzed}$: $59.14/_{59.08}$; $H^{calc.}/_{analyzed}$: $7.44/_{7.33}$.

R,S-2N-[(2-chlor-6-methylphenoxy)ethyl]amino-1-propanol (24)

M.p.=65-66° C. (toluene/heptane (1/1)); $R_f$=0.50 (toluene/acetone (1/1)); IR (KBr, cm-1) ν: 3284, 3133, 3067, 2983, 2962, 2935, 2844, 2594, 1462, 1441, 1261; $^1$H-NMR: (500.13 MHz, δ ppm, DMSO-d$_6$) 7.28 (ddq, J=7.9, J=1.6, J=0.6 1H, H-3); 7.18 (ddq, J=7.5, J=1.6, J=0.8, 1H, H-5); 7.03 (ddq, J=7.9, J=7.5, J=0.4 1H, H-4); 4.52 (dd, J=5.0, J=5.6 1H, OH); 3.97-3.89 (m 2H, ArO—CR$_2$); 3.30 (ddd, J=10.3, J=5.1, CHH—OR); 3.23 (ddd, J=10.3, J=6.7, J=5.6 1H, CHH—OR); 2.96-2.85 (m, 2H, CH$_2$—NH); 2.71-2.64 (m, 1H, CH); 2.28 (ddd, J=0.6, J=0.8, J=0.4, 3H, Ar—CH$_3$); 1.94 (bs, 1H, NH); 0.93 (d, J=6.3, 3H, CR$_3$—R); $C_{12}H_{18}NO_2Cl$ (243.74) [%]: $N^{calc.}/_{analyzed}$: $5.75/_{5.71}$; $C^{calc.}/_{analyzed}$: $59.14/_{59.05}$; $H^{calc.}/_{analyzed}$: $7.44/_{7.50}$.

R,S-1N-[(2-chlor-6-methylphenoxy)ethyl]amino-2-butanol (25)

M.p.=46-48° C. (toluene/heptane (1/1)); $R_f$=0.62 (toluene/acetone (1/1)); IR (KBr, cm$^{-1}$) ν: 3304, 3178, 2957, 2923, 2836, 2364, 2342, 1458, 1444, 1264, 1226; $^1$H-NMR: (500.13 MRz, DMSO-d$_6$, δ ppm) 7.28 (ddq, J=8.0, J=1.7, J=0.7, 1H, H-3); 7.18 (ddq, J=7.5, J=1.6, J=0.8, 1H, H-5); 7.03 (dd, J=8.0, J=7.5, 1H, H-4); 4.41 (d, J=4.8, 1H, OH); 3.93 (t, J=5.6, 2H, Ar—OCH$_2$); 3.46-3.40 (m, 1H, CH); 2.90 (td, J=5.6, J=1.2, 2H, CH$_2$N); 2.57 (dd, J=11.7, J=4.1, 1H, N—CHH); 2.48 (dd, J=11.7, J=7.6, 1H, C—HH); 2.28 (dd, J=0.7, J=0.8, 3H, CH$_3$—Ar); 1.91 (bs, 1H, NH); 1.47-1.38 (m, 1H, CH$_2$Et); 1.36-1.27 (m, 1H, CH$_2$Et); 0.87 (bs, 1H, NH), $C_{13}H_{20}NO_2Cl$ (257.77), [%]: $N^{calc.}/_{analyzed}$: $5.43/_{5.52}$; $C^{calc.}/_{analyzed}$: $60.58/_{60.63}$; $H^{calc.}/_{analyzed}$: $7.82/_{7.54}$.

R,S-2N-[(2-chlor-6-methylphenoxy)ethyl]amino-1-butanol (26)

M.p.=68-69° C. (toluene/heptane (1/1)); $R_f$=0.56 (toluene/acetone (1/1)); $R_f$=0.45 (CH$_3$OH/ethyl acetate (1/3)); IR (KBr, cm$^{-1}$) ν: 3295, 3126, 3067, 2972, 2933, 2867, 2839, 1462, 1370, 1261, 1220; $^1$H-NMR: (500.13 MRz, DMSO-d$_6$, δ ppm) 7.28 (ddq, J=8.0, J=1.6, J=0.6, 1H, H-3); 7.18 (ddq, J=7.6, J=1.6, J=0.8, 1H, H-5); 7.03 (dd, J=8.0, J=7.6, J=0.4, 1H, H-4); 4.42 (t, J=5.2, 1H, OH); 3.93 (t, J=5.6, 2H, Ar—OCR$_2$); 3.42-3.37 (m, 1H, CHHOH); 3.30-3.25 (m, 1H, CHHOR); 2.96-2.86 (m, 2H, CH$_2$N); 2.49-2.43 (m, 1H, CH); 2.28 (ddd, J=0.6, J=0.8, J=0.4, 3H, CR$_3$—Ar); 1.84 (bs, 1H, NH); 1.40-1.33 (m, 2H, CH$_2$Et); 0.85 (t, J=7.5, 3H, CH$_3$(Et)), $C_{13}H_{20}NO_2Cl$ (257.77), [%]: $N^{calc.}/_{analyzed}$: $5.43/_{5.47}$; $C^{calc.}/_{analyzed}$: $60.58/_{60.59}$; $H^{calc.}/_{analyzed}$: $7.82/_{7.65}$.

R,S-2N-[(2-chlor-6-methylphenoxy)ethyl]amino-1-butanol hydrochloride (26a)

M.p.=108-110° C.; $R_1$=0.68 (CH$_3$OH); $R_1$=0.59 (CH$_3$OH/ethyl acetate (1/1)); $^1$H-NMR: (500.13 MHz, DMSO-d$_6$, δ ppm) 9.16 (bs, 1H, NH$^+$); 8.97 (bs, 1H, H$^+$); 7.32-7.04 (m, 3H, Ar); 5.39 (t, J=5.1, 1H, —O—CH$_2$—CHH—N); 4.20 (t, J=5.9, 2H, —O—CH$_2$—); 3.80-3.73 (m, 1H, —CHH—OH); 3.61-3.57 (m, 1H, CHH—OH); 3.39-3.33 (m, 2H, —O—CH$_2$—CHH—NH+OH); 3.16-3.15 (m, 1H, —CH(C$_2$H$_5$)—CH$_2$OH); 2.31 (s, 3H, CH$_3$Ar); 1.80-1.68 (m, 2H, —CH$_2$—CH$_3$); 0.92 (t, J=7.4, 3H, —CH$_2$—CH$_3$), $C_{13}H_{21}NO_2Cl_2$ (294.22), [%]: $N^{calc.}/_{analyzed}$: $4.76/_{4.72}$; $C^{calc.}/_{analyzed}$: $53.06/_{52.80}$; $H^{calc.}/_{analyzed}$: $7.20/_{7.60}$.

R-(−)-2N-[(2-chlor-6-methylphenoxy)ethyl]amino-1-butanol (27)

M.p.=66-68° C. (toluene/heptane (1/1)); $R_f$=0.56 (toluene/acetone (1/1));

$R_f$=0.45 (CH$_3$OH/ethyl acetate (1/3)); IR (KBr, cm$^{-1}$) ν: 3295, 3126, 3067, 2972, 2933, 2867, 2839, 1462, 1370, 1261, 1220; $^1$H-NMR: (CDCl$_3$, 300 MHz, δ ppm) 7.26-6.92 (m, 3H, Ar); 4.08-3.97 (m, 2H, Ar—O—CH$_2$); 3.66 (dd, J=3.9, J=10.6, 1H, CHH—OH); 3.35 (dd, J=6.2, J=10.6, 1H, C HH—OH); 3.18-3.10 (m, 1H, O—CHH—NH); 2.96-2.85 (m, 1H, O—CH$_2$—CHH—NH); 2.69-2.61 (m, 1H, NH—CH(C$_2$H$_5$)—CH$_2$OH); 2.32 (s, 3H, CH$_3$—Ar); 1.63-1.40 (m, 2H, —CH$_2$CH$_3$); 0.96 (t, J=7.4, 3H, —CH$_2$—CH$_3$);

$C_{13}H_{20}NO_2Cl$ (257.77), [%]: $N^{calc.}/_{analyzed:}$ $^{5.43}/_{5.40}$; $C^{calc.}/_{analyzed:}$ $^{60.58}/_{60.26}$; $H^{calc.}/_{analyzed:}$ $^{7.82}/_{7.77}$; (c=1%, CHCl$_3$): $[α]_{546}^{24.1}$=–22.0°, $[α]_{589}^{22.7}$=–20.94°, ee=100%.

R-(–)-2N-[(2-chlor-6-methylphenoxy)ethyl]amino-1-butanol hydrochloride (27a)

M.p.=113-115° C.; $R_f$=0.60 (CR$_3$OH/ethyl acetate (1/1)); $C_{13}H_{21}NO_2Cl_2$ (294.22), [%]: $N^{calc.}/_{analyzed:}$ $^{4.76}/_{4.75}$; $C^{calc.}/_{analyzed:}$ $^{53.06}/_{52.83}$; $H^{calc.}/_{analyzed:}$ $^{7.20}/_{7.19}$; (c=1%, CH$_3$OH); $[α]_{589}^{23.3}$=–1.6°.

S-(+)-2N-[(2-chlor-6-methylphenoxy)ethyl]amino-1-butanol (28)

M.p.=66-68° C. (toluene/heptane (1/1)); $R_f$=0.56 (toluene/acetone (1/1)); $R_f$=0.45 (CH$_3$OH/ethyl acetate (1/3)); $^1$H-NMR: (DMSO-d$_6$, 500.13 MHz, δ ppm) 7.28 (dd, J=7.9, J=1.7, 1H, H-3(Ar)); 7.18 (dd, J=7.6, J=1.7, 1H, H-5(Ar)); 7.03 (dd, J=7.9, J=7.6, 1H, H-4(Ar)); 4.47 (bs, 1H, OH); 3.93 (t, J=5.7, 2H, Ar—O—CH$_2$); 3.41 (dd, J=4.9, J=10.6, 1H, CHH—OH); 3.28 (dd, J=6.5, J=10.6, 1H, CHH—OH); 2.96-2.87 (m, 2H, —CH$_2$—N); 2.49-2.42 (m, 1H, NH—CH(C$_2$H$_5$)—CH$_2$OH); 2.28 (s, 3H, CH$_3$—Ar); 1.96 (bs, 1H, NH); 1.44-1.31 (m, 2H, —CH$_2$—CH$_3$); 0.86 (t, J=7.6, 3H, —CH$_2$—CH$_3$); (c=1%, CHCl$_3$): $[α]_{546}^{24.1}$=21.00°; $[α]_{589}^{22.7}$=+21.04°, ee=100%.

S-(+)-2N-[(2-chlor-6-methylphenoxy)ethyl]amino-1-butanol hydrochloride (28a)

M.p.=113-115° C.; $R_f$=0.60 (CH$_3$OH/ethyl acetate (1/1)); $^1$H-NMR: (500.13 MHz, DMSO-d$_6$, δ ppm) 8.96 (bs, 1H, NH$_2^+$); 7.32 (dd, J=8, J=1.6, 1H, H-3); 7.22 (dd, J=7.6, J=1.6, 1H, H-5); 7.09 (dd, J=8.0, J=7.6, 1H, R-4); 5.38 (t, J=4.7, 1H, OH); 4.21 (t, J=5.8, 2H, Ar—O—CH$_2$—); 3.78 (ddd, J=12.5, J=4.7, J=3.7, 1H, CHH—OH); 3.63 (ddd, J=12.5, J=5.2, J=4.7, 1H, CHH—OH); 3.41 (t, J=5.8, 2H, —CH$_2$—N); 3.21-3.14 (m, 1H, —CH<); 2.32 (s, 3H, Ar—CH$_3$); 1.82-1.72 (m, 1H, —CHH-Et); 1.72-1.61 (m, 1H, —CHH-Et); 0.94 (t, J=7.5, 3H, CH$_3$(Et)), $C_{13}H_{21}NO_2Cl_2$ (294.22), [%]: $N^{calc.}/_{analyzed:}$ $^{4.76}/_{4.74}$; $C^{calc.}/_{analyzed:}$ $^{53.06}/_{52.97}$; $H^{calc.}/_{analyzed:}$ $^{7.20}/_{7.25}$; (c=1%, CH$_3$OH); $[α]_{589}^{23.3}$=+1.4°.

2N-[(2-chlor-6-methylphenoxy)ethyl]amino-2-methyl-1,3-propandiol (29)

M.p.=83-85° C. (toluene/heptane (1/1)); $R_f$=0.52 (CH$_3$OH/ethyl acetate (1/1)); IR (KBr, cm$^{-1}$ ν: 3307, 2973, 2928, 2876, 2679, 1446, 1227, 1048, 773; $C_{13}H_{20}NO_3Cl$ (273.76), [%]: $N^{calc.}/_{analyzed:}$ $^{5.12}/_{5.12}$; $C^{calc.}/_{analyzed:}$ $^{57.04}/_{57.28}$; $H^{calc.}/_{analyzed:}$ $^{7.36}/_{7.46}$.

D,L-trans-2N-[(2-chlor-6-methylphenoxy)ethyl]amino-1-cyklohexanol (30)

M.p.=73-75° C. (toluene/heptane (1/1)); $R_f$=0.48 (CH$_3$OH); IR (KBr, cm$^{-1}$ ν: 3298, 3135, 2932, 2855, 2365, 1456, 1261, 1219, 1048, 896, 763; $^1$H-NMR: (DMSO-d$_6$, 500.13 MRz, δ ppm) 7.28 (ddd, J=0.7, J=1.6, J=8.0, 1H, H-3); 7.18 (ddd, J=0.8, J=1.6, J=7.6, 1H, H-5); 7.02 (dd, J=7.8, J=7.6, 1H, H-4); 4.57 (d, J=5.1, 1H, OH); 3.96 (ddd, J=4.8, J=9.4, J=14.6, 1H, CHH—O—Ar); 3.91 (ddd, J=4.6, J=9.4, J=12.3, 1H, CHH—O—Ar); 3.16-3.08 (m, 1H, H-1(C$_6$H$_{10}$)); 2.95 (ddd, J=4.6, J=9.4, J=12.3, 1H, CHH—N); 2.86 (ddd, J=7.4, J=12.3, 1H, CHH—N); 2.30 (bs, 1H, NH); 2.28 (s, 3H, CH$_3$—Ar); 2.26-2.20 (m, 1H, CH—NH); 1.94-1.88 (m, 1H, (C$_6$H$_{10}$)); 1.84-1.76 (m, 1H, (C$_6$H$_{10}$)); 1.66-1.54 (m, 2H, (C$_6$H$_{10}$)); 1.25-1.10 (m, 3H, (C$_6$H$_{10}$)); 1.00-0.86 (m, 1H, (C$_6$H$_{10}$)), $C_{15}H_{22}NO_2Cl$ (283.80), $N^{calc.}/_{analyzed:}$ $^{4.94}/_{4.93}$; $C^{calc.}/_{analyzed:}$ $^{63.48}/_{63.48}$; $H^{calc.}/_{analyzed:}$ $^{7.81}/_{7.79}$.

R,S-2N-[(2-chlor-6-methylphenoxy)ethyl]amino-1-phenylethanol (31)

M.p.=98-100° C. (toluene/heptane (1/1)); $R_f$=0.60 (CH$_3$OH); IR (KBr, cm$^{-1}$ ν: 3405, 3308, 3064, 3031, 2937, 2898, 2838, 2737, 2360, 1454, 1261; $^1$H-NMR: (DMSO-d$_6$, 500.13 MHz, δ ppm) 7.42-6.92 (m, 8H, H—Ar); 4.76 (dd, J=3.9, J=8.9, 1H, Ar—CHOH—CH$_2$); 4.07-3.98 (m, 2H, —O—CH$_2$—CH$_2$—NH); 3.17-3.02 (m, 3H, O—CH$_2$—CHH—NH, NH—CH$_2$—CHOH); 2.80 (dd, J=8.7, J=12.1, 1H, O—CH$_2$—CHH—NH); 2.30 (s, 3H, CH$_3$—Ar); 1.40 (bs, 1H, OH), $C_{17}H_{20}NO_2Cl$ (305.81), [%]: $N^{calc.}/_{analyzed:}$ $^{4.58}/_{4.50}$; $C^{calc.}/_{analyzed:}$ $^{66/71}/_{66.59}$; $H^{calc.}/_{analyzed:}$ $^{6.59}/_{6.57}$.

R,S-1N-[(4-chlor-2-methylphenoxy)ethyl]amino-2-propanol (32)

M.p.=74-76° C. (toluene/heptane (1/1)); $R_f$=0.35 (CHCl$_3$/CH$_3$OH (4/1)); IR (KBr, cm$^{-1}$ ν: 3274, 3119, 2964, 2955, 2920, 2849, 1497, 1253, 1190, 1132, 966, 787; $^1$H-NMR: (DMSO-d$_6$, 500.13 MHz, δ ppm) 7.12 (s, 1H, H-3); 7.08 (d, J=8.0, 1H, H-5); 6.72 (d, J=8.7, 1H, H-6); 4.06 (t, J=5.1, 2H, O—CH$_2$—CH$_2$—NH); 3.89-3.79 (m, 1H, c*HOH); 3.15-3.02 (m, 2H, O—CH$_2$—CH$_2$—NH); 2.85 (dd, J=12.1, J=3.1, 1H, NH—CHH—C*HOHCH$_3$); 2.72 (bs, 2H, OH, NH); 2.52 (dd, J=12.2, J=9.6, 1R, NH—CHH—C*HOH); 2.20 (s, 3H, CH$_3$—Ar); 1.16 (d, J=6.2, 3H, CH$_3$), $C_{12}R_{18}NO_2Cl$ (243.74), [% α]: $N^{calc.}/_{analyzed:}$ $^{5.75}/_{5.66}$; $C^{calc.}/_{analyzed:}$ $^{59.14}/_{59.07}$; $H^{calc.}/_{analyzed:}$ $^{7.44}/_{7.82}$.

R,S-2N-[(4-chlor-2-methylphenoxy)ethyl]amino-1-propanol (33)

M.p.=84-86° C. (toluene/heptane (1/1)); $R_f$=0.38 (CHCl$_3$/CH$_3$OH (4/1)); IR (KBr, cm$^{-1}$) ν: 3294, 3158, 2963, 2919, 2839, 2363, 1496, 1458, 1382, 1295, 1246, 1192, 1133, 1044; $^1$H-NMR: (DMSO-d$_6$, 500.13 MHz, δ ppm) 7.10 (s, 1H, H-3); 7.09 (d, J=8.2, 1H, H-5); 6.72 (d, J=8.9, 1H, H-6); 4.06 (t, J=4.6, 2H, O—CH$_2$—CH$_2$—NH); 3.63 (dd, J=10.6, J=3.8, 1H, CHHOH); 3.31 (dd, J=10.8, J=7.1, 1H, CHHOH); 3.13-3.13 (m, 1H, N—CHH); 3.00-2.85 (m, 2H, N—C*H, NCHH) 2.42 (bs, 2H, OH, NH); 2.19 (s, 3H, CH$_3$—Ar); 1.11 (d, J=6.4, 3H, N—C*H—CH$_3$), $C_{12}H_{18}NO_2Cl$ (243.74), [%]: $N^{calc.}/_{analyzed:}$ $^{5.75}/_{5.43}$; $C^{calc.}/_{analyzed:}$ $^{59.14}/_{58.87}$; $H^{calc.}/_{analyzed:}$ $^{7.44}/_{6.89}$.

R,S-1N-[(4-chlor-2-methylphenoxy)ethyl]amino-2-butanol (34)

M.p.=72-74° C. (toluene/heptane (1/1)); $R_f$=0.45 (CHCl$_3$/CH$_3$OH (4/1)); IR (K.Br, cm$^{-1}$) ν: 3272, 3189, 2974, 2930, 2879, 2836, 2797, 2736, 1495, 1483, 1250, 1191, 1136; $^1$H-NMR: (DMSO-d$_6$, 500.13 MRz, δ ppm) 7.11 (s, 1H, H-3); 7.08 (d, J=7.9, 1H, H-5); 6.72 (d, J=8.9, 1H, R-6); 4.05 (t, J=5.13, 2H, O—CH$_2$—CH$_2$—NH); 3.61-3.53 (m, 1H, C*HOH); 3.10-3.00 (m, 2H, O—CH$_2$—CH$_{12}$—NH); 2.83 (dd, J=12.1, J=3.1, 1H, NH—CHH—C*HOHCH$_3$); 2.58 (bs, 2H, OH, NH); 2.52 (dd, J=12.2, J=9.2, 1H, NH—CHH—C*HOH); 2.19 (s, 3H, CH$_3$—Ar); 1.52-1.42 (m, 2H, CH$_2$—CH$_3$); 0.97 (t, J=7.4, 3H, CH$_2$—CH$_3$), $C_{13}H_{20}NO_2Cl$ (257.77), [%]: $N^{calc.}/_{analyzed}$: $^{5.43}/_{5.04}$; $C^{calc.}/_{analyzed}$: $^{60.58}/_{60.34}$; $H^{calc.}/_{analyzed}$: $^{7.82}/_{7.37}$.

R,S-2N-[(4-chlor-2-methylphenoxy)ethyl]amino-1-butanol (35)

M.p.=68-70° C. (toluene/heptane (1/1)); $R_f$ 0.49 ($CHCl_3$/$CH_3OH$ (4/1)); IR (KBr, $cm^{-1}$) v: 3257, 3113, 2971, 2932, 2874, 2846, 2826, 2348, 1493, 1374, 1251; $^1H$-NMR: (DMSO-$d_6$, 500.13 MHz, δ ppm) 7.11 (s, 1H, H-3); 7.08 (d, J=7.4, 1H, H-5); 6.72 (d, J=8.9, 1H, H-6); 4.10-3.99 (m, 2H, O—$CH_2$—$CH_2$—NH); 3.65 (dd, J=10.8, J=3.8, 1H, C$\underline{H}H$—OH); 3.34 (dd, J=10.8, J=6.7, 1H, CH$\underline{H}$OH); 3.17-3.11 (m, 1H, O—$CH_2$—C$\underline{H}H$—NH); 3.01-2.94 (m, 1H, O—$CH_2$—CH$\underline{H}$—NH); 2.70-2.62 (m, 1H, C*H—NH); 2.42 (bs, 2, OH, NH); 2.19 (s, 3H, $CH_3$—Ar); 1.60-1.42 (m, 2H, $CH_2$—$CH_3$); 0.95 (t, J=7.4, 3H, $CH_2$—$CH_3$), $C_{13}H_{20}NO_2Cl$ (257.77), [%]: $N^{calc.}/_{analyzed}$: $^{5.43}/_{5.25}$; $C^{calc.}/_{analyzed}$: $^{60.58}/_{60.46}$; $H^{calc.}/_{analyzed}$: $^{7.82}/_{7.77}$.

2N-[(4-chlor-2-methylphenoxy)ethyl]amino-2-methyl-1-propanol (36)

M.p.=122-123° C. (toluene/heptane (1/1)); $R_f$=0.46 ($CH_3OH$); IR (KBr, $cm^{-1}$ v: 3428, 3273, 3097, 2961, 2932, 2875, 2822, 2759, 1494, 1250, 1072,796; $^1H$-NMR: (DMSO-$d_6$, 500 MHz, δ ppm) 7.10-7.01 (m, 2H, NH, H-3, H-5 Ar); 6.71 (d, J=8.0, 1H, H-6 Ar); 4.03 (t, J=5.3, 2H O—C$\underline{H_2}$—$CH_2$—); 3.33 (s, 2H, $CH_2$—OH); 2.94 (t, J=5.3 2H O—$CH_2$—$CH_2$—); 2.19 (s, 4H, $CH_3$Ar, OH); 1.12 (s, 6H, C($CH_3$)$_2$), $C_{13}H_{20}NO_2Cl$ (257.77), [%]: $N^{calc.}/_{analyzed}$: $^{5.43}/_{5.42}$; $C^{calc.}/_{analyzed}$: $^{60.58}/_{60.69}$; $H^{calc.}/_{analyzed}$: $^{7.82}/_{8.13}$.

R,S-2N-[(4-chlor-2-methylphenoxy)ethyl]amino-1-phenylethanol (37)

M.p.=119-121° C. (toluene/heptane (1/1)); $R_f$=0.56 ($CH_3OH$); IR (KBr, $cm^{-1}$ v: 3313, 3149, 3061, 3034, 2950, 2935, 2920, 2890, 2836, 2361, 2342, 1497, 1257; $^1H$-NMR: (DMSO-$d_6$, 500.13 MHz, δ ppm) 7.37-7.28 (m, 4H, H—Ar); 7.25-7.20 (m, 1H, H—Ar); 7.19 (d, J=2.3, 1H, H-3); 7.16 (dd, J=8.7, J=2.3, 1H, H-5); 6.92 (d, J=8.7, 1H, H-6); 5.29 (bs, 1H, OH); 4.64 (t, J=6.3, 1H, CH—OH); 4.00 (t, J=5.4, 2H, O—CH2); 2.92 (t, J=5.4, 2H, N—$CH_2$); 2.72 (d, J=6.3, 2H, N—$CH_2$—CH); 2.10 (s, 3H, $CH_3$—Ar); 1.90 (bs, 1H, NH), $C_{17}H_{20}NO_2Cl$ (305 80), [%]$N^{calc.}/_{analyzed}$: $^{4.58}/_{4.58}$; $C^{calc.}/_{analyzed}$: $^{66.71}/_{66.99}$; $H^{calc.}/_{analyzed}$: $^{6.59}/_{6.56}$.

R,S-2N-[(2.3.5-trimethylphenoxy)ethyl]amino-1-propanol (38)

M.p.=73-75° C. (toluene/heptane (1/1)); $R_f$=0.25 ($CH_3OH$/benzene (1/5)); $^1H$-NMR ($CDCl_3$): (δ ppm) 6.62 (s, 1H, Ar—H); 6.54 (s, 1H, Ar—H); 4.05-4.02 (m, 2H, Ar—O—$CH_2$); 3.61 (dd, J=4.1, J=10.5, 1H, C$\underline{H}H$OH); 3.27 (dd, J=5.0, J=10.5, 1H, CH$\underline{H}$OH); 3.15-3.11 (m, 1H, C$\underline{H}H$—N); 2.96-2.91 (m, 1H, CH$\underline{H}$—N); 2.88-2.84 (m, 1H, N—CH); 2.28 (s, 3H, Ar—$CH_3$); 2.23 (s, 3H, Ar—$CH_3$); 2.10 (s, 3H, Ar—$CH_3$); 1.10 (d, J=6.5 3H, CH—$CH_3$); 2.50-1.50 (b.b., 2H, NH, OH), $C_{14}H_{23}NO_2$ (237.34), [%]: $N^{calc.}/_{analyzed}$: $^{5.90}/_{5.78}$; $C^{calc.}/_{analyzed}$: $^{70.85}/_{71.13}$; $H^{calc.}/_{analyzed}$: $^{9.77}/_{9.36}$.

R,S-2N-[(2.3.5-trimethylphenoxy)ethyl]amino-1-butanol (39)

M.p.=61-62° C. (toluene/heptane (1/1)); $R_f$=0.63 ($CH_3OH$/ethyl acetate (5/1)); $^1H$-NMR (DMSO-$d_6$, 500.13 MHz): (δ ppm) 6.59 (s, 1H, H-4); 6.56 (s, 1H, H-6); 4.45 (b.b., 1H, OH); 3.95 (t, J=5.3, 2H, Ar—O—$CH_2$); 3.50-3.20 (m, 2H, C$\underline{H_2}$—OH); 2.90 (t, 2H, C$\underline{H_2}$—N); 2.55-2.40 (m, 1H, CH); 2.21 (s, 3H, Ar—$CH_3$); 2.16 (s, 3H, Ar—$CH_3$); 2.02 (s, 3H, Ar—$CH_3$); 1.45-1.3 (m, $CH_2$—$CH_3$); 0.85 (t, J=7.2, 3H, $CH_2$—$CH_3$), $C_{15}H_{25}NO_2$ (251.35), [%]: $N^{calc.}/_{analyzed}$: $^{5.57}/_{5.54}$; $C^{calc.}/_{analyzed}$: $^{71.68}/_{71.30}$; $H^{calc.}/_{analyzed}$: $^{10.03}/_{9.90}$.

R-(−)-2N-[(2.3.5-trimethylphenoxy)ethyl]amino-1-butanol (40)

M.p.=47-49° C. (toluene/heptane (1/1)); $R_f$=0.37 ($CH_3OH$/benzene (1/5)).

S-(+)-2N-[(2.3.5-trimethylphenoxy)ethyl]amino-1-butanol (41)

M.p.=47-49° C. (toluene/heptane (1/1)); $R_f$=0.37 ($CH_3OH$/benzene (1/5));

R,S-2N-[(2.3.5-trimethylphenoxy)ethyl]amino-1-phenylethanol hydrochloride (42)

M.p.=146-148° C. (toluene/heptane (1/1)); $R_f$=0.36 ($CH_3OH$/benzene (1/5)); $^1H$-NMR: (DMSO-$d_6$, 500 MHz, δ ppm) 9.37 (s (b.b.), 2H, $NH_2^+$); 7.48-7.23 (m, 5H, H—Ar); 6.62 (d, J=4.7, 2H, H—Ar); 6.26 (d, J=4.7, 1H, OH); 5.13-5.0 (m, 1H, CH); 4.34-4.19 (m, 2H, O—$CH_2$); 3.40-3.03 (m, 4H, $CH_2$—N); 2.22 (s, 3H, $CH_3$—Ar); 2.15 (s, 3H, $CH_3$—Ar); 2.02 (s, 3H, $CH_3$—Ar), $C_{19}H_{26}NO_2Cl$ (335.87), [%]: $N^{calc.}/_{analyzed}$: $^{4.17}/_{4.02}$; $C^{calc.}/_{analyzed}$: $^{67.94}/_{67.91}$; $H^{calc.}/_{analyzed}$: $^{7.80}/_{7.42}$.

R-(−)-2N-[(2.4.6-trimethylphenoxy)ethyl]amino-1-propanol (43)

M.p.=91-92° C.; $R_f$=0.40 (ethanol/ethyl acetate (1/1)); $C_{14}H_{23}NO_2$ (237.33), [%]: $N^{calc.}/_{analyzed}$: $^{5.90}/_{5.92}$; $C^{calc.}/_{analyzed}$: $^{70.85}/_{71.15}$; $H^{calc.}/_{analyzed}$: $^{9.77}/_{9.86}$ (C=1%, $CHCl_3$): $[α]_{589}^{20.5}$=−34.4°.

D,L-trans-2N-[(2.4.6-trimethylphenoxy)ethyl]amino-1-cyklohexanol (44)

M.p.=90-91° C.; $R_f$=0.55 ($CH_3OH$/benzene (1/5)); $^1H$-NMR: (DMSO-$d_6$, 500.13 MHz, δ ppm) 6.80 (s, 2H, H—Ar); 4.63 (d, J=5.1, 1H, OH); 3.80-3.69 (m, 2H, Ar—O—$CH_2$); 3.15-3.08 (m, 1H, CH—OH); 2.93-2.87 (m, 1H, C$\underline{H}H$—N); 2.84-2.77 (m, 1H, CH$\underline{H}$—N); 2.44 (bs, 1H, NH); 2.26-2.19 (m, 1H, N—CH); 2.17 (s, 6H, o-Ar—($CH_3$)$_2$); 2.17 (s, 3H, p-Ar—$CH_3$); 1.96-1.87 (m, 1H, $C_6H_{10}$); 1.85-1.76 (m, 1H, $C_6H_{10}$); 1.85-1.54 (m, 2H, $C_6H_{10}$); 1.27-1.10 (m, 3H, $C_6H_{10}$); 0.98-0.88 (m, 1H, $C_6H_{10}$), $C_{17}H_{27}NO_2$ (277.41), [%]: $N^{calc.}/_{analyzed}$: $^{5.07}/_{4.95}$; $C^{calc.}/_{analyzed}$: $^{73.58}/_{72.80}$; $H^{calc.}/_{analyzed}$: $^{9.81}/_{9.87}$.

R,S-2N-[(2.4.6-trimethylphenoxy)ethyl]amino-1-phenylethanol (45)

M.p.=90-91° C.; $R_f$=0.58 ($CH_3OH$/benzene (1/5)); $^1H$-NMR: (DMSO-$d_6$, 500.13 MHz, δ ppm) 7.40-7.28 (m, 4H, o.m-H—Ar); 7.26-7.20 (m, 1H, H—Ar); 6.80 (s, 2H, H—Ar); 5.33 (d, J=2.6, 1H, OH); 4.66 (d, J=2.6, 1H, C$\underline{H}$—OH); 3.73 (t, J=5.3, 2H, Ar—O—$CH_2$); 2.84-2.82 (m, 2H, $CH_2$—N); 2.72 (d, J=6.3, 2H, N—$CH_2$); 2.17 (s, 3H, p-Ar—$CH_3$); 2.16 (s, 6H, o-Ar—$CH_3$); 2.11 (bs, 1H, NH); C$_{19}$H$_{25}$NO$_2$ (299.41), [%]: N$^{calc.}$/$_{analyzed}$: $^{4.68}$/$_{4.81}$; C$^{calc.}$/$_{analyzed}$: $^{76.22}$/$_{76.26}$; H$^{calc.}$/$_{analyzed}$: $^{8.42}$/$_{8.65}$.

R,S-2N-[(2,3-dimethylphenoxy)propyl]amino-1-propanol (46)

M.p.=88-90° C.; R$_f$=0.24 (CH$_3$OH); IR (KBr, cm$^{-1}$) ν: 3260, 3110, 2957, 2924, 2824, 2599, 2359, 1593, 1481, 1257, 1091, 768; $^1$H-NMR: (DMSO-d$_6$, 500.13 MHz, δ ppm) 7.00 (dd, J=8.2, J=7.5, 1H, H-5); 6.76 (d, J=8.5, 1H, H-4); 6.73 (d, J=7.5, 1H, H-6); 4.45 (bs, 1H, OH); 3.91 (t, J=6.2, 2H, CH$_2$—OAr); 3.28-3.18 (m, 2H, CH$_2$—OH); 2.80-2.70 (m, 2H, CH$_2$—N); 2.69-2.55 (m, 1H, CH); 2.20 (s, 3H, CH$_3$—Ar(2)); 2.07 (s, 3H, CH$_3$—Ar(3)); 1.87-1.80 (m, 2H, R—CH$_2$—R); 1.56 (bs, 1H, NH); 0.90 (d, J=6.4, 3H, CH$_3$).

2N-[(2,3-dimethylphenoxy)propyl]amino-2-methyl-1-propanol (47)

M.p.=128-130° C.; R$_f$=0.22 (CH$_3$OH); IR (KBr, cm$^{-1}$) ν: 3275, 3074, 2963, 2904, 2870, 2814, 2752, 2718, 2662, 2568, 2349, 2147, 1881, 1584, 1469, 1263, 1089; C$_{15}$H$_{25}$NO$_2$ (251.37) [%]N$^{calc.}$/$_{analyzed}$: $^{5.57}$/$_{5.51}$; C$^{calc.}$/$_{analyzed}$: $^{71.67}$/$_{71.57}$; H$^{calc.}$/$_{analyzed}$: $^{10.02}$/$_{10.07}$.

R,S-2N-[(2,3-dimethylphenoxy)propyl]amino-1-butanol (48)

M.p.=82-84° C.; R$_f$=0.24 (CH$_3$OH); IR (KBr, cm$^{-1}$) ν: 3258, 3100, 2964, 2922, 2863, 2815, 1910, 1584, 1464, 1255, 1096, 768; C$_{15}$H$_{25}$NO$_2$ (251.37) [%]: N$^{calc.}$/$_{analyzed}$: $^{5.57}$/$_{5.53}$; C$^{calc.}$/$_{analyzed}$: $^{71.67}$/$_{671.43}$; H$^{calc.}$/$_{analyzed}$: $^{10.02}$/$_{10.01}$.

R,S-2N-[(2,3-dimethylphenoxy)propyl]amino-1-phenylethanol (49)

M.p.=111-112° C.; R$_f$=0.38 (CH$_3$OH); IR (KBr, cm$^{-1}$) ν: 3333, 3322, 3063, 3030, 2946, 2922, 2895, 2844, 2754, 1953, 1582, 1256, 1102, 703; C$_{19}$H$_{25}$NO$_2$ (299.42) [%]: N$^{calc.}$/$_{analyzed}$: $^{4.68}$/$_{4.63}$; C$^{calc.}$/$_{analyzed}$: $^{76.22}$/$_{76.21}$; H$^{calc.}$/$_{analyzed}$: $^{8.42}$/$_{8.43}$.

R,S-1N-[(2,6-dimethylphenoxy)propyl]amino-2-propanol (50)

M.p.=76-78° C.; R$_f$=0.28 (CH$_3$OH/ethyl acetate (1/1)); C$_{14}$H$_{23}$NO$_2$ (237.34).

R,S-2N-[(2,6-dimethylphenoxy)propyl]amino-1-propanol (51)

M.p.=84-86° C.; R$_f$=0.25 (CH$_3$OH/ethyl acetate (1/1)); IR (KBr, cm$^{-1}$) ν: 3307, 3134, 2972, 2948, 2930, 2876, 2838, 2680, 2361, 2341, 1473, 1207, 1053, 782; C$_{14}$H$_{23}$NO$_2$ (237.34) [%]: N$^{calc.}$/$_{analyzed}$: $^{5.90}$/$_{5.85}$; C$^{calc.}$/$_{analyzed}$: $^{70.85}$/$_{70.87}$; H$^{calc.}$/$_{analyzed}$: $^{9.77}$/$_{9.44}$.

R-(−)-2N-[(2,6-dimethylphenoxy)propyl]amino-1-propanol hydrochloride (52)

M.p.=119-120° C. (toluene/heptane (1/1)); C$_{14}$H$_{24}$NO$_2$Cl (273.80).

2N-[(2,6-dimethylphenoxy)propyl]amino-2-methyl-1-propanol (53)

M.p.=73-75° C. (toluene/heptane (1/1)); R$_f$=0.27 (CH$_3$OH/ethyl acetate (1/1)); IR (KBr, cm$^{-1}$) ν: 3272, 3071, 2988, 2970, 2942, 2902, 2870, 2817, 2757, 1592, 1477, 1210, 1073, 764; C$_{15}$H$_{25}$NO$_2$ (251.37), [%]N$^{calc.}$/$_{analyzed}$: $^{5.57}$/$_{5.44}$; C$^{calc.}$/$_{analyzed}$: $^{71.67}$/$_{71.60}$; H$^{calc.}$/$_{analyzed}$: $^{10.02}$/$_{10.10}$.

R,S-1N-[(2,6-dimethylphenoxy)propyl]amino-2-butanol (54)

M.p.=62-64° C. (toluene/heptane (1/1)); R$_f$=0.26 (CH$_3$OH/ethyl acetate (1/1)); IR (KBr, cm$^{-1}$) ν: 3259, 3122, 2972, 2960, 2917, 2850, 2820, 2776, 2348, 1911, 1594, 1476, 1461, 1204, 1064; $^1$H-NMR: (DMSO-d$_6$, 500.13 MHz, δ ppm) 7.00 (d, J=7.5, 2H, H-3, H-5); 6.88 (dd, J=7.5, J=7.5, 1H, H-4); 4.38 (bs, 1H, OH); 3.77 (t, J=6.2, 2H, CH$_2$—OAr); 3.46-3.37 (m, 1H, CH); 2.78-2.67 (m, 2H, CH$_2$—CH$_2$—N); 2.55 (dd, J=11.4, J=4.4, 1H, NH—CHH—CH); 2.42 (dd, J=11.4, J=7.5, 1H, NH—CHH—CH); 2.21 (s, 6H, CH$_3$—Ar (2.6)); 1.89-1.82 (m, 2H, R—CH$_2$—R); 1.63 (bs, 1H, NH); 1.47-1.37 (m, 1H, CHH(Et)); 1.35-1.25 (m, 1H, CHH(Et)); 0.86 (t, J=7.4, 3H, CH$_3$(Et)), C$_{15}$H$_{25}$NO$_2$ (251.37), [%] N$^{calc.}$/$_{analyzed}$: $^{5.57}$/$_{4552}$; C$^{calc.}$/$_{analyzed}$: $^{71.67}$/$_{71.68}$; H$^{calc.}$/$_{analyzed}$: $^{10.02}$/$_{10.41}$.

R,S-2N-[(2,6-dimethylphenoxy)propyl]amino-1-butanol hydrochloride (55)

M.p.=125-127° C. (toluene/heptane (1/1)); R$_f$=0.26 (CH$_3$OH/ethyl acetate (1/1)); IR (KBr, cm$^{-1}$) ν: 3301, 3020, 2970, 2921, 2845, 2813, 2670, 2504, 2355, 1460, 1202, 761; C$_{15}$H$_{26}$NO$_2$Cl (287.82), [%]: N$^{calc.}$/$_{analyzed}$: $^{4.87}$/$_{4.88}$; C$^{calc.}$/$_{analyzed}$: $^{62.60}$/$_{62.39}$; H$^{calc.}$/$_{analyzed}$: $^{9.10}$/$_{8.94}$.

R,S-2N-[(2,6-dimethylphenoxy)propyl]amino-1-phenylethanol (56)

M.p.=90-92° C. (toluene/heptane (1/1)); R$_f$=0.39 (CH$_3$OH/ethyl acetate (1/1)); IR (KBr, cm$^{-1}$) ν: 3308, 3063, 3031, 2928, 2896, 2837, 2769, 2733, 1454, 1199, 759, 699; C$_{19}$H$_{25}$NO$_2$ (299.42), [%]: N$^{calc.}$/$_{analyzed}$: $^{4.68}$/$_{4.68}$; C$^{calc.}$/$_{analyzed}$: $^{76.21}$/$_{76.64}$; H$^{calc.}$/$_{analyzed}$: $^{8.42}$/$_{8.76}$.

R,S-2N-[(2-chlor-6-methylphenoxy)propyl]amino-1-propanol (57)

M.p.=74-75° C. (toluene/heptane (1/1)); R$_f$0.27 (CH$_3$OH/ethyl acetate (1/1)); IR (K.Br, cm$^{-1}$) ν: 3287, 3109, 2978, 2960, 2937, 2902, 2864, 2842, 1594, 1465, 1265, 1083, 1046, 778; $^1$H-NMR: (DMSO-d$_6$, 500.13 MHz, δ ppm) 7.28 (ddd, J=7.9, J=1.7, J=0.6, 1H, H-3); 7.17 (ddd, J=7.6, J=1.7, J=0.7, 1H, H-5); 7.02 (ddd, J=7.9, J=7.6, J=0.4, 1H, H-4); 4.52 (bs, 1H, OH); 3.92 (t, J=6.3, 2H, Ar—O—CH2); 3.26 (dd, J=10.4, J=5.6, 1H, CHH—OH); 3.24 (dd, J=10.4, J=6.2, 1H, CHH—OH); 2.85-2.54 (m, 3H, C—H+CHH—NH+CHH—NH); 2.28-2.26 (m, 3H, Ar—CH$_3$); 1.88 (M.P., J=6.3, J=6.7, 2H, R—CH$_2$—R); 1.64 (bs, 1H, NH); 0.92 (d, J=6.3, 3H, R—CH$_3$), C$_{13}$H$_{20}$NO$_2$Cl (257.77), [%]: N$^{calc.}$/$_{analyzed}$: $^{5.43}$/$_{5.41}$; C$^{calc.}$/$_{analyzed}$: $^{60.58}$/$_{60.49}$; H$^{calc.}$/$_{analyzed}$: $^{7.82}$/$_{7.73}$.

R,S-2N-[(2-chlor-6-methylphenoxy)propyl]amino-1-butanol hydrochloride (58)

M.p.=116-118° C.; R$_f$=0.36 (CH$_3$OH/ethyl acetate (1/1)); IR (KBr, cm$^{-1}$) ν: 3352, 3035, 2968, 2898, 2848, 1463, 1261, 764; $^1$H-NMR: (DMSO-d$_6$, 500.13 MHz, δ ppm) 9.06 (bs, 2H, NH$_2$$^+$); 7.25-6.92 (m, 3H, H—Ar); 4.62 (bs, 1H, OH); 4.05-4.00 (m, 3H, —CH$_2$—OH, ArO-CH$_2$—); 3.90-3.84 (m, 1H, —CH$_2$—OH); 3.53-3.35 (m, 2H, O—CH$_2$—CH$_2$—C H$_2$—N); 3.14 (bs, 1H, NH—C$\underline{H}$); 2.52-2.43 (m, 2H, O—CH$_2$—CH$_2$—C$\underline{H}_2$—NH); 2.29 (s, 3H, Ar—CH$_3$); 1.91 (m, 2H, —CH—C$\underline{H}_2$—CH$_3$); 1.05 (t, J=7.4, 3H, —CH—CH$_2$—C$\underline{H}_3$), C$_{14}$H$_{23}$NO$_2$Cl$_2$ (308.25), [%]: N$^{calc.}$/$_{analyzed}$: $^{4.54}$/$_{4.55}$; C$^{calc.}$/$_{analyzed}$: $^{54.55}$/$_{54.45}$; H$^{calc.}$/$_{analyzed}$: $^{7.52}$/$_{7.45}$.

R,S-2N-[(2,6-dimethylphenoxy)acetyl]-2N-methylamino-1-ethanol (59)

M.p.=90-91° C.; R$_f$=0.66 (toluene/acetone (5/1)); $^1$H-NMR: (DMSO-d$_6$, 500.13 MHz, δ ppm) 7.05-6.99 (m, 2H, H-3(Ar), H-5(Ar)); 6.96-6.89 (m, 1H, H-4(Ar)); 4.83 (t, J=5.3, 0.6H, OH); 4.64 (t, J=5.5, OAH, OH); 4.53 (s, 1.2H, O—CH$_2$—C=O); 4.45 (s, 0.8H, O—CH$_2$—C=O); 3.56-3.48 (m, 2H, N—CH$_2$); 3.42-3.32 (m, 2H, C$\underline{H}_2$—OH); 3.01 (s, 1.2H, N—CH$_3$); 2.87 (s, 1.8H, N—CH$_3$); 2.22 (s, 2.4H Ar-(CH$_3$)2); 2.21 (s, 3.6H, Ar-(CH$_3$)$_2$); C$_{13}$H$_{19}$NO$_3$ (237.30); [%]: N$^{calc.}$/$_{analyzed}$: $^{5.90}$/$_{5.88}$; C$^{calc.}$/$_{analyzed}$: $^{65.80}$/$_{65.96}$; H$^{calc.}$/$_{analyzed}$: $^{8.07}$/$_{8.02}$.

R,S-2N-[(2,6-dimethylphenoxy)acetyl]amino-1-propanol (60)

M.p.=95-96° C.; R$_f$=0.76 (CH$_3$OH/ethyl acetate (1/1)); C$_{13}$H$_{19}$NO$_3$ (237.30).

R-(+)-2N-[(2,6-dimethylphenoxy)acetyl]amino-1-propanol (61)

M.p.=121-123° C.; R$_f$=0.76 (CH$_3$OH/ethyl acetate (1/1)); C$_{13}$H$_{19}$NO$_3$ (237.30).

S-(-)-2N-[(2,6-dimethylphenoxy)acetyl]amino-1-propanol (62)

M.p.=121-123° C.; R$_f$=0.76 (CH$_3$OH/ethyl acetate (1/1)); C$_{13}$H$_{19}$NO$_3$ (237.30).

R,S-1N-[(2,6-dimethylphenoxy)acetyl]amino-2-butanol (63)

M.p.=96-97° C.; C$_{14}$H$_{21}$NO$_3$ (251.30).

trans-4N-[(2,6-dimethylphenoxy)acetyl]amino-1-cyldohexanol (64)

M.p.=161-162° C.; R$_f$=0.48 (toluene/acetone (5/1)); $^{11}$H-NMR: (DMSO-d$_6$, 500.13 MHz, δ ppm) 7.80 (d, J=8.2, 1H, NH); 7.06-6.97 (m, 2H, H-3(Ar), H-5(Ar)); 6.96-6.90 (m, 1H, H-4(Ar)); 4.49 (d, J=4.4, 1H, OH); 4.16 (s, 2H, O—CH2-C=O); 3.7O-3.57 (m, 1H, CH—OH(C6H10)); 3.43-3.33 (m, 1H, C$\underline{H}$—NH(C$_6$H$_{10}$)); 2.22 (s, 6H, Ar-(CH$_3$)$_2$); 1.92-1.71 (m, 4H, C$_6$H$_{10}$); 1.44-1.16 (m, 4H, C$_6$H$_{10}$); C$_{16}$H$_{23}$NO$_3$ (277.35), [%]: N$^{calc.}$/$_{analyzed}$: $^{5.05}$/$_{5.06}$; C$^{calc.}$/$_{analyzed}$: $^{69.30}$/$_{69.50}$; H$^{calc.}$/$_{analyzed}$: $^{8.36}$/$_{8.35}$.

D-2N-[(2,6-dimethylphenoxy)acetyl]aminopropionamide (65)

M.p.=177-178° C.; R$_f$=0.77 (CH$_3$OH/ethyl acetate (1/1)); IR (KBr, cm$^{-1}$ v: 3351, 3266, 3182, 3076, 2980, 2970, 2927, 2865, 2805, 1666, 1200, 774; C$_{13}$H$_{18}$N$_2$O$_3$ (250.30), [%]: N$^{calc.}$/$_{analyzed}$: $^{11.19}$/$_{11.32}$; C$^{calc.}$/$_{analyzed}$: $^{62.38}$/$_{62.08.99}$; H$^{calc.}$/$_{analyzed}$: $^{7.25}$/$_{7.60}$.

D,L-2N-[(2,6-dimethylphenoxy)acetyl]aminobutyramide (66)

M.p.=182-184° C.; R$_f$=0.71 (CH$_3$OH/ethyl acetate (1/1)); R$_f$=0.88 (CH$_3$OH/ethyl acetate (1/1)); C$_{14}$H$_{20}$N$_2$O$_3$ (264.33), [%]: N$^{calc.}$/$_{analyzed}$: $^{10.64}$/$_{10.51}$; C$^{calc.}$/$_{analyzed}$: $^{63.58}$/$_{63.54}$; H$^{calc.}$/$_{analyzed}$: $^{7.62}$/$_{7.52}$.

N-methylamide of D,L-2N-[(2,6-dimethylphenoxy)acetyl]aminopropionic acid (67)

M.p.=129-131° C.; R$_f$=0.78 (CHCl$_3$/CH$_3$OH (4/1)); IR. (KBr, cm$^{-1}$) v: 3297, 3116, 3041, 2978, 2956, 2923, 2878, 2854, 1651, 1531, 1198, 764; C$_{14}$H$_{20}$N$_2$O$_3$ (264.33), [%]: N$^{calc.}$/$_{analyzed}$: $^{10.60}$/$_{10.53}$; C$^{calc.}$/$_{analyzed}$: $^{63.61}$/$_{62.91}$; H$^{calc.}$/$_{analyzed}$: $^{7.62}$/$_{7.44}$.

R,S-1N-[(2-chlor-6-methylphenoxy)acetyl]amino-2-propanol (68)

M.p.=102-104° C.; R$_f$=0.82 (CH$_3$OH/ethyl acetate (1/1)); IR (KBr, cm$^{-1}$) v: 3425, 3350, 2961, 2920, 2874, 1654, 1542, 1467, 1262, 1044; $^1$H-NMR: (DMSO-d$_6$, 500.13 MHz, δ ppm) 7.38 (bs, 1H, NH); 7.26-6.97 (m, 3H, H—Ar); 4.43 (s, 2H, O—CH$_2$—CO); 4.08-3.98 (m, 1H, —C$\underline{H}$—OH); 3.62-3.54 (m, 1H, NH—CH$\underline{H}$); 3.34-3.25 (m, 1H, NH—C$\underline{H}$H); 2.51 (bs, 1H, OH); 2.31 (s, 3H, CH$_3$—Ar); 1.25 (d, J=6.4, 3H, CH—CH$_3$), C$_{12}$H$_{16}$NO$_3$Cl (257.72), [%]: N$^{calc.}$/$_{analyzed}$: $^{5.43}$/$_{5.12}$; C$^{calc.}$/$_{analyzed}$: $^{55.93}$/$_{56.19}$; H$^{calc.}$/$_{analyzed}$: $^{6.26}$/$_{6.32}$.

R,S-2N-[(2-chlor-6-methylphenoxy)acetyl]amino-1-propanol (69)

M.p.=88-90° C.; R$_f$=0.87 (CH$_3$OH/ethyl acetate (1/1)); IR (KBr, cm$^{-1}$ v: 3407, 3376, 2973, 2927, 2879, 1651, 1556, 1267; $^1$H-NMR: (DMSO-d$_6$, 500.13 MHz, δ ppm) 7.76 (d, J=8.5, 1H, NH); 7.31 (dd, J=8.0, J=1.8, 1H, H-3); 7.21 (dd, J=7.6, J=1.8, 1H, H-5); 7.07 (dd, J=8.0, J=7.6, 1H, H-4); 4.78 (bs, 1H, OH); 4.35 (d, J=14.0, 1H, C$\underline{H}$H—O—Ar); 4.28 (d, J=14.0, 1H, CH$\underline{H}$—O—Ar); 4.04-3.82 (m, 1H, CH); 3.48-3.33 (m, 2H, C$\underline{H}_2$—OH); 2.30 (s, 3H, Ar—CH$_3$); 1.10 (d, J=6.7, 3H, —CH$_3$), C$_{12}$H$_{16}$NO$_3$Cl (257.72), [%]: N$^{calc.}$/$_{analyzed}$: $^{5.43}$/$_{5.35}$; C$^{calc.}$/$_{analyzed}$: $^{55.93}$/$_{56.19}$; H$^{calc.}$/$_{analyzed}$: $^{6.26}$/$_{6.39}$.

R-(-)-2N-[(2-chlor-6-methylphenoxy)acetyl]amino-1-propanol (70)

M.p.=111-113° C.; R$_f$=0.82 (CH$_3$OH/ethyl acetate (1/1)); IR (KBr, cm$^{-1}$) v: 3407, 3295, 2974, 2934, 2875, 1655, 1541 1264; $^1$H-NMR: (DMSO-d$_6$, 500.13 MHz, δ ppm) 7.36-6.98 (m, 4H, NH, H—Ar); 4.41 (s, 2H, —O—CH$_2$—CO); 4.24-4.12 (m, 1H, —C$\underline{H}$—CH$_3$); 3.75 (dd, J=3.6, J=11.0, 1H, C$\underline{H}$H—OH); 3.64 (dd, J=6.2, J=11.0, 1H, CH$\underline{H}$—OH); 2.77 (bs, 1H, OH); 2.31 (s, 3H, CH$_3$—Ar); 1.28 (d, J=6.9, 3H, CH—CH$_3$), C$_{12}$H$_{16}$NO$_3$Cl (257.72), [%]: N$^{calc.}$/$_{analyzed}$: $^{5.43}$/$_{5.38}$; C$^{calc.}$/$_{analyzed}$: $^{55.93}$/$_{56.06}$; H$^{calc.}$/$_{analyzed}$: $^{6.26}$/$_{6.48}$ (c=1%, CH$_3$OH) [α]$_{546}^{19.5}$=3.50°; [α]$_{589}^{19.1}$=3.80°.

S-(+)-2N-[(2-chlor-6-methylphenoxy)acetyl]amino-1-propanol (71)

M.p.=111-113° C.; R$_f$=0.82 (CR$_3$OH/ethyl acetate (1/1)); (c=1%, CH$_3$OH): [α]$_{546}^{19.5}$=+3.50°; [α]$_{589}^{19.1}$=+3.74°.

R,S-1N-[(2-chlor-6-methylphenoxy)acetyl]amino-2-butanol (72)

M.p.=96-97° C.; $R_f$=0.70 (CR$_3$OH/ethyl acetate (1/1)); IR (KBr, cm$^{-1}$) ν: 3421, 3337, 2969, 2921, 2878, 1655, 1541, 1458, 1225, 1045; 1R-NMR: (DMSO-d$_6$, 500.13 MRz, δ ppm) 7.91 (dd, J=6.1, J=5.2, 1R, NH); 7.32 (dd, J=8.0, J=1.5, 1R, R-3); 7.21 (dd, J=7.6, J=1.5, 1R, R-5); 7.08 (dd, J=8.0, J=7.6, 1R, R-4); 4.73 (d, J=5.3, 1R, OR); 4.34 (s, 2, O—CH$_2$—C=O); 3.52-3.45 (m, 1R, CR); 3.26 (ddd, J=13.1, J=6.1, J=4.8, 1R, CHHC); 3.10 (ddd, J=13.1, J=6.9, J=5.2, 1R, CHHC); 2.30 (s, 3H, Ar—CR$_3$); 1.48-1.19 (m, 1R, CHH(Et)); 1.36-1.26 (m, 1R, CHH(Et)); 0.88 (t, J=7.5, 3R, CH$_3$(Et)), C$_{13}$H$_{18}$NO$_3$Cl (271.75), [%]: N$^{calc.}$/$_{analyzed}$: $^{5.15}$/$_{5.24}$; C$^{calc.}$/$_{analyzed}$: $^{57.46}$/$_{58.02}$; H$^{calc.}$/$_{analyzed}$: $^{6.67}$/$_{6.60}$.

R,S-2N-[(2-chlor-6-methylphenoxy)acetyl]amino-1-butanol (73)

M.p.=59-60° C.; $R_f$=0.84 (CH30R/ethyl acetate (1/1)); IR (KBr, cm$^{-1}$) ν: 3278, 3075, 2966, 2934, 2875, 1655, 1547, 1263, 1047; $^1$H-NMR: (DMSO-d$_6$, 500.13 MHz, δ ppm) 7.67 (d, J=8.7, 1R, NH); 7.31 (dd, J=8.2,J-1.7, 1H, H-3); 7.21 (dd, Jc:-7.6, J-1.7, 1R, H5); 7.08 (dd, J=8.0, J=7.6, 1R, H-4); 4.74 (t, J=5.5, 1H, OH); 4.38 (d, J=14.1, 1H, O—CH—HC=O); 4.31 (d, J=14.1, 11-I, O—CHHC=O); 3.80-3.72 (m, 1H, CH); 3.51-3.32 (m, 2H, CH$_2$—OH); 2.30 (s, 3H, Ar—CH$_3$); 1.62 (qdd, J=18.9, J=7.4, J=5.2, 1H, CHH(Et)); 1.43 (qdd, J=18.9, J=8.6, J=7.4, 1H, CHH(Et)); 0.87 (t, J=7.4, 3H, —CH$_3$), C$_{13}$H$_{18}$NO$_3$Cl (271.75), [%]: N$^{calc.}$/$_{analyzed}$: $^{5.15}$/$_{5.15}$; C$^{calc.}$/$_{analyzed}$: $^{57.46}$/$_{57.79}$; H$^{calc.}$/$_{analyzed}$: $^{6.38}$/$_{7.25}$.

D,L-N-[(2-chlor-6-methylphenoxy)acetyl]alanine (74)

M.p.=199-201° C.; $R_f$=0.86 (CH$_3$OH/ethyl acetate (1/1)); IR (KBr, cm$^{-1}$) ν: 3364, 2984, 2923, 2750, 2616, 2544, 1859, 1727, 1631, 1421, 1247, 1221; $^1$H-NMR: (DMSO-d$_6$, 500.13 MHz, δ ppm) 7.50 (bs, 1H, CO—NH); 7.25-6.98 (m, 3H, H—Ar); 4.80-4.70 (m, 1H, NH—CH—CH$_3$); 4.46 (dd, J=14.9, J=20.3, 2H, O—CH$_2$—CO); 2.32 (s, 3H, CH$_3$—Ar); 1.58 (d, J=7.2, 3H, CH—CH$_3$), C$_{12}$H$_{14}$NO$_4$Cl (271.70), [%]: N$^{calc.}$/$_{analyzed}$: $^{5.16}$/$_{5.12}$; C$^{calc.}$/$_{analyzed}$: $^{53.04}$/$_{53.17}$; H$^{calc.}$/$_{analyzed}$: $^{5.09}$/$_{5.37}$.

D-(+)-N-[(2-chlor-6-methylphenoxy)acetyl]alanine (75)

M.p.=186-188° C.; $R_f$=0.53 (CH$_3$OH/ethyl acetate (1/1)); IR (KBr, cm$^{-1}$) ν: 3364, 2984, 2923, 2750, 2616, 2544, 1859, 1727, 1631, 1224; $^1$H-NMR: (DMSO-d$_6$, 500.13 MHz, δ ppm) 7.50 (bs, 1H, CO—NH); 7.25-6.98 (m, 3H, H—Ar); 4.80-4.70 (m, 1H, NH—CH—CH$_3$); 4.46 (dd, J=14.9, J=20.3, 2H, O—CH$_2$—CO); 2.32 (s, 3H, CH$_3$—Ar); 1.58 (d, J=7.2, 3H, CH—CH$_3$) C$_{12}$H$_{14}$NO$_4$Cl (271.70), [%]: N$^{calc.}$/$_{analyzed}$: $^{5.16}$/$_{5.43}$; (c=1%, CH$_3$OH): [α]$_{546}^{19.5=}$+9.40°; [α]$_{589}^{19.1=}$+8.48°.

L-(−)-N-[(2-chlor-6-methylphenoxy)acetyl]alanine (76)

M.p.=186-188° C.; $R_f$=0.53 (CH$_3$OH/ethyl acetate (1/1)); (c=1%, CH$_3$OH): [α]$_{546}^{19.5=}$−9.40°; [α]$_{589}^{19.1=}$−9.10°.

D,L-2N-[(2-chlor-6-methylphenoxy)acetyl]aminobutyric acid (77)

M.p.=172-174° C.; $R_f$=0.62 (CH$_3$OH/ethyl acetate (1/1)); IR (KBr, cm$^{-1}$ ν: 3372, 2978, 2925, 2880, 2747, 2548, 1727, 1633, 1241, 1047, 777; $^1$H-NMR: (DMSO-d$_6$, 500.13 MHz, δ ppm) 8.11 (d, J=7.8, 1H, NH); 7.31 (dd, J=7.8, J=1.7, 1H, H-3); 7.21 (dd, J=7.6, J=1.7, 1H, H-5); 7.08 (dd, J=7.8, J=7.6, 1H, H-4); 4.44 (d, J=14.0, 1H, CHH—O—Ar); 4.37 (d, J=14.0, 1H, CHH—O—Ar); 4.32-4.22 (m, 1H, CH); 2.31 (s, 3H, Ar—CH$_3$); 1.94-1.64 (m, 2H, —CH$_2$—CH$_3$); 0.90 (t, J=7.3, 3H, CH$_2$—CH$_3$), C$_{13}$H$_{16}$NO$_4$Cl (285.73), [%]: N$^{calc.}$/$_{analyzed}$: $^{4.90}$/$_{4.87}$; C$^{calc.}$/$_{analyzed}$: $^{54.65}$/$_{54.70}$; H$^{calc.}$/$_{analyzed}$: $^{5.64}$/$_{5.69}$.

D,L-2N-[(2-chlor-6-methylphenoxy)acetyl]aminobutyramide (78)

M.p.=169-171° C.; $R_f$=0.77 (CH$_3$OH/ethyl acetate (1/3)); IR (KBr, cm$^{-1}$) ν: 3369, 3262, 3194, 3065, 2968, 2930, 2872, 1650, 1428, 1261; $^1$H-NMR: (DMSO-d$_6$, 500.13 MHz; δ ppm) 7.45 (bs, 1H, CO—NH); 7.26-6.98 (m, 3H, H—Ar); 6.15 (bs, 1H, CO—NH$_2$); 5.52 (bs, 1H, CO—NH$_2$); 4.56-4.49 (m, 1H, CO—NH—CH); 4.45 (s, 2H, O—CH$_2$—CO); 2.32 (s, 3H, CH$_3$—Ar); 2.17-1.98 (m, 1H, CHH—CH$_3$); 1.87-1.62 (m, 1H, CHH—CH$_3$); 1.03 (t, J=7.4, 3H, CH$_2$—CH$_3$), C$_{13}$H$_{17}$N$_2$O$_3$Cl (284.75), [%]: N$^{calc.}$/$_{analyzed}$: $^{9.84}$/$_{9.75}$; C$^{calc.}$/$_{analyzed}$: $^{54.83}$/$_{55.01}$; H$^{calc.}$/$_{analyzed}$: $^{6.02}$/$_{6.12}$.

4N-[(2-chlor-6-methylphenoxy)acetyl]aminobutyric acid (79)

M.p.=103-105° C.; $R_f$=0.70 (CH$_3$OH/ethyl acetate (1/1)); IR (KBr, cm$^{-1}$) ν: 3394, 2955, 2925, 2729, 2672, 1730, 1646, 1206, 1038; C$_{13}$H$_{16}$NO$_4$Cl (285.73), [%]: N$^{calc.}$/$_{analyzed}$: $^{4.90}$/$_{4.66}$; C$^{calc.}$/$_{analyzed}$: $^{54.65}$/$_{54.47}$; H$^{calc.}$/$_{analyzed}$: $^{5.64}$/$_{5.63}$.

R,S-1N-[(4-chlor-2-methylphenoxy)acetyl]amino-2-propanol (80)

M.p.=76-78° C.; $R_f$=0.86 (CH$_3$OH); IR (KBr, cm$^{-1}$) ν: 3426, 3330, 2972, 2919, 2875, 1651, 1248, 1192, 1134, 805; $^1$H-NMR: (DMSO-d$_6$, 500.13 MHz, δ ppm) 7.16-7.10 (m, 2H, R-3, H-5 Ar); 6.97 (bs, 1H, NH); 6.69 (d, J=8.5, 1H, H-6 Ar); 4.49 (s, 2H, O—CH$_2$—CO); 4.02-3.92 (m, 1H, NH—CH$_2$—CHOH); 3.60-3.52 (m, 1H, NH—CHH); 3.25-3.16 (m, 1H, NH—CHH); 2.26 (s, 3H, CH$_3$Ar); 2.10 (bs, 1H, OH); 1.21 (d, J=6.4, 3H, CH—CH$_3$), C$_{12}$H$_{16}$NO$_3$Cl (257.72), [%]: N$^{calc.}$/$_{analyzed}$: $^{5.43}$/$_{5.24}$; C$^{calc.}$/$_{analyzed}$: $^{55.93}$/$_{56.03}$; H$^{calc.}$/$_{analyzed}$: $^{6.26}$/$_{6.48}$.

R,S-1N-[(4-chlor-2-methylphenoxy)acetyl]amino-2-butanol (81)

M.p.=78-80° C.; $R_f$=0.88 (CH$_3$OH); IR (KBr, cm$^{-1}$ ν: 3429, 3326, 2963, 2936, 2917, 2878, 1549, 1245, 803; $^1$H-NMR: (DMSO-d$_6$, 500.13 MHz, δ ppm) 7.13-7.08 (m, 2H, H-3, R-5 Ar); 7.01 (bs, 1H, NH); 6.6 (d, J=8.5, 1H, H-6 Ar); 4.45 (s, 2H, O—CH$_2$—CO); 3.70-3.54 (m, 2H, NH—CHH-1-CHOH); 3.24-3.15 (m, 1H, NH—CHH—CHOH); 2.58 (s, 1H, OH); 2.23 (s, 3H, CH$_3$Ar); 1.54-1.44 (m, 2H, —CH$_2$—CH$_3$); 0.95 (d, J=7.5, 3H, CH$_2$—CH$_3$), C$_{13}$H$_{18}$NO$_3$Cl (271.75), [%]: N$^{calc.}$/$_{analyzed}$: $^{5.15}$/$_{5.24}$; C$^{calc.}$/$_{analyzed}$: $^{57.46}$/$_{57.45}$; H$^{calc.}$/$_{analyzed}$: $^{6.68}$/$_{7.01}$.

R,S-2N-[(4-chlor-2-methylphenoxy)acetyl]amino-1-phenylethanol (82)

M.p.=111-112° C.; $R_f$=0.90 (CH$_3$OH); IR (KBr, cm$^{-1}$ v: 3379, 3288, 3084, 3061, 3027, 2989, 2954, 2925, 2866, 1657, 1548, 1491, 1250; $^1$H-NMR: (DMSO-d$_6$, 500.13 MHz, δ ppm) 7.37-7.10 (m, 7H Ar); 6.9 (bs, 1H, CO—NH); 6.3 (d, J=8.5, 1H, H-6 Ar); 4.88-4.84 (m, 1H, CH—OH); 4.43 (s, 2H, O—CH$_2$—CO); 3.83-3.75 (m, 1H, NH—CHH); 3.50-3.43 (m, 1H, NH—CHH); 2.86 (bs, 1H, OH); 2.18 (s, 3H, CH$_3$Ar), C$_{17}$H$_{18}$NO$_3$Cl (319.79), [%]: N$^{calc.}$/$_{analyzed}$: $^{4.38}$/$_{4.36}$; C$^{calc.}$/$_{analyzed}$: $^{63.85}$/$_{64.07}$; H$^{calc.}$/$_{analyzed}$: $^{5.67}$/$_{5.52}$.

R,S-2N-[(2.4.6-trimethylphenoxy)acetyl]amino-1-phenylethanol (83)

M.p.=119-120° C.; $R_f$=0.79 (toluene/acetone (5/1)); $^1$H-NMR: (500.13 MHz, DMSO-d$_6$, δ ppm) 7.87 (t, J=5.6, 1H, NH); 7.41-7.30 (m, 4H, H-2(Ar)', H-3(Ar)', H-5(Ar)', H-6(Ar)'); 7.28-7.21 (m, 1H, H-4(Ar)'); 6.81 (s, 2H, H-3(Ar), H-5(Ar)); 5.52 (d, J=4.4, 1H, OH); 4.77-4.72 (m, 1H, CH); 4.12 (s, 2H, O—CH$_2$—C=O); 3.56-3.48 (m, 2H, N—CH$_2$); 3.47-3.41 (m, 1H, NH—CHH—CH); 3.37-3.29 (m, 1H, NH—CHH—CH); 2.18 (s, 3H, Ar-4-(CH$_3$)); 2.15 (s, 6H, Ar-2,6-(CH$_3$)$_2$, C$_{19}$H$_{23}$NO$_3$ (313.38), [%]: N$^{calc.}$/$_{analyzed}$: $^{4.47}$/$_{4.57}$; C$^{calc.}$/$_{analyzed}$: $^{72.82}$/$_{72.90}$; H$^{calc.}$/$_{analyzed}$: $^{7.39}$/$_{7.41}$.

TABLE 1

[(Phenoxy)ethyl]aminoalkanols

| R | Compound | Z | Configuration | Formula Mol. Mass |
|---|---|---|---|---|
| 2,3-(CH$_3$)$_2$ | 1 | | R,S | C$_{13}$H$_{21}$NO$_2$ 223.31 |
| | 2 | | R,S | C$_{14}$H$_{23}$NO$_2$ 237.34 |
| | 3 | | — | C$_{14}$H$_{23}$NO$_2$ 237.34 |
| | 4 | | R,S | C$_{18}$H$_{23}$NO$_2$ 285.38 |
| 2,5-(CH$_3$)$_2$ | 5 | | R,S | C$_{13}$H$_{21}$NO$_2$ 223.31 |
| | 6 | | R,S | C$_{13}$H$_{21}$NO$_2$ 223.31 |
| | 7 | | R,S | C$_{14}$H$_{23}$NO$_2$ 237.34 |
| | 8 | | R,S | C$_{14}$H$_{23}$NO$_2$ 237.34 |

TABLE 1-continued

[(Phenoxy)ethyl]aminoalkanols

| R | Compound | Z | Configuration | Formula Mol. Mass |
|---|---|---|---|---|
| | 9 | ![structure: CH3-NH-CH2-CH(OH)-C6H5] | R,S | $C_{18}H_{23}NO_2$ 285.38 |
| 2,6-$(CH_3)_2$ | 10 | ![structure: CH3-NH-CH2-CH(OH)-CH3] | R | $C_{13}H_{21}NO_2$ 223.31 |
| | 11 | ![structure: CH3-NH-CH(CH3)-CH2-OH] | R,S | $C_{13}H_{21}NO_2$ 223.31 |
| | 11a | ![structure: CH3-NH-CH(CH3)-CH2-OH x HCl] | R,S | $C_{13}H_{22}NO_2Cl$ 259.77 |
| | 12 | ![structure: CH3-NH-CH(CH3)-CH2-OH] | R | $C_{13}H_{21}NO_2$ 223.31 |
| | 12a | ![structure: CH3-NH-CH(CH3)-CH2-OH x HCl] | R | $C_{13}H_{22}NO_2Cl$ 259.77 |
| | 13 | ![structure: CH3-NH-CH(CH3)-CH2-OH] | S | $C_{13}H_{21}NO_2$ 223.31 |
| | 14 | ![structure: (CH3)2N-CH(CH3)-CH2-OH x HCl] | R,S | $C_{14}H_{24}NO_2Cl$ 273.80 |
| | 15 | ![structure: CH3-NH-C(CH3)2-CH2-CH2-OH x HCl] | — | $C_{15}H_{26}NO_2Cl$ 287.83 |
| | 16 | ![structure: CH3-NH-CH(CH(CH3)2)-CH2-OH x HCl] | L | $C_{15}H_{26}NO_2Cl$ 287.83 |

TABLE 1-continued

[(Phenoxy)ethyl]aminoalkanols

| R | Compound | Z | Configuration | Formula Mol. Mass |
|---|---|---|---|---|
| | 17 | MeNH-(CH2)4-OH × HCl | — | $C_{15}H_{26}NO_2Cl$ 287.83 |
| | 18 | trans-2-(methylamino)cyclohexanol | D,L-trans | $C_{16}H_{25}NO_2$ 263.38 |
| | 19 | PhCH(OH)CH2NHMe | R,S | $C_{18}H_{23}NO_2$ 285.38 |
| | 20 | PhCH(OH)CH2NHMe | R-(−) | $C_{18}H_{23}NO_2$ 285.38 |
| | 21 | PhCH(OH)CH2NHMe | S-(+) | $C_{18}H_{23}NO_2$ 285.38 |
| | 22 | PhCH(OH)CH2N(CH3)2 × HCl | R,S | $C_{19}H_{26}NO_2Cl$ 335.87 |
| 2-Cl-6-CH3 | 23 | MeNHCH2CH(OH)CH3 | R,S | $C_{12}H_{18}NO_2Cl$ 243.74 |
| | 24 | MeNHCH(CH3)CH2OH | R,S | $C_{12}H_{18}NO_2Cl$ 243.74 |
| | 25 | MeNHCH2CH(OH)CH2CH3 | R,S | $C_{13}H_{20}NO_2Cl$ 257.77 |
| | 26 | MeNHCH(CH2CH3)CH2OH | R,S | $C_{13}H_{20}NO_2Cl$ 257.77 |

TABLE 1-continued

[(Phenoxy)ethyl]aminoalkanols

| R | Compound | Z | Configuration | Formula Mol. Mass |
|---|---|---|---|---|
|  | 26a | H-N(CH₃)-CH(CH₃)-CH₂-OH × HCl [-NH-CH(CH₃)-CH₂-OH with CH₃, × HCl] | R,S | $C_{13}H_{21}NO_2Cl_2$ 294.22 |
|  | 27 | -NH-CH(CH₃)-CH₂-CH₃... (methylamino-butanol) | R-(−) | $C_{13}H_{20}NO_2Cl$ 257.77 |
|  | 27a | (same as 27) × HCl | R-(−) | $C_{13}H_{21}NO_2Cl_2$ 294.22 |
|  | 28 | methylamino-butanol | S-(+) | $C_{13}H_{20}NO_2Cl$ 257.77 |
|  | 28a | methylamino-butanol × HCl | S-(+) | $C_{13}H_{21}NO_2Cl_2$ 294.22 |
|  | 29 | -NH-C(CH₃)(CH₂OH)-CH₂-OH | — | $C_{13}H_{20}NO_3Cl$ 273.76 |
|  | 30 | trans-2-(methylamino)cyclohexanol | D,L-trans | $C_{15}H_{22}NO_2Cl$ 283.80 |
|  | 31 | -NH-CH₂-CH(OH)-C₆H₅ | R,S | $C_{17}H_{20}NO_2Cl$ 305.81 |
| 4-Cl-2-CH₃ | 32 | -NH-CH₂-CH(OH)-CH₃ | R,S | $C_{12}H_{18}NO_2Cl$ 243.74 |
|  | 33 | -NH-CH(CH₃)-CH₂-OH | R,S | $C_{12}H_{18}NO_2Cl$ 243.74 |

TABLE 1-continued

[(Phenoxy)ethyl]aminoalkanols

| R | Compound | Z | Configuration | Formula Mol. Mass |
|---|---|---|---|---|
| | 34 | CH₃NH-CH₂-CH(OH)-CH₂-CH₃ | R,S | C₁₃H₂₀NO₂Cl 257.77 |
| | 35 | CH₃NH-CH(CH₃)-CH₂-OH | R,S | C₁₃H₂₀NO₂Cl 257.77 |
| | 36 | CH₃NH-C(CH₃)₂-CH₂-OH | — | C₁₃H₂₀NO₂Cl 257.77 |
| | 37 | CH₃NH-CH₂-CH(OH)-C₆H₅ | R,S | C₁₇H₂₀NO₂Cl 305.80 |
| 2,3,5-(CH₃)₃ | 38 | CH₃NH-CH(CH₃)-CH₂-OH | R,S | C₁₄H₂₃NO₂ 237.34 |
| | 39 | CH₃NH-CH(CH₂CH₃)-CH₂-OH | R,S | C₁₅H₂₅NO₂ 251.37 |
| | 40 | CH₃NH-CH(CH₂CH₃)-CH₂-OH | R-(−) | C₁₅H₂₅NO₂ 251.37 |
| | 41 | CH₃NH-CH(CH₂CH₃)-CH₂-OH | S-(+) | C₁₅H₂₅NO₂ 251.37 |
| | 42 | CH₃NH-CH₂-CH(OH)-C₆H₅ × HCl | R,S | C₁₉H₂₆NO₂Cl 335.87 |
| 2,4,6-(CH₃)₃ | 43 | CH₃NH-CH(CH₃)-CH₂-OH | R | C₁₄H₂₃NO₂ 237.22 |

TABLE 1-continued

[(Phenoxy)ethyl]aminoalkanols

| R | Compound | Z | Configuration | Formula Mol. Mass |
|---|---|---|---|---|
|  | 44 | (N-methyl-trans-4-hydroxycyclohexylamino) | D,L trans | $C_{17}H_{27}NO_2$ 277.41 |
|  | 45 | (1-phenyl-2-methylamino-ethanol; OH, NHMe on CH-Ph-CH2) | R,S | $C_{19}H_{25}NO_2$ 299.41 |

TABLE 2

[(Phenoxy)propyl]aminoalkanols

| R | Compound | Z | Configuration | Formula Mol. Mass |
|---|---|---|---|---|
| 2,3-(CH$_3$)$_2$ | 46 | CH(CH$_3$)CH$_2$OH, NHMe | R,S | $C_{14}H_{23}NO_2$ 237.34 |
|  | 47 | C(CH$_3$)$_2$CH$_2$OH, NHMe | — | $C_{15}H_{25}NO_2$ 251.37 |
|  | 48 | CH(CH$_2$CH$_3$)CH$_2$OH, NHMe | R,S | $C_{15}H_{25}NO_2$ 251.37 |
|  | 49 | CH(Ph)CH(OH), NHMe | R,S | $C_{19}H_{25}NO_2$ 299.42 |
| 2,6-(CH$_3$)$_2$ | 50 | CH$_2$CH(OH)CH$_3$, NHMe | R,S | $C_{14}H_{23}NO_2$ 237.34 |
|  | 51 | CH(CH$_3$)CH$_2$OH, NHMe | R,S | $C_{14}H_{23}NO_2$ 237.34 |
|  | 52 | CH(CH$_3$)CH$_2$OH, NHMe × HCl | R | $C_{14}H_{23}NO_2$ 237.34 |
|  | 53 | C(CH$_3$)$_2$CH$_2$OH, NHMe | — | $C_{15}H_{25}NO_2$ 251.37 |
|  | 54 | CH$_2$CH(OH)CH$_2$CH$_3$, NHMe | R,S | $C_{15}H_{25}NO_2$ 251.36 |
|  | 55 | CH(CH$_2$CH$_3$)CH$_2$OH, NHMe × HCl | R,S | $C_{15}H_{26}NO_2Cl$ 287.82 |
|  | 56 | CH(Ph)CH(OH), NHMe | R,S | $C_{19}H_{25}NO_2$ 299.41 |
| 2-Cl-6-CH$_3$ | 57 | CH(CH$_3$)CH$_2$OH, NHMe | R,S | $C_{13}H_{20}NO_2Cl$ 257.77 |

TABLE 2-continued

[(Phenoxy)propyl]aminoalkanols

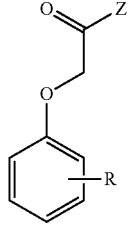

| R | Compound | Z | Configuration | Formula Mol. Mass |
|---|---|---|---|---|
|  | 58 | —NH(CH3)—CH(CH2CH3)—CH2OH · xHCl | R,S | C14H23NO2Cl2 308.25 |

TABLE 3

[(Phenoxy)acetyl]aminoalkanols

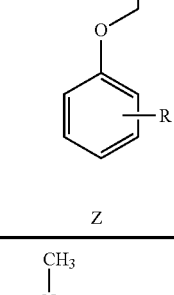

| R | Compound | Z | Configuration | Formula Mol. Mass |
|---|---|---|---|---|
| 2,6-(CH3)2 | 59 | N(CH3)—CH2CH2OH | — | C13H19NO3 237.30 |
|  | 60 | NH(CH3)—CH(CH3)—CH2OH | R,S | C13H19NO3 237.30 |
|  | 61 | NH(CH3)—CH(CH3)—CH2OH | R | C13H19NO3 237.30 |
|  | 62 | NH(CH3)—CH(CH3)—CH2OH | S | C13H19NO3 237.30 |
|  | 63 | NH(CH3)—CH2—CH(OH)—CH2CH3 | R,S | C14H21NO3 251.33 |
|  | 64 | NH-cyclohexyl-OH | trans | C16H23NO3 277.36 |
|  | 65 | NH(CH3)—CH(CH3)—C(O)NH2 | D | C13H18N2O3 250.30 |

TABLE 3-continued

[(Phenoxy)acetyl]aminoalkanols

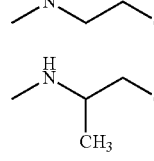

| R | Compound | Z | Configuration | Formula Mol. Mass |
|---|---|---|---|---|
|  | 66 | NH(CH3)—CH(CH2CH3)—C(O)NH2 | D,L | C14H20N2O3 264.32 |
|  | 67 | NH(CH3)—CH(CH3)—C(O)NH(CH3) | D,L | C14H19N2O3 263.32 |
| 2-Cl-6-CH3 | 68 | NH(CH3)—CH2—CH(OH)—CH3 | R,S | C12H16NO3Cl 257.72 |
|  | 69 | NH(CH3)—CH(CH3)—CH2OH | R,S | C12H16NO3Cl 257.72 |
|  | 70 | NH(CH3)—CH(CH3)—CH2OH | R | C12H16NO3Cl 257.72 |
|  | 71 | NH(CH3)—CH(CH3)—CH2OH | S | C12H16NO3Cl 257.72 |
|  | 72 | NH(CH3)—CH2—CH(OH)—CH2CH3 | R,S | C13H18NO3Cl 271.75 |
|  | 73 | NH(CH3)—CH(CH2CH3)—CH2OH | R,S | C13H18NO3Cl 271.75 |
|  | 74 | NH(CH3)—CH(CH3)—COOH | D,L | C12H14NO4Cl 271.70 |
|  | 75 | NH(CH3)—CH(CH3)—COOH | D | C12H14NO4Cl 271.70 |

TABLE 3-continued

[(Phenoxy)acetyl]aminoalkanols

| R | Compound | Z | Configuration | Formula Mol. Mass |
|---|---|---|---|---|
| | 76 | -NH(CH₃)-CH(CH₃)-COOH | L | $C_{12}H_{14}NO_4Cl$ 271.70 |
| | 77 | -NH(CH₃)-CH(CH₂CH₃)-COOH | D,L | $C_{13}H_{16}NO_4Cl$ 285.73 |
| | 78 | -NH(CH₃)-CH(CH₂CH₃)-CONH₂ | D,L | $C_{13}H_{17}N_2O_3Cl$ 284.75 |
| | 79 | -NH(CH₃)-(CH₂)₃-COOH | — | $C_{13}H_{16}NO_4Cl$ 285.73 |
| 4-Cl-2-CH₃ | 80 | -NH(CH₃)-CH₂-CH(OH)-CH₃ | R,S | $C_{12}H_{16}NO_3Cl$ 257.72 |
| | 81 | -NH(CH₃)-CH₂-CH(OH)-CH₂CH₃ | R,S | $C_{13}H_{18}NO_3Cl$ 271.75 |
| | 82 | -NH(CH₃)-CH₂-CH(OH)-Ph | R,S | $C_{17}H_{18}NO_3Cl$ 319.79 |
| 2,4,6-(CH₃)₃ | 83 | -NH(CH₃)-CH₂-CH(OH)-Ph | R,S | $C_{19}H_{23}NO_3$ 313.38 |

Example 4

Biological Activity Assays for Achieved Compounds

The compounds in the invention were subject to pharmacological tests: MES (maximal electroshock seizures), ScMet (subcutaneous pentylenetetrazol) and TOX (neurotoxicity test) in mice and rats (intraperitoneal i.p. and oral p.o. administration).

In order to define anticonvulsant activity, screening tests were performed, using animal models of seizures. The tests were initially performed in mice (Carworth Farms No. 1), and if results proved activity—in rats (Sprague-Dawley). The tests were based on administration of a compound to an animal and after certain time inducing state similar to epilepsy attack in human. Each substance (after dissolving in methylcellulose) was normally tested in doses 30, 100, and 300 mg/kg body weight (b.w.) (mice) or in 30 and 50 mg/kg b.w. (rats) in two possible routes of administration: intraperitoneal (i.p.) or oral (p.o.). Appropriate tests were performed 0.5 and 4 h after administration of the compound. In cases of substances revealing activity in 30 mg/kg b.w. (mice) the tests were also performed in doses 10 and 3 mg/kg b.w.

Maximum Electroshock Seizure (MES) test is an electric test, verifying activity towards generalized tonic-clonic seizures (grand mal epilepsy) [9]. According to the literature, the most active compounds are those which inhibit voltage-gated sodium channels [10]. Its procedure consists in administration to an animal a mentioned dose, and after 0.5 or 4 h attaching corneal electrodes (after anesthetic eye-drops: 0.5% tetracaine hydrochloride in 0.9% NaCl) and turning on electric current (60 Hz, 0.2 s, 50 mA (mice) or 150 mA (rats)). If the tested substance reveals anticonvulsant activity, the used electric pulse will not reveal tonic-clonic seizures in the animal. Normally, in the dose 30 mg/kg b.w. the test is done in 1 mouse after 0.5 or 4 h, in the dose 100 mg/kg b.w.—in 3 mice, and in the dose 300 mg/kg b.w.—in 1 mouse [11-12].

Subcutaneous Metrazol Test (ScMet) is a chemical test, where compounds are tested for activity in absence seizures (petit mal epilepsy). Pentetrazol (metrazol) is considered to block chloride channel in the $GABA_A$ receptor complex, therefore at a certain dose in animals it causes myoclonic jerks, next—clonic seizures, and then tonic seizures. The procedure consists in administration of a tested compound and after 0.5 or 4 h subcutaneous administration of pentylenetetrazol in the dose of 85 mg/kg b.w. (mice) or 70 mg/kg b.w. (rats) in a 0.85% solution in 0.9% NaCl. The tested substance reveals anticonvulsant activity, if the dose of pentylenetetrazol does not induce seizures in the animal. Normally the test is performed in single animals.

Neurotoxicity test (TOX) is performed in order to eliminate substances exhibiting neurotoxicity. It is performed with use of rotarod test. The animal is placed on a plastic rod (1 inch in diameter), rotating 6 rpm. The rod is placed on a level discouraging the animal to jump off. If the tested compound (administered 0.5 or 4 h before the test) does not reveal neurotoxic effect (ataxia, sedation, excitation), the animal will keep its position on the rod for at least 1 min. Neurotoxicity is stated if the animal cannot stay on the rod for 1 min. in any of 3 trials [11]. Normally the test is performed in dose 30 mg/kg b.w. in 4 mice (0.5 h) and in 2 mice (4 h), in the dose 100 mg/kg b.w. in 8 mice (0.5 h) and in 4 mice (4 h) and in the dose 300 mg/kg b.w. in 4 mice (0.5 h) and 2 mice (4 h). It should be mentioned, that results of another commonly used test—chimney test—are concurrent with the described test [13].

Results in mice

Compounds 1-83 were subject to initial pharmacological screening. Their results are presented in Table 4 below.

TABLE 4

| Compd. | Dose [mg/kg b.w.] | MES[a] 0.5 | MES[a] 4 | ScMet[a] 0.5 | ScMet[a] 4 | TOX[b] 0.5 | TOX[b] 4 |
|---|---|---|---|---|---|---|---|
| 1 | 30 | — | — | — | — | — | — |
|  | 100 | 3/3 | — | — | — | 7/8 | — |
|  | 300 | — | — | — | — | 4/4 | — |
| 2 | 30 | — | — | — | — | — | — |
|  | 100 | 3/3 | — | — | — | 8/8 | — |
|  | 300 | — | — | — | — | 4/4 | — |
| 3 | 30 | — | — | — | — | — | — |
|  | 100 | 2/3 | — | — | — | 7/8 | — |
|  | 300 | — | — | — | — | 4/4 | — |
| 4 | 30 | — | — | 1/5 | — | — | — |
|  | 100 | — | — | — | — | 4/8 | 1/4 |
|  | 300 | — | — | — | — | 3/4 | — |
| 5 | 30 | — | — | — | — | — | — |
|  | 100 | 3/3 | — | — | — | 8/8 | 1/4 |
|  | 300 | — | — | — | — | 4/4 | — |
| 6 | 30 | — | — | — | — | 2/4 | 1/2 |
|  | 100 | 3/3 | — | — | — | 8/8 | 1/4 |
|  | 300 | 1/1 | — | — | — | 4/4 | — |
| 7 | 30 | — | — | — | — | — | — |
|  | 100 | 3/3 | — | — | — | 8/8 | — |
|  | 300 | 1/1 | — | — | — | 4/4 | — |
| 8 | 30 | — | — | — | — | — | — |
|  | 100 | 3/3 | — | — | — | 8/8 | — |
|  | 300 | — | — | — | — | 4/4 | — |
| 9 | 30 | — | — | — | — | — | — |
|  | 100 | — | — | — | — | 7/8 | — |
|  | 300 | — | — | — | — | 3/4 | 1/2 |
| 10 | 10 | — | — | — | — | — | — |
|  | 30 | 1/1 | — | — | — | 1/4 | — |
|  | 100 | — | 2/2 | — | — | 8/8 | 1/3 |
|  | 300 | — | — | — | — | 4/4 | — |
| 11 | 3 | — | — | — | — | — | — |
|  | 10 | — | — | — | — | — | — |
|  | 30 | 1/1 | — | — | — | 2/4 | — |
|  | 100 | — | — | — | — | 8/8 | — |
|  | 300 | — | — | — | — | 4/4 | — |
| 11a | 3 | — | — | — | — | — | — |
|  | 10 | — | — | — | — | — | — |
|  | 30 | 1/1 | — | — | — | 3/4 | — |
|  | 100 | 1/1 | — | — | — | 8/8 | — |
|  | 300 | — | — | — | — | 4/4 | — |
| 12 | 3 | — | — | — | — | — | — |
|  | 10 | 1/4 | — | — | — | — | — |
|  | 30 | 1/1 | — | — | — | — | — |
|  | 100 | 2/2 | 1/2 | — | — | 8/8 | 1/3 |
|  | 300 | — | — | — | — | 4/4 | — |
| 12a | 30 | — | — | — | — | — | — |
|  | 100 | 3/3 | — | — | — | 8/8 | — |
|  | 300 | — | — | — | — | 4/4 | 1/1 |
| 13 | 3 | — | — | — | — | — | — |
|  | 10 | 2/4 | — | — | — | — | — |
|  | 30 | 1/1 | — | — | — | — | — |
|  | 100 | — | — | — | — | 8/8 | — |
|  | 300 | — | — | — | — | 4/4 | — |
| 13a | 3 | — | — | — | — | — | — |
|  | 10 | — | — | — | — | — | — |
|  | 30 | 1/1 | — | — | — | — | — |
|  | 100 | 3/3 | — | — | — | 8/8 | — |
|  | 300 | — | — | — | — | 4/4 | — |
| 14 | 3 | — | — | — | — | — | — |
|  | 10 | — | — | — | — | — | — |
|  | 30 | 1/1 | — | — | — | 1/4 | — |
|  | 100 | 1/1 | — | — | — | 8/8 | — |
|  | 300 | — | — | — | — | 4/4 | — |
| 15 | 3 | — | — | — | — | — | — |
|  | 10 | 2/2 | — | — | — | 7/8 | — |
|  | 30 | — | — | — | — | 4/4 | — |
|  | 100 | — | — | — | — | — | — |
|  | 300 | 2/2 | — | — | — | 7/8 | — |
| 16 | 3 | — | — | — | — | — | — |
|  | 100 | 2/2 | — | — | — | 7/8 | — |
|  | 300 | — | — | — | — | 4/4 | — |
| 17 | 3 | — | — | — | — | — | — |
|  | 100 | 3/3 | — | — | — | 7/8 | — |
|  | 300 | — | — | — | — | 4/4 | 1/1 |
| 18 | 3 | — | — | — | — | — | — |
|  | 100 | 3/3 | — | — | — | 7/8 | — |
|  | 300 | — | — | — | — | 4/4 | — |
| 19 | 3 | — | — | — | — | — | — |
|  | 10 | — | — | — | — | — | — |
|  | 30 | 1/1 | — | — | — | 1/4 | — |
|  | 100 | 3/3 | — | — | — | 8/8 | — |
|  | 300 | — | — | — | — | 4/4 | — |
| 20 | 3 | — | — | — | — | — | — |
|  | 10 | — | — | — | — | — | — |
|  | 30 | 1/1 | — | — | — | — | — |
|  | 100 | — | — | — | — | 8/8 | — |
|  | 300 | — | — | — | — | 4/4 | — |
| 21 | 3 | — | — | — | — | — | — |
|  | 10 | — | — | — | — | — | — |
|  | 30 | 1/1 | — | — | — | — | — |
|  | 100 | 3/3 | — | — | — | 7/8 | — |
|  | 300 | — | — | — | — | 4/4 | — |
| 22 | 30 | — | — | — | — | — | — |
|  | 100 | 2/2 | 2/2 | — | — | 8/8 | — |
|  | 300 | — | — | — | — | 4/4 | — |
| 23 | 3 | — | — | — | — | — | — |
|  | 10 | — | — | — | — | — | — |
|  | 30 | 1/1 | — | — | — | — | — |
|  | 100 | 1/1 | — | — | — | 7/8 | — |
|  | 300 | — | — | — | — | 4/4 | — |
| 24 | 30 | — | — | — | — | — | — |
|  | 100 | 3/3 | — | — | — | 5/8 | — |
|  | 300 | — | — | — | — | 4/4 | — |
| 25 | 3 | — | — | — | — | — | — |
|  | 10 | — | — | — | — | 8/8 | — |
|  | 30 | 1/1 | — | — | — | 4/4 | — |
|  | 100 | — | — | — | — | — | — |
|  | 300 | — | — | — | — | — | — |
| 26 | 3 | — | — | — | — | — | — |
|  | 10 | 2/4 | — | — | — | — | — |
|  | 30 | 1/1 | — | — | — | — | — |
|  | 100 | 1/1 | — | — | — | 8/4 | — |
|  | 300 | — | — | — | — | 4/4 | — |
| 26a | 3 | — | — | — | — | — | — |
|  | 10 | — | — | — | — | — | — |
|  | 30 | 1/1 | — | — | — | 3/4 | — |
|  | 100 | 1/1 | — | — | — | 8/8 | 1/4 |
|  | 300 | — | — | — | — | 4/4 | — |
| 27 | 3 | — | — | — | — | — | — |
|  | 10 | — | — | — | — | — | — |
|  | 30 | 1/1 | — | — | — | — | — |
|  | 100 | 1/1 | — | — | — | 8/8 | — |
|  | 300 | — | — | — | — | 4/4 | — |
| 27a | 30 | 1/1 | — | — | — | — | — |
|  | 100 | 2/3 | — | — | — | 7/8 | — |
|  | 300 | — | — | — | — | 4/4 | — |
| 28 | 30 | 1/1 | — | — | — | — | — |
|  | 100 | 1/1 | — | — | — | 8/8 | — |
|  | 300 | — | — | — | — | 4/4 | — |
| 28a | 30 | — | — | — | — | — | — |
|  | 100 | 1/1 | — | — | — | 5/8 | — |
|  | 300 | — | — | — | — | 4/4 | — |
| 29 | 30 | — | — | — | — | — | — |
|  | 100 | 2/3 | — | — | — | 4/8 | — |
|  | 300 | — | — | — | — | 4/4 | — |
| 30 | 3 | — | — | — | — | — | — |
|  | 10 | — | — | — | — | — | — |
|  | 30 | 1/1 | — | — | — | — | — |
|  | 100 | 1/1 | — | — | — | 8/8 | — |
|  | 300 | — | — | — | — | 4/4 | — |
| 31 | 3 | — | — | — | — | — | — |
|  | 10 | — | — | — | — | — | — |
|  | 30 | 1/1 | — | — | — | — | — |
|  | 100 | 3/3 | — | — | — | 8/4 | — |
|  | 300 | 1/1 | — | — | — | 4/4 | — |

TABLE 4-continued

| Compd. | Dose [mg/kg b.w.] | MES[a] 0.5 | MES[a] 4 | ScMet[a] 0.5 | ScMet[a] 4 | TOX[b] 0.5 | TOX[b] 4 |
|---|---|---|---|---|---|---|---|
| 32 | 3 | — | \| | \| | \| | — | \| |
|  | 10 | — | \| | \| | \| | — | \| |
|  | 30 | 1/1 | — | — | — | — | — |
|  | 100 | 3/3 | 1/3 | — | — | 7/8 | — |
|  | 300 | 1/1 | \| | \| | — | 4/4 | 1/1 |
| 33 | 30 | — | — | — | — | — | — |
|  | 100 | 3/3 | — | — | — | 4/8 | — |
|  | 300 | \| | \| | \| | \| | 4/4 | — |
| 34 | 30 | — | — | — | — | 1/4 | — |
|  | 100 | 3/3 | — | — | — | 7/8 | — |
|  | 300 | \| | \| | \| | \| | 4/4 | \| |
| 35 | 30 | — | — | — | — | — | — |
|  | 100 | 3/3 | — | — | — | 8/8 | — |
|  | 300 | \| | \| | \| | \| | 4/4 | \| |
| 36 | 30 | — | — | — | — | — | — |
|  | 100 | 3/3 | — | — | — | — | — |
|  | 300 | \| | \| | — | \| | 4/4 | \| |
| 37 | 30 | — | — | — | — | — | — |
|  | 100 | — | — | — | — | — | — |
|  | 300 | — | — | — | — | 1/4 | — |
| 38 | 3 | — | \| | \| | \| | — | \| |
|  | 10 | — | \| | \| | \| | — | \| |
|  | 30 | 1/1 | — | — | — | 1/4 | 1/2 |
|  | 100 | 3/3 | 2/2 | — | — | 8/8 | 1/3 |
|  | 300 | \| | \| | \| | \| | 4/4 | \| |
| 39 | 3 | — | \| | \| | \| | — | \| |
|  | 10 | — | \| | \| | \| | — | \| |
|  | 30 | 1/1 | — | — | — | — | — |
|  | 100 | 3/3 | 1/3 | — | — | 7/8 | — |
|  | 300 | \| | — | \| | \| | 4/4 | — |
| 40 | 10 | — | \| | \| | \| | — | \| |
|  | 30 | 1/1 | — | — | — | — | — |
|  | 100 | 2/3 | 1/3 | — | — | 4/8 | — |
|  | 300 | \| | — | \| | \| | 4/4 | \| |
| 41 | 10 | — | \| | \| | \| | — | \| |
|  | 30 | 1/1 | — | — | — | 3/4 | — |
|  | 100 | 3/3 | — | — | — | 7/8 | — |
|  | 300 | \| | \| | \| | \| | 4/4 | \| |
| 42 | 30 | — | — | — | — | 3/4 | 1/2 |
|  | 100 | 3/3 | 1/3 | — | — | 8/8 | 4/4 |
|  | 300 | 1/1 | \| | \| | — | 4/4 | 1/1 |
| 43 | 30 | — | — | — | — | 3/4 | — |
|  | 100 | 3/3 | — | — | — | 8/8 | — |
|  | 300 | \| | \| | \| | \| | 4/4 | \| |
| 44 | 3 | — | \| | \| | \| | — | \| |
|  | 10 | 1/4 | \| | \| | \| | 1/4 | \| |
|  | 30 | 1/1 | — | — | — | — | — |
|  | 100 | \| | — | — | — | 8/8 | — |
| 45 | 30 | — | — | — | — | — | — |
|  | 100 | 3/3 | — | — | — | — | — |
|  | 300 | 1/1 | 1/1 | — | — | 3/4 | — |
| 46 | 30 | — | — | — | — | — | — |
|  | 100 | 3/3 | — | — | — | 8/8 | — |
|  | 300 | \| | \| | \| | \| | 4/4 | \| |
| 47 | 30 | — | — | — | — | — | — |
|  | 100 | 3/3 | — | — | — | 8/8 | 4/4 |
|  | 300 | \| | \| | \| | \| | 4/4 | \| |
| 48 | 30 | — | — | — | — | — | — |
|  | 100 | 3/3 | — | — | — | 8/8 | — |
|  | 300 | \| | \| | \| | \| | 4/4 | \| |
| 49 | 30 | — | — | — | — | 1/4 | 1/2 |
|  | 100 | — | — | — | — | 6/8 | 3/4 |
|  | 300 | 1/1 | — | — | — | 4/4 | 2/2 |
| 50 | 3 | — | \| | \| | \| | — | \| |
|  | 10 | — | \| | \| | \| | — | \| |
|  | 30 | 1/1 | — | — | — | 3/4 | — |
|  | 100 | 3/3 | — | — | — | 7/8 | 2/4 |
|  | 300 | \| | \| | \| | \| | 4/4 | — |
| 51 | 3 | — | \| | \| | \| | — | \| |
|  | 10 | — | \| | \| | \| | — | \| |
|  | 30 | 1/1 | — | — | — | 2/4 | — |
|  | 100 | 3/3 | — | — | — | 8/8 | 1/3 |
|  | 300 | \| | \| | \| | \| | 4/4 | \| |
| 52 | 3 | — | \| | \| | \| | — | \| |
|  | 10 | — | \| | \| | \| | 1/4 | \| |
|  | 30 | 1/1 | — | — | — | — | — |
|  | 100 | 2/3 | — | — | — | 6/8 | 1/4 |
|  | 300 | — | 1/1 | \| | \| | 3/4 | — |
| 53 | 30 | — | — | — | — | 1/4 | — |
|  | 100 | 3/3 | — | — | \| | 8/8 | — |
|  | 300 | \| | \| | \| | \| | 4/4 | \| |
| 54 | 30 | — | — | 1/5 | 1/1 | 1/4 | — |
|  | 100 | 2/2 | — | \| | \| | 8/8 | 1/1 |
|  | 300 | \| | \| | \| | \| | 4/4 | \| |
| 55 | 3 | — | \| | \| | \| | — | \| |
|  | 10 | — | \| | \| | \| | — | \| |
|  | 30 | 1/1 | — | — | — | — | — |
|  | 100 | 3/3 | — | \| | — | 8/8 | — |
|  | 300 | \| | \| | \| | \| | 4/4 | \| |
| 56 | 30 | — | — | — | — | 2/4 | — |
|  | 100 | 1/1 | — | — | — | 8/8 | — |
|  | 300 | \| | \| | \| | \| | 4/4 | \| |
| 57 | 30 | — | — | — | — | 4/4 | 1/2 |
|  | 100 | \| | \| | \| | \| | 8/8 | \| |
|  | 300 | \| | \| | \| | \| | 4/4 | \| |
| 58 | 30 | — | — | — | — | — | — |
|  | 100 | 2/3 | — | — | — | 6/8 | — |
|  | 300 | \| | \| | \| | \| | 4/4 | 1/1 |
| 59 | 30 | — | — | — | — | — | — |
|  | 100 | — | — | — | — | — | — |
|  | 300 | 1/1 | — | 1/1 | — | 4/4 | — |
| 60 | 30 | — | — | — | — | — | — |
|  | 100 | — | — | — | — | 2/8 | 2/4 |
|  | 300 | 1/1 | — | — | — | 2/4 | — |
| 61 | 30 | — | — | — | — | — | — |
|  | 100 | — | — | — | — | — | — |
|  | 300 | 1/1 | — | — | — | 2/4 | — |
| 62 | 30 | — | — | — | — | 1/4 | — |
|  | 100 | — | — | — | — | 3/8 | 1/4 |
|  | 300 | 1/1 | 1/1 | — | — | 3/4 | 1/2 |
| 63 | 30 | — | — | — | — | — | — |
|  | 100 | — | — | — | — | — | — |
|  | 300 | 1/1 | — | — | — | 4/4 | — |
| 64 | 30 | — | — | — | — | — | — |
|  | 100 | 3/3 | — | — | — | 7/8 | — |
|  | 300 | 1/1 | — | 1/1 | — | 4/4 | — |
| 65 | 30 | — | — | — | — | 1/5 | — |
|  | 100 | — | — | — | — | 2/8 | — |
|  | 300 | 1/1 | — | — | — | 1/4 | — |
| 66 | 30 | — | — | — | — | — | — |
|  | 100 | — | — | — | — | — | — |
|  | 300 | — | — | — | — | — | — |
| 67 | 30 | — | — | — | — | — | — |
|  | 100 | 2/3 | — | — | — | 1/8 | — |
|  | 300 | 1/1 | — | — | — | 4/4 | — |
| 68 | 30 | — | — | — | — | — | — |
|  | 100 | — | — | — | — | — | — |
|  | 300 | — | — | 1/1 | — | 4/4 | — |
| 69 | 30 | — | — | — | — | — | — |
|  | 100 | — | — | — | — | 1/8 | — |
|  | 300 | 1/1 | — | — | — | 1/4 | — |
| 70 | 30 | — | — | — | — | — | — |
|  | 100 | — | — | — | — | — | — |
|  | 300 | 1/1 | — | — | — | 3/4 | — |
| 71 | 30 | — | — | — | — | — | — |
|  | 100 | — | — | — | — | — | — |
|  | 300 | 1/1 | — | — | — | 4/4 | — |
| 72 | 30 | — | — | — | — | — | — |
|  | 100 | — | — | — | — | — | — |
|  | 300 | 1/1 | — | 1/1 | — | 4/4 | — |
| 73 | 30 | — | — | — | — | — | — |
|  | 100 | — | — | 3/5 | — | — | — |
|  | 300 | 1/1 | 1/1 | 1/1 | — | 4/4 | — |
| 74 | 30 | — | — | — | — | — | — |
|  | 100 | — | — | — | — | — | — |
|  | 300 | — | — | — | — | — | — |

TABLE 4-continued

| Compd. | Dose [mg/kg b.w.] | MES[a] 0.5 | MES[a] 4 | ScMet[a] 0.5 | ScMet[a] 4 | TOX[b] 0.5 | TOX[b] 4 |
|---|---|---|---|---|---|---|---|
| 75 | 30 | — | — | — | — | — | — |
|  | 100 | — | — | — | — | — | — |
|  | 300 | — | — | — | — | — | — |
| 76 | 30 | — | — | — | — | — | — |
|  | 100 | — | — | — | — | — | — |
|  | 300 | — | — | — | — | — | — |
| 77 | 30 | — | — | — | — | — | — |
|  | 100 | — | — | — | — | — | — |
|  | 300 | — | — | — | — | — | — |
| 78 | 30 | — | — | — | — | — | — |
|  | 100 | — | — | — | — | — | — |
|  | 300 | — | — | — | — | 1/4 | — |
| 79 | 30 | — | — | — | — | — | — |
|  | 100 | — | — | — | — | — | — |
|  | 300 | — | — | — | — | 1/4 | — |
| 80 | 30 | — | — | — | — | — | — |
|  | 100 | — | — | — | — | — | — |
|  | 300 | 1/1 | — | 1/1 | — | 4/4 | — |
| 81 | 30 | — | — | — | — | — | — |
|  | 100 | — | — | — | — | — | — |
|  | 300 | 1/1 | — | 1/1 | — | 4/4 | — |
| 82 | 30 | — | — | — | — | — | — |
|  | 100 | — | — | — | — | 2/8 | — |
|  | 300 | — | — | — | — | 4/4 | 1/2 |
| 83 | 30 | — | — | — | — | — | — |
|  | 100 | — | — | — | — | — | — |
|  | 300 | — | — | — | — | 4/4 | — |

[a] No. of protected animals/No. of used animals;
[b] No. of animals exhibiting motor impairment/no. of used animals;
— no activity or no neurotoxicity;
| not tested.

For the most active substances there are time to peak effect (TPE), $ED_{50}$ doses (the lowest dose active in 50% of animals), $TD_{50}$ (the lowest dose neurotoxic in 50% of animals) and protection index (PI) for intraperitoneal (i.p.) and oral (p.o.) administration.

For some compounds, a test for proconvulsant activity was performed (TTE test), as well as a test on activity in focal seizures (related with limbic system, 6 Hz test, hippocampal kindling). Activity in pharmacoresistant seizures has been revealed (lamotrigine-resistant amygdala kindling, rats, i.p.). A test on inhibiting seizures induced by sound (Frings mice) was performed for compounds 12 and 26-28. Electrophysiology tests also have been performed, for seizures induced by bicuculline, picrotoxin, and NMDA. Prevention of (pilocarpine induced) status epilepticus has been noticed.

Formalin test has revealed analgesic activity in the phase of neuropathic pain as well as inflammatory pain. Tests on mutagenic activity (Ames' and Vibrio harveyi) revealed broad safety in this matter. Tests in cytochromes $P_{450}$ for prediction of possible interaction with other drugs have revealed broad safety-non-competitive inhibition of CYP2D6 (Ki=22.3 μM).

As a result it was revealed that compound 12 is active in MES in mice and rats. Below there are ED50s and P is for some tests:
$TPE_{TOX}$=0.25 h; $TPE_{MES}$=0.25 h
$ED_{50}$ (MES, mice, i.p., 0.25 h)=5.34 mg/kg b.w.; PI (MES, mice, i.p.)=5.51
$ED_{50}$ (MES, female mice, i.p., 0.25 h)=22.28 mg/kg b.w.; PI (MES, mice, i.p.)=1.74
$ED_{50}$ (MES, mice, p.o., 0.25 h)=51.19 mg/kg b.w.; PI (MES, mice, p.o.)=2.82
$ED_{50}$ (MES, rats, p.o., 0.25 h)=28.60 mg/kg b.w.; PI (MES, rats, p.o.)>17.48
$ED_{50}$ (MES, rats, i.p., 0.25 h)=7.43 mg/kg b.w.; PI (MES, rats, i.p.)=6.74
$ED_{50}$ (6 Hz, mice, i.p., 44 mA, 0.25 h)=30.02 mg/kg b.w.
$ED_{50}$ (6 Hz, female mice, i.p., 44 mA, 0.25 h)=41.3 mg/kg b.w.
$ED_{50}$ (6 Hz, mice, i.p., 22 mA, 0.25 h)=43.81 mg/kg.
$ED_{50}$ (6 Hz, female mice, i.p., 22 mA, 0.25 h)=7.06 mg/kg.
$ED_{50}$ (Frings mice, 0.25 h)=5.39 mg/kg b.w.
$ED_{50}$ (kindling, rats, hippocampus, 0.25 h)>30 mg/kg b.w.
$ED_{50}$ (BIC, 0.25 h)>75 mg/kg b.w.
$ED_{50}$ (PIC, 0.25 h)>75 mg/kg b.w.

Compound 12 blocks voltage-gated sodium channels dependently on the voltage. In the MES test it inhibits seizures by inhibiting post-synaptic excitatory current. In the electric kindling (rats, hippocampus) the substance reveals activity 0.25 h after administration of 60 mg/kg b.w. In the metrazol test average time until the first twitch was 27.3±0.2 min. for the dose 5 mg/kg b.w. and 27.6 (+0.3) min. for the dose 30 mg/kg b.w., comparing to the control 30.07 (±1.23) min. Average time from administration until the first clonus was 33.6 (±1.23) min. for the dose 5 mg/kg b.w. and 32.70 (±1.28) for the dose 30 mg/kg b.w., comparing to the control 34.38 (±0.94) min. Results in the formalin test in FIG. 3 indicate inhibiting neuropathic pain (first 10 min. phase) and inflammatory pain (next 30 min. phase).

The formalin test also has been performed for compound 26.

The test was performed with use of formaldehyde as a substance causing pain (neuropathic and inflammatory afterwards) in mice, which were injected formalin into a hind limb. The test used a dose of a tested substance equivalent to $ED_{50}$ (MES, mice, i.p.) administered 21.44 mg/kg b.w. to mice, i.p., and after TPE time (MES, mice, i.p.=0.25 h) formalin is administered in order to measure the time of reaction of the animals to the pain stimulus (licking the limb).

During the first 10 min. after administration the mouse is licking the hind limb (acute phase), afterwards there is a short break in behavior change, and then the mouse licks its limb again for another 20-30 min. (inflammatory phase) (FIG. 3 for 12 and FIG. 4 for 26). The acute phase represents direct affection on the peripheral nerve and the inflammatory phase is related with secretion of inflammation mediators from the damaged tissue and nerves. The described model tests effectiveness of a substance to inhibit acute and chronic excessive neuronal discharges in response to peripheral nerves activation.

FIG. 4 shows a graph representing calculated average results (time) for 8 animals in the test, at the dose 21 mg/kg b.w. (which is corresponding to MES $ED_{50}$ (mice, i.p.)=21.44 mg/kg b.w. As it can be noticed, compound 26 inhibits acute phase of the formalin test (first ca. 10 min. after formalin administration) (64% of control), which means analgesic activity in neuropathic pain. The results are statistically significant (p<0.01). Lowering pain in the inflammatory phase (72% of control) is not statistically significant. In order to fully interpret the results, FIG. 5 presents comparison with known antiepileptic drugs (AEDs) such as carbamazepine (CBZ) and valproic acid (VPA) in typical doses. The smaller % of AUC (area under curve) comparing to the control (methylcellulose, MC), and the shorter bar, the stronger analgesic activity. Therefore, it can be stated, that the compound is more effective than VPA in the acute phase, and less active in the inflammatory phase compared to VPA and CBZ.

Comparison of anticonvulsant activity in MES in mice and rats after intraperitoneal i.p. and oral p.o. administration for isomers:

R,S, R-(−) and S-(+)-2-[(2,6-dimethylphenoxy)ethyl]amino-1-propanol

TABLE 5

| Parameter | compound 11 R,S | compound 12 R-(−) | compound 13 S-(+) |
|---|---|---|---|
| $ED_{50}$ (MES, mice, i.p., 0.25 h) [mg/kg b.w.] | — | 5.34 | 8.59 |
| PI (MES, mice, i.p., 0.25 h) | — | 5.51 | 4.38 |
| $ED_{50}$ (MES, rats, i.p., 0.25 h) [mg/kg b.w.] | 0 | 7.43 | 6.50 |
| PI (MES, rats, i.p.) | 0 | 6.74 | 5.51 |
| $ED_{50}$ (MES, rats, p.o., 0.25 h) [mg/kg b.w.] | 47.03 | 28.60 | — |
| PI (MES, rats, p.o., 0.25 h) | <10.63 | >17.48 | — |

As it can be noticed (Table 5), in mice, $ED_{50}$ is lower for R than for S enantiomer (5.34 and 8.59 mg/kg b.w., respectively), with higher protection index (PI) (5.51 and 4.38 mg/kg b.w., respectively), which indicates higher effectiveness and greater safety of the R enantiomer. In rats (i.p.) the R also shows higher PI than S (6.74 and 5.51, respectively). In rats (p.o.) enantiomer R reveals more beneficial $ED_{50}$ (28.60 and 47.03 mg/kg b.w., respectively) and more beneficial PI (>17.48 and <10.63, respectively) than the racemate. Therefore, it can be stated, that among the isomers, it is R (compound 12) that reveals more beneficial pharmacological properties than S (13) and R,S (11).

All results were presented after TPE=0.25 h (as in MES). $TD_{50}$s used for PI calculation were taken from the rotarod (TOX) test for neurotoxicity.

Comparison of activity of enantiomers R-(−)- and S-(+)-[(2-chlor-6-methylphenoxy)ethyl)amino-1-butanol (compounds 27 and 28, respectively).

Acute toxicity—minimal dose of substance (i.p.) causing acute motor impairment; the test uses at least 12 rats, observed for 4 h after administration (FIG. 6 Graph 1).

Status epilepticus prevention—an animal (Sprague Dawley albino rat male) is given a dose of tested substance. After 0, 0.25, 0.5, 1, 2, and 4 h pilocarpine is administered. The seizures induced are described by Racine's score. Compounds 27 and 28 were administered i.p. in doses 25 and 45 mg/kg b.w. respectively. They both exhibit protection in 2 and 3 rats out of 8. The results are presented below. Average body weight loss is measured 24 h after administration.

Status epilepticus prevention of compounds 27 and 28.

TABLE 6

| Compound | Dose [mg/kg b.w.] | Time [h] | Protection | Average weight loss ± S.E.M. |
|---|---|---|---|---|
| 27 | 25, i.p. | 0 | 2/8 | 8.3 ± 7.1 |
| 28 | 45, i.p. | 0 | 3/8 | 3.8 ± 5.7 |

As it can be noticed (Table 6), the doses needed for activity in this test is different for both enantiomers—R has proved to be more beneficial. However, in electric hippocampal kindling seizures in rats, i.p. it was S that proved more active. Therefore, it can be summarized, that enantiomer R is more effective in preventing status epilepticus, and S—in preventing limbic, focal seizures.

Below there are results for compounds 26 and 28.
26 TPETOX=0.25 h; $TPE_{MES}$=0.25 h,
26 $ED_{50}$ (MES, mice, i.p., 0.25 h)=21.44 mg/kg b.w.; PI (MES, mice, i.p.)=2.56,
26 $ED_{50}$ (MES, rats, p.o., 0.25 h)=67.69 mg/kg b.w.; PI (MES, rats, p.o.)>3.55,
26 $ED_{50}$ (MES, rats, i.p., 0.25 h)=7.3 mg/kg b.w.; PI (MES, rats, i.p.)=4.5,
26 TPE (6 Hz, mice, i.p., 32 mA)=0.5 h,
28 $ED_{50}$ (kindling, rats, hippocampus, 0.25 h)=15.81 mg/kg b.w.,
26 (LTG-resistant amygdala seizures) t=0.25 h; effective dose=15 mg/kg b.w.,
26 $ED_{50}$ (sound induced seizures, mice, 0.25 h)=6.05 mg/kg b.w.,
26 $ED_{50}$ (PIC, 0.25 h)>70 mg/kg b.w.,
26 $ED_{50}$ (BIC, 0.25 h)>70 mg/kg b.w., 26 neuropathic pain inhibition (formalin test, 21 mg/kg b.w.)=36%.

Below there are pharmacological data for the optimum enantiomer R-(+)-2-[(2,6-dimethylphenoxy)acetyl]amino-1-propanol (compound 68):

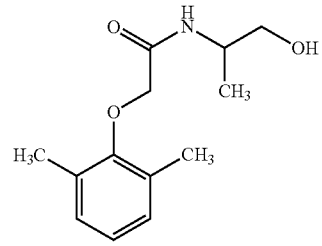 [SMILES: Cc1cccc(C)c1OCC(=O)NC(C)CO]

$ED_{50}$ (MES, mice, i.p.)=97.93 mg/kg b.w.
PI (MES, mice, i.p.)=1.43

References

1. Fischer W.: *Anticonvulsant profile and mechanism of action of propranolol and its two enantiomers.* Seizure 11: 285-302 (2002).
2. Alexander G. J., Kopeloff L. M., Alexander R. B., Chatterjie N.: Mexiletine: biphasic action on convulsive seizures in rodents. Neurobehav. Toxicol. Teratol. 8: 231-235 (1986).
3. Chew C. Y. C., Collett J., Singh B. N.: Mexiletine: A Review of its Pharmacological Properties and Therapeutic Efficacy in Arrhythmias. Drugs 17: 161-181 (1979).
4. Orlof M. J., Williams H. L., Pfeiffer C. C.: Timed intervenous infusion of metrazol and strychnine for testing anticonvulsant drugs. Proc. Soc. Exp. Bioi. Med. 70: 254-257 (1949).
5. Marana H., Antkiewicz-Michaluk L.: Synthesis and anticonvulsant activity of 1,2-aminoalkanol derivatives. Acta Pol. Pharm.-Drug Res. 55: 487-498 (1998).
6. Waszkielewicz A. M., Cegla M., Marona H.: Preliminary evaluation of anticonvulsant activity of some [4-(benzyloxy)-benzoyl]- and [4-(benzyloxy)-benzyl]-aminoalkanol derivatives. Acta Pol. Pharm.-Drug Res. 64, 147-157 (2007).
7. Pekala E., Gajewczyk L., Marona H.: Synthesis of New N-acyl Derivatives of DL-trans-1,2-Aminocyclohexanol. Acta Pol. Pharm.-Drug Res. 51: 339-342 (1994).
8. Marona H., Ptekala E.: Synthesis of Some N-acyl Derivatives of Optically Active trans-2-Amino-1-cyclohexanols. Acta Pol. Pharm.-Drug Res. 53: 111-115 (1996).
9. Swinyard E. A., Woodhead J. H., White, H. S., Franklin M. R.: General principles: experimental selection, quantification, and evaluation of anticonvulsants. Antiepileptic Drugs, Str. 85-102, Wyd. 3. Raven Press, Nowy Jork 1989.
10. Rogawski M. A., Porter R. J.: Antiepileptic Drugs: Pharmacological Mechanisms and Clinical Efficacy with Consideration of Promising Developmental Stage Compounds. Pharmacol. Rev. 42: 223-286 (1990).
11. Stables J. P., Kupferberg H. J.: The NIH Anticonvulsant Drug Development (ADD) Program: preclinical anticonvulsant screening project. Chapter 16. http://www.ninds.nih.gov/funding/research/asp/addadd_review.pdf
12. Kupferberg H.: Animal Models Used in the Screening of Antiepileptic Drugs. Epilepsia 42: 7-12 (2001).
13. Czuczwar S. J., Borowicz K. K., Kleinrok Z., Tutka P., Zarnowski T., Turski W. A.: Influence of Combined Treatment with NMDA and Non-NMDA Receptor Antagonists on Electroconvulsions in Mice. Eur. J. Pharmacol. 281: 327-333 (1995).

The invention claimed is:

1. A method of preventing and/or treating pain, comprising administering to a patient in need thereof a therapeutically effective amount of an aminoalkanol derivative, or the hydrochloride salt thereof, of formula

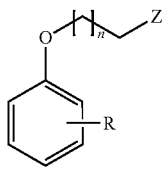

wherein n is 1 or 2;
R is 2-Cl, 6-CH$_3$; and,
Z is selected from the group consisting of 5-amino-1-pentanol, 1-amino-2-propanol, 2-amino-1-propanol, 1-amino-2-butanol, 2-amino-1-butanol, 2-amino-1-phenylethanol, 2-amino-2-methyl-1-propanol, 2-amino-2-methyl-1,3-propandiol, 3-methyl-2-amino-1-butanol, 3-methyl-3-amino-1-butanol, D,L-trans-1,2-cyclohexanolamine, N-methyl-2-amino-1-butanol, N-methyl-2-amino-1-propanol, and N-methyl-2-amino-1-phenylethanol.

2. The method of claim 1 wherein n is 1.

3. The method of preventing and/or treating pain, comprising administering to a patient in need thereof a therapeutically effective amount of the aminoalkanol derivative selected from the group consisting of:
2-[(2,3-dimethylphenoxy)ethyl]amino-1-propanol;
2-[(2,3-dimethylphenoxy)ethyl]amino-1-butanol;
2-[(2,3-dimethylphenoxy)ethyl]amino-2-methyl-1-propanol;
2-[(2,3-dimethylphenoxy)ethyl]amino-1-phenylethanol;
1-[(2,5-dimethylphenoxy)ethyl]amino-2-propanol;
2-[(2,5-dimethylphenoxy)ethyl]amino-1-propanol;
1-[(2,5-dimethylphenoxy)ethyl]amino-2-butanol;
2-[(2,5-dimethylphenoxy)ethyl]amino-1-butanol;
2-[(2,5-dimethylphenoxy)ethyl]amino-1-phenylethanol;
R-2-[(2,6-dimethylphenoxy)ethyl]amino-1-propanol;
S-2-[(2,6-dimethylphenoxy)ethyl]amino-1-propanol;
2-[(2,6-dimethylphenoxy)ethyl]-2-methylamino-1-propanol;
3-[(2,6-dimethylphenoxy)ethyl]amino-3-methyl-1-butanol;
L-2-[(2,6-dimethylphenoxy)ethyl]amino-3-methyl-1-butanol;
5-[(2,6-dimethylphenoxy)ethyl]amino-1-pentanol;
trans-2-[(2,6-dimethylphenoxy)ethyl]amino-1-cyclohexanol;
2-[(2,6-dimethylphenoxy)ethyl]amino-1-phenylethanol;
R-2-[(2,6-dimethylphenoxy)ethyl]amino-1-phenylethanol;
S-2-[(2,6-dimethylphenoxy)ethyl]amino-1-phenylethanol;
2-[(2,6-dimethylphenoxy)ethyl]-2-methylamino-1-phenylethanol;
1-[(2-chlor-6-methylphenoxy)ethyl]amino-2-propanol;
2-[(2-chlor-6-methylphenoxy)ethyl]amino-1-propanol;
1-[(2-chlor-6-methylphenoxy)ethyl]amino-2-butanol;
2-[(2-chlor-6-methylphenoxy)ethyl]amino-1-butanol;
R-2-[(2-chlor-6-methylphenoxy)ethyl]amino-1-butanol;
S-2-[(2-chlor-6-methylphenoxy)ethyl]amino-1-butanol;
2-[(2-chlor-6-methylphenoxy)ethyl]amino-2-methyl-1,3-propandiol;
trans-2-[(2-chlor-6-methylphenoxy)ethyl]amino-1-cyclohexanol;
2-[(2-chlor-6-methylphenoxy)ethyl]amino-1-phenylethanol;
2-[(2,3,5-trimethylphenoxy)ethyl]amino-1-propanol;
2-[(2,3,5-trimethylphenoxy)ethyl]amino-1-butanol;
R-2-[(2,3,5-trimethylphenoxy)ethyl]amino-1-butanol;
S-2-[(2,3,5-trimethylphenoxy)ethyl]amino-1-butanol;
2-[(2,3,5-trimethylphenoxy)ethyl]amino-1-phenylethanol;
R-2-[(2,4,6-trimethylphenoxy)ethyl]amino-1-propanol;
trans-2-[(2,4,6-trimethylphenoxy)ethyl]amino-1-cyclohexanol;
2-[(2,4,6-trimethylphenoxy)ethyl]amino-1-phenylethanol;
2-[(2,3-dimethylphenoxy)propyl]amino-1-propanol;
2-[(2,3-dimethylphenoxy)propyl]amino-2-methyl-1-propanol;
2-[(2,3-dimethylphenoxy)propyl]amino-1-butanol;
2-[(2,3-dimethylphenoxy)propyl]amino-1-phenylethanol;
1-[(2,6-dimethylphenoxy)propyl]amino-2-propanol;
2-[(2,6-dimethylphenoxy)propyl]amino-1-propanol;
R-2-[(2,6-dimethylphenoxy)propyl]amino-1-propanol;
2-[(2,6-dimethylphenoxy)propyl]amino-2-methyl-1-propanol;
1-[(2,6-dimethylphenoxy)propyl]amino-2-butanol;
2-[(2,6-dimethylphenoxy)propyl]amino-1-butanol;
2-[(2,6-dimethylphenoxy)propyl]amino-1-phenylethanol;
2-[(2-chlor-6-methylphenoxy)propyl]amino-1-propanol;
2-[(2-chlor-6-methylphenoxy)propyl]amino-1-butanol;
2-[(2,6-dimethylphenoxy)acetyl]-2-methylamino-1-ethanol;
2-[(2,6-dimethylphenoxy)acetyl]amino-1-propanol;
R-2-[(2,6-dimethylphenoxy)acetyl]amino-1-propanol;
S-2-[(2,6-dimethylphenoxy)acetyl]amino-1-propanol;
1-[(2,6-dimethylphenoxy)acetyl]amino-2-butanol;
trans-4-[(2,6-dimethylphenoxy)acetyl]amino-1-cyclohexanol;
1-[(2-chlor-6-methylphenoxy)acetyl]amino-2-propanol;
2-[(2-chlor-6-methylphenoxy)acetyl]amino-1-propanol;
R-2-[(2-chlor-6-methylphenoxy)acetyl]amino-1-propanol;
S-2-[(2-chlor-6-methylphenoxy)acetyl]amino-1-propanol;
1-[(2-chlor-6-methylphenoxy)acetyl]amino-2-butanol;
2-[(2-chlor-6-methylphenoxy)acetyl]amino-1-butanol; and
2-[(2,4,6-trimethylphenoxy)acetyl]amino-1-phenylethanol;
or the hydrochloride salts thereof.

4. The method of preventing and/or treating pain, comprising administering to a patient in need thereof a therapeutically effective amount of the aminoalkanol derivative selected from the group consisting of:

R,S-2N-[(2,3-dimethylphenoxy)ethyl]amino-1-propanol (1);
R,S-2N-[(2,3-dimethylphenoxy)ethyl]amino-1-butanol (2);
2N-[(2,3-dimethylphenoxy)ethyl]amino-2-methyl-1-propanol (3);
R,S-2N-[(2,3-dimethylphenoxy)ethyl]amino-1-phenylethanol (4);
R,S-1N-[(2,5-dimethylphenoxy)ethyl]amino-2-propanol (5);
R,S-2N-[(2,5-dimethylphenoxy)ethyl]amino-1-propanol (6);
R,S-1N-[(2,5-dimethylphenoxy)ethyl]amino-2-butanol (7);
R,S-2N-[(2,5-dimethylphenoxy)ethyl]amino-1-butanol (8);
R,S-2N-[(2,5-dimethylphenoxy)ethyl]amino-1-phenylethanol (9);
R-(−)-2N-[(2,6-dimethylphenoxy)ethyl]amino-1-propanol hydrochloride (12a);
S-(+)-2N-[(2,6-dimethylphenoxy)ethyl]amino-1-propanol hydrochloride (13a);
R,S-2N-[(2,6-dimethylphenoxy)ethyl]-2N-methylamino-1-propanol hydrochloride (14);
3N-[(2,6-dimethylphenoxy)ethyl]amino-3-methyl-1-butanol hydrochloride (15);
L-2N-[(2,6-dimethylphenoxy)ethyl]amino-3-methyl-1-butanol hydrochloride (16);
5N-[(2,6-dimethylphenoxy)ethyl]amino-1-pentanol hydrochloride (17);
D,L-trans-2N-[(2,6-dimethylphenoxy)ethyl]amino-1-cyclohexanol (18);
D,L-trans-2N-[(2,6-dimethylphenoxy)ethyl]amino-1-cyclohexanol hydrochloride (18a);
R,S-2N-[(2,6-dimethylphenoxy)ethyl]amino-1-phenylethanol (19);
R-(−)-2N-[(2,6-dimethylphenoxy)ethyl]amino-1-phenylethanol (20);
S-(+)-2N-[(2,6-dimethylphenoxy)ethyl]amino-1-phenylethanol (21);
R,S-2N-[(2,6-dimethylphenoxy)ethyl]-2N-methylamino-1-phenylethanol hydrochloride (22);
R,S-1N-[(2-chlor-6-methylphenoxy)ethyl]amino-2-propanol (23);
R,S-2N-[(2-chlor-6-methylphenoxy)ethyl]amino-1-propanol (24);
R,S-1N-[(2-chlor-6-methylphenoxy)ethyl]amino-2-butanol (25);
R,S-2N-[(2-chlor-6-methylphenoxy)ethyl]amino-1-butanol (26);
R,S-2N-[(2-chlor-6-methylphenoxy)ethyl]amino-1-butanol hydrochloride (26a);
R-(−)-2N-[(2-chlor-6-methylphenoxy)ethyl]amino-1-butanol (27);
S-(+)-2N-[(2-chlor-6-methylphenoxy)ethyl]amino-1-butanol (28);
2N-[(2-chlor-6-methylphenoxy)ethyl]amino-2-methyl-1,3-propandiol (29);
D,L-trans-2N-[(2-chlor-6-methylphenoxy)ethyl]amino-1-cyclohexanol (30);
R,S-2N-[(2-chlor-6-methylphenoxy)ethyl]amino-1-phenylethanol (31);
R,S-2N-[(2,3,5-trimethylphenoxy)ethyl]amino-1-propanol (38);
R,S-2N-[(2,3,5-trimethylphenoxy)ethyl]amino-1-butanol (39);
R-(−)-2N-[(2,3,5-trimethylphenoxy)ethyl]amino-1-butanol (40);
S-(+)-2N-[(2,3,5-trimethylphenoxy)ethyl]amino-1-butanol (41);
R,S-2N-[(2,3,5-trimethylphenoxy)ethyl]amino-1-phenylethanol hydrochloride (42);
R-(−)-2N-[(2,4,6-trimethylphenoxy)ethyl]amino-1-propanol (43);
D,L-trans-2N-[(2,4,6-trimethylphenoxy)ethyl]amino-1-cyclohexanol (44);
R,S-2N-[(2,4,6-trimethylphenoxy)ethyl]amino-1-phenylethanol (45);
R,S-2N-[(2,3-dimethylphenoxy)propyl]amino-1-propanol (46);
2N-[(2,3-dimethylphenoxy)propyl]amino-2-methyl-1-propanol (47);
R,S-2N-[(2,3-dimethylphenoxy)propyl]amino-1-butanol (48);
R,S-2N-[(2,3-dimethylphenoxy)propyl]amino-1-phenylethanol (49);
R,S-1N-[(2,6-dimethylphenoxy)propyl]amino-2-propanol (50);
R,S-2N-[(2,6-dimethylphenoxy)propyl]amino-1-propanol (51);
R-(−)-2N-[(2,6-dimethylphenoxy)propyl]amino-1-propanol hydrochloride (52);
2N-[(2,6-dimethylphenoxy)propyl]amino-2-methyl-1-propanol (53);
R,S-1N-[(2,6-dimethylphenoxy)propyl]amino-2-butanol (54);
R,S-2N-[(2,6-dimethylphenoxy)propyl]amino-1-butanol hydrochloride (55);
R,S-2N-[(2,6-dimethylphenoxy)propyl]amino-1-phenylethanol (56);
R,S-2N-[(2-chlor-6-methylphenoxy)propyl]amino-1-propanol (57);
R,S-2N-[(2-chlor-6-methylphenoxy)propyl]amino-1-butanol hydrochloride (58);
R,S-2N-[(2,6-dimethylphenoxy)acetyl]-2N-methylamino-1-ethanol (59);
R,S-2N-[(2,6-dimethylphenoxy)acetyl]amino-1-propanol (60);
R-(+)-2N-[(2,6-dimethylphenoxy)acetyl]amino-1-propanol (61);
S-(−)-2N-[(2,6-dimethylphenoxy)acetyl]amino-1-propanol (62);
R,S-1N-[(2,6-dimethylphenoxy)acetyl]amino-2-butanol (63);
trans-4N-[(2,6-dimethylphenoxy)acetyl]amino-1-cyclohexanol (64);
R,S-1N-[(2-chlor-6-methylphenoxy)acetyl]amino-2-propanol (68);
R,S-2N-[(2-chlor-6-methylphenoxy)acetyl]amino-1-propanol (69);
R-(−)-2N-[(2-chlor-6-methylphenoxy)acetyl]amino-1-propanol (70);
S-(+)-2N-[(2-chlor-6-methylphenoxy)acetyl]amino-1-propanol (71);
R,S-1N-[(2-chlor-6-methylphenoxy)acetyl]amino-2-butanol (72);
R,S-2N-[(2-chlor-6-methylphenoxy)acetyl]amino-1-butanol (73); and R,S-2N-[(2,4,6-trimethylphenoxy)acetyl]amino-1-phenylethanol (83);

or the hydrochloride salts thereof.

5. The method of claim 4 comprising administering to a patient in need thereof a therapeutically effective amount of the aminoalkanol derivative selected from the group consisting of:

2N-[(2-chlor-6-methylphenoxy)ethyl]amino-1-butanol (26);

R-(−)-2N-[(2-chlor-6-methylphenoxy)ethyl]amino-1-butanol (27); and

S-(+)-2N-[(2-chlor-6-methylphenoxy)ethyl]amino-1-butanol (28);

or the hydrochloride salts thereof.

6. The method of claim 4 comprising administering to a patient in need thereof a therapeutically effective amount of R-(−)-2N-[(2-chlor-6-methylphenoxy)ethyl]amino-1-butanol (27) or the hydrochloride salt thereof.

7. The method of claim 4 comprising administering to a patient in need thereof a therapeutically effective amount of the aminoalkanol derivative selected from the group consisting of:

R-(−)-2N-[(2,6-dimethylphenoxy)ethyl]amino-1-propanol hydrochloride (12a); and

S-(+)-2N-[(2,6-dimethylphenoxy)ethyl]amino-1-propanol hydrochloride(13a).

8. The method of claim 4 comprising administering to a patient in need thereof a therapeutically effective amount of R-(−)-2N-[(2,6-dimethylphenoxy)ethyl]amino-1-propanol hydrochloride (12a).

9. The method of claim 4 wherein the pain is neuropathic pain.

10. The method of claim 9, wherein the neuropathic pain is diabetic neuropathy, cancer pain, AIDS neuropathy, spinal cord injury, phantom limb pain, or fibromyalgia.

11. The method of claim 4 wherein the pain is inflammatory pain.

* * * * *